United States Patent
Yen et al.

(10) Patent No.: US 10,774,076 B2
(45) Date of Patent: Sep. 15, 2020

(54) BENZAZOLE COMPOUNDS AND METHODS FOR MAKING AND USING THE COMPOUNDS

(71) Applicant: Rigel Pharmaceuticals, Inc., South San Francisco, CA (US)

(72) Inventors: Rose Yen, San Francisco, CA (US); Yan Chen, Foster City, CA (US); Rajinder Singh, Belmont, CA (US); Vanessa Taylor, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 60 days.

(21) Appl. No.: 16/057,687

(22) Filed: Aug. 7, 2018

(65) Prior Publication Data

US 2018/0346458 A1 Dec. 6, 2018

Related U.S. Application Data

(62) Division of application No. 15/226,625, filed on Aug. 2, 2016, now Pat. No. 10,065,946.

(60) Provisional application No. 62/200,778, filed on Aug. 4, 2015.

(51) Int. Cl.
| | | |
|---|---|---|
| A61K 31/454 | (2006.01) | |
| C07D 413/14 | (2006.01) | |
| C07D 417/14 | (2006.01) | |
| C07D 471/04 | (2006.01) | |
| A61K 31/4545 | (2006.01) | |
| A61K 31/496 | (2006.01) | |
| A61K 31/5377 | (2006.01) | |
| A61K 45/06 | (2006.01) | |

(52) U.S. Cl.
CPC .......... *C07D 413/14* (2013.01); *A61K 31/454* (2013.01); *A61K 31/4545* (2013.01); *A61K 31/496* (2013.01); *A61K 31/5377* (2013.01); *A61K 45/06* (2013.01); *C07D 417/14* (2013.01); *C07D 471/04* (2013.01)

(58) Field of Classification Search
CPC .. C07D 413/14; C07D 417/14; C07D 471/04; A61K 45/06; A61K 31/5377; A61K 31/454; A61K 31/496; A61K 31/4545
See application file for complete search history.

(56) References Cited

U.S. PATENT DOCUMENTS

| | | | |
|---|---|---|---|
| 4,738,851 A | 4/1988 | Schoenwald et al. | |
| 4,882,150 A | 11/1989 | Kaufman | |
| 4,921,475 A | 5/1990 | Sibalis | |
| 5,008,110 A | 4/1991 | Benecke et al. | |
| 5,077,033 A | 12/1991 | Viegas et al. | |
| 5,087,240 A | 2/1992 | Sibalis | |
| 5,088,977 A | 2/1992 | Sibalis | |
| 5,163,899 A | 11/1992 | Sibalis | |
| 5,164,189 A | 11/1992 | Farhadieh et al. | |
| 5,254,346 A | 10/1993 | Tucker et al. | |
| 5,290,561 A | 3/1994 | Farhadieh et al. | |
| 5,336,168 A | 8/1994 | Sibalis | |
| 5,352,456 A | 10/1994 | Fallon et al. | |
| 5,403,841 A | 4/1995 | Lang et al. | |
| 5,521,222 A | 5/1996 | Ali et al. | |
| 5,698,219 A | 12/1997 | Valdivia et al. | |
| 5,776,445 A | 7/1998 | Cohen et al. | |
| 5,800,807 A | 9/1998 | Hu et al. | |
| 6,056,950 A | 5/2000 | Saettone et al. | |
| 6,197,934 B1 | 3/2001 | DeVore et al. | |
| 6,261,547 B1 | 7/2001 | Bawa et al. | |
| 9,732,095 B2 | 8/2017 | Gummadi et al. | |
| 9,951,086 B2 | 4/2018 | Bothe et al. | |
| 10,065,946 B2 * | 9/2018 | Yen .......................... A61P 13/12 | |

FOREIGN PATENT DOCUMENTS

| | | |
|---|---|---|
| WO | WO 2011/043371 | 4/2011 |
| WO | WO 2013/042137 | 3/2013 |
| WO | WO 2013/106535 | 7/2013 |
| WO | WO 2015/048281 | 4/2015 |
| WO | WO 2015/104662 | 7/2015 |

OTHER PUBLICATIONS

"5-Thiazolecarboxamide, 4-methyl-1-N-[2-(4-morpholinyl)-6-benzothiazolyl]-2-(2-pyridinyl)" *Chemical Library Document from STN*, Apr. 2007.

Sugimoto et al., "A new model of allergic rhinitis in rats by topical sensitization and evaluation of $H_1$-receptor antagonists," *Immunopharmacology* 48(1):1-7, Jun. 2000.

Tumas et al., "Anti-IgE efficacy in murine asthma models is dependent on the method of allergen sensitization," *The Journal of Allergy and Clinical Immunology* 107(6):1025-1033, 2001.

Wang et al., "IRAK-4 Inhibitors for Inflammation," *Current Topics in Medicinal Chemistry* 9:727-737, 2009.

* cited by examiner

*Primary Examiner* — Sudhakar Katakam

(74) *Attorney, Agent, or Firm* — Travis Young; Klarquist Sparkman, LLP

(57) ABSTRACT

Disclosed are novel benzazole compounds and compositions comprising the compounds. The compounds are useful as kinase inhibitors including interleukin receptor associated kinases (IRAK) inhibitors. Also disclosed are methods of making and using the compounds and compositions. The disclosed compounds and/or compositions may be used to treat or prevent an IRAK-associated disease or condition.

21 Claims, No Drawings

BENZAZOLE COMPOUNDS AND METHODS FOR MAKING AND USING THE COMPOUNDS

CROSS REFERENCE TO RELATED APPLICATIONS

This application is a divisional of U.S. patent application Ser. No. 15/226,625, filed on Aug. 2, 2016, which claims the benefit under 35 U.S.C. § 119(e) of the earlier filing date of U.S. Provisional Application No. 62/200,778, filed on Aug. 4, 2015. Each of these prior applications is incorporated herein by reference in their entirety.

FIELD

This disclosure concerns benzazole compounds, and embodiments of a method for making and using the compounds, such as for inhibiting kinases, including interleukin receptor-associated kinase (IRAK), and for treating related diseases and conditions.

BACKGROUND

Interleukin-1 receptor-associated kinases (IRAKs) are important mediators of signaling processes, such as toll-like receptors (TLR) and interleukin-1 receptor (IL-1R) signaling processes. IRAKs have been implicated in modulating signaling networks that control inflammation, apoptosis, and cellular differentiation. Four IRAK genes have been identified in the human genome (IRAK1, IRAK2, IRAK3 and IRAK4), and studies have revealed distinct, non-redundant biological roles. IRAK1 and IRAK4 have been shown to exhibit kinase activity.

SUMMARY

Disclosed herein are benzazole compounds, and compositions comprising such compounds, that are useful as, inter alia, immunomodulators, in particular, the present compounds are kinase inhibitors, such as by way of example IRAK inhibitors. Certain disclosed embodiments concern benzazole compounds having a formula I

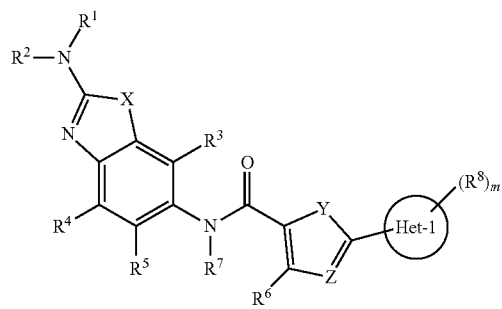

I or a pharmaceutically acceptable salt, solvate, hydrate, N-oxide, or prodrug thereof. With respect to formula I, X is O or S; Y is O or S; Z is N or $CR^9$; Het-1 is heterocyclyl; $R^1$ and $R^2$ independently are H, aliphatic, heteroaliphatic, heterocyclyl, aryl, araliphatic, or together with the nitrogen to which they are attached, form a heterocyclic ring; $R^3$, $R^4$, $R^5$, $R^6$ and $R^9$ independently are H, aliphatic, halo, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl or haloalkyl; $R^7$ is H, aliphatic, heteroaliphatic, heterocyclyl, aryl or araliphatic; each $R^8$ independently is aliphatic, halo, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl or haloalkyl; and m is from 0 to the number of possible substituents on Het-1. In some embodiments, X is O, and in other embodiments, X is S.

Het-1 may be a heteroaryl. Exemplary Het-1 may be selected from furan, thiophene, pyrazole, pyrrole, imidazole, oxazole, thiazole, isoxazole, isothiazole, 1,2,3-triazole, 1,2,4-triazole, 1,3,4-triazole, 1,2,3-oxadiazole, 1,2,4-oxadiazole, 1,3,4-oxadiazole, 1,2,5-oxadiazole, 1,2,3-thiadiazole, 1,2,4-thiadiazole, 1,3,4-thiadiazole, 1,2,5-thiadiazole, tetrazole, pyrimidine, pyridine, 1,2,3-triazine, 1,2,4-triazine, 1,3,5-triazine, pyrazine, pyridazine, quinoline, isoquinoline, indole, isoindole, benzofuran, benzothiophene, benzoimidazole, benzopyrazole, benzotriazole, pyrrolo[2,3-b]pyridine, pyrrolo[3,2-b]pyridine, pyrrolo[2,3-c]pyridine, pyrrolo[3,2-c]pyridine, pyrrolo[3,4-b]pyridine or pyrrolo[3,4-c]pyridine. In some embodiments, Het-1 is pyridine, pyrazole or pyrrolo[2,3-b]pyridine, and in particular embodiments,

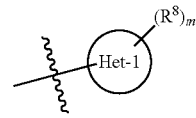

is selected from

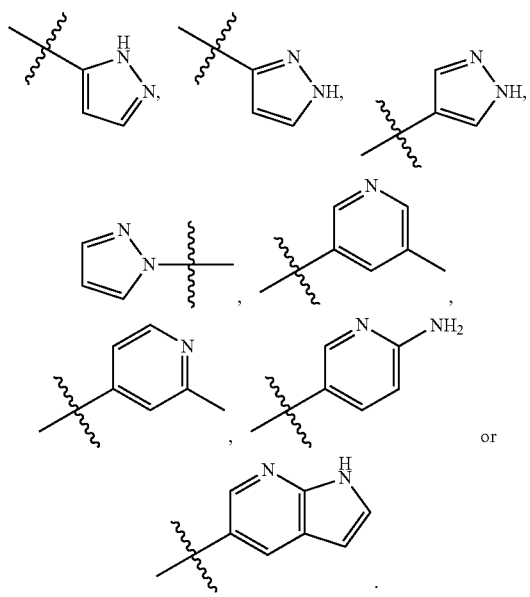

In some embodiments, the compound has a formula selected from

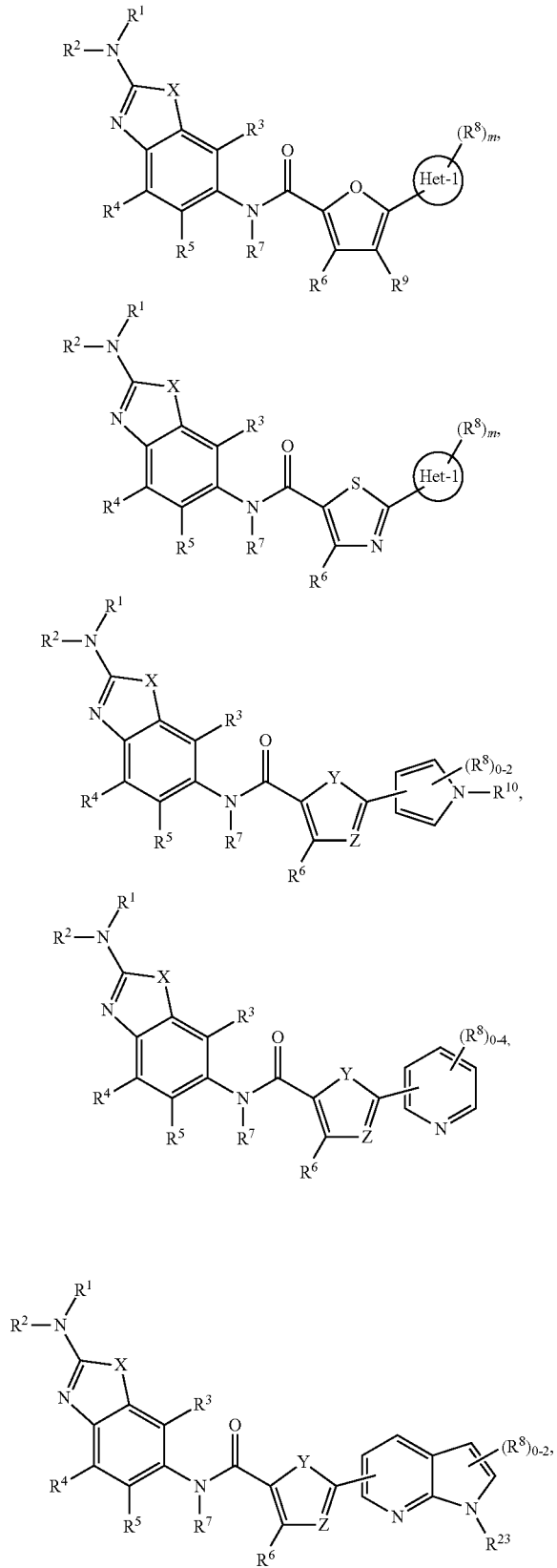

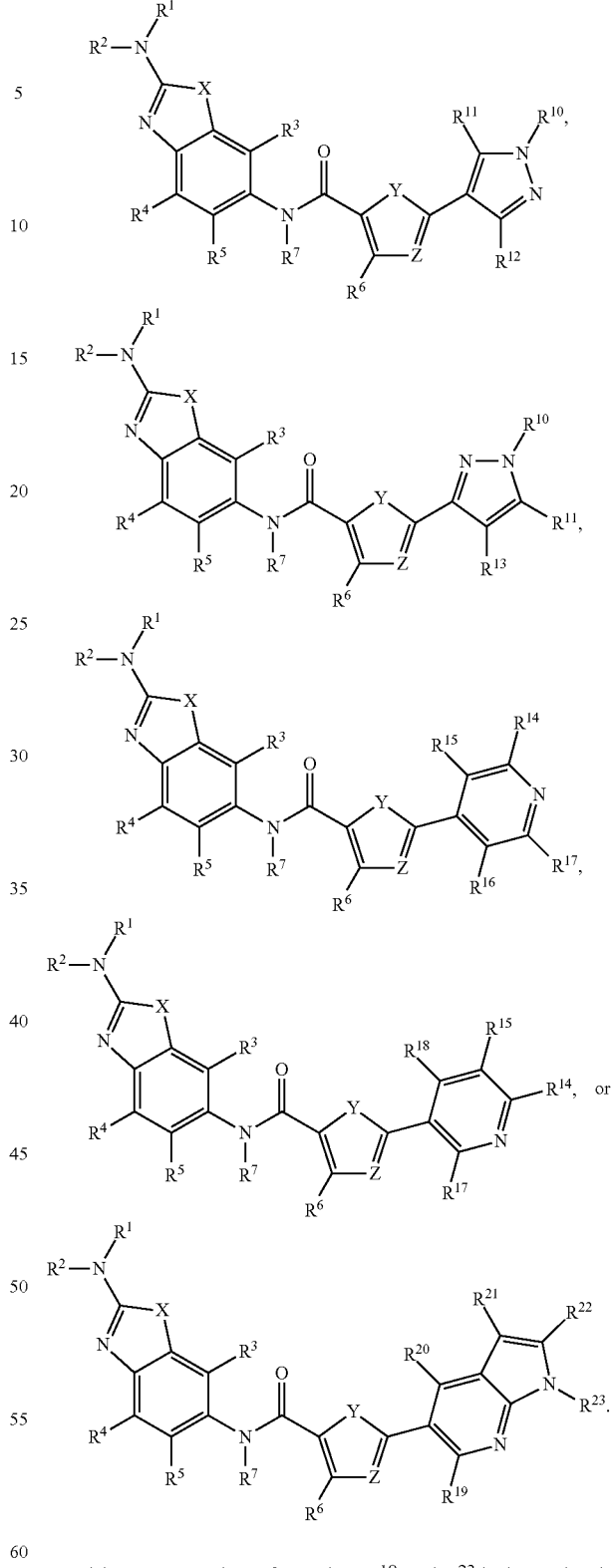

-continued

With respect to these formulas, $R^{10}$ and $R^{23}$ independently are H, aliphatic, heteroaliphatic, —O-aliphatic, heterocyclyl, aryl, araliphatic, —O-heterocyclyl, hydroxyl, cyano, carboxyl, carboxyl ester, acyl, amide, amino, sulfonyl, sulfonamide, or haloalkyl, typically H, aliphatic, aryl or heterocyclyl; and $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ independently are H, aliphatic, halogen, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl, or haloalkyl.

In any of the above embodiments, $R^5$ may be amino, aryl or heteroaryl. $R^5$ may be amino having a formula —NRR wherein each R independently is aliphatic, or both R groups together with the nitrogen attached thereto form an optionally substituted heterocyclic ring.

$R^1$ and $R^2$ independently may be H, aliphatic, heteroaliphatic, or together with the nitrogen attached thereto form a heteroaliphatic ring. In some embodiments, $R^1$ is H or alkyl, and $R^2$ is aliphatic or heteroaliphatic.

In particular embodiments, $R^3$, $R^4$, $R^6$ and $R^7$ are H.

Also disclosed herein are embodiments of a composition comprising a benzazole compound within the scope of the present invention and a pharmaceutically acceptable excipient. Disclosed exemplary compositions may also comprise a benzazole compound within the scope of the present invention and an additional therapeutic agent. Alternatively, the benzazole compounds, or compositions comprising the benzazole compounds, may be administered as a combination with an additional therapeutic(s). The additional therapeutic agent(s) may comprise an immunooncology agent. The benzazole compounds, or compositions comprising the benzazole compounds, and the additional therapeutic agent(s) may be administered to a subject substantially simultaneously, sequentially in any order, or within a time period such that the subject experiences an overlapping beneficial effect from both the benzazole compound or the composition comprising the benzazole compound, and the additional therapeutic agent(s).

Embodiments of a method for administering a benzazole compound or composition comprising a benzazole compound(s) are also disclosed. For example, disclosed herein are embodiments of a method for inhibiting or modulating an IRAK protein comprising contacting the IRAK protein with an effective amount of a benzazole compound. In some embodiments, the method comprises contacting the protein in vitro. In other embodiments, the IRAK protein may be in a subject. Exemplary compounds have an $EC_{50}$ of from greater than 0 to 5 µM, such as from greater than 0 to 1 µM. In certain embodiments, the method comprises administering to a subject in need thereof a therapeutically effective amount of a benzazole compound or composition comprising the benzazole compound. The method may be a method of treating a disease or condition for which an IRAK modulator or inhibitor is indicated.

The foregoing and other objects, features, and advantages of the invention will become more apparent from the following detailed description.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

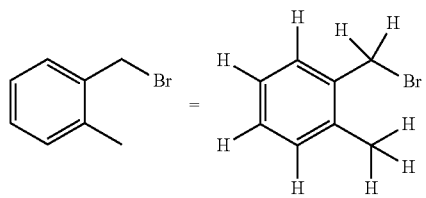

Sometimes a particular atom in a structure is described in textual formula as having a hydrogen or hydrogen atoms, for example —$CH_2CH_2$—. It will be understood by a person of ordinary skill in the art that the aforementioned descriptive techniques are common in the chemical arts to provide brevity and simplicity to description of organic structures.

A person of ordinary skill in the art will appreciate that the definitions may be combined to further describe a particular compound. For example, hydroxyaliphatic refers to an aliphatic group substituted with an hydroxy (—OH) group, and haloalkylaryl refers to an aryl group substituted with an alkyl group, where the alkyl group too is substituted with a halogen, and where the point of attachment to the parent structure is via the aryl moiety since aryl is the base name of the substituent.

As used herein, the term "substituted" refers to all subsequent modifiers in a term, for example in the term "substituted aryl$C_{1-8}$ alkyl," substitution may occur on the "$C_{1-8}$ alkyl" portion, the "aryl" portion or both portions of the aryl$C_{1-8}$ alkyl group. Also by way of example, alkyl includes substituted cycloalkyl groups.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted. In particular embodiments, the substituent may or may not be expressly defined as substituted, but is still contemplated to be optionally substituted. For example, an "alkyl" substituent may be unsubstituted or substituted, but an "unsubstituted alkyl" may not be substituted.

"Substituents" or "substituent groups" for substituting for one or more hydrogen atoms on saturated carbon atoms in the specified group or moiety may be any atom, or group of atoms, that a person of ordinary skill in the art would recognize as a suitable substituent or substituent group. Substituents" or "substituent groups" are, unless otherwise specified, —$R^{60}$, halo, =O, —$OR^{70}$, —$SR^{70}$, —$N(R^{80})_2$, haloalkyl, perhaloalkyl, —CN, —$NO_2$, =$N_2$, —$N_3$, —$SO_2R^{70}$, —$SO_3^-M^+$, $SO_3R^{70}$, —$OSO_2R^{70}$, —$OSO_3^{-1}M^+$, —$OSO_3R^{70}$, —$P(O)(O^-)_2(M^+)_2$, —$P(O)(O^-)_2M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^{-1}M^+$, —$CO_2R^{70}$, —$C(S)OR^{70}$, —$C(O)NR^{80})_2$, —$C(NR^{70})(R^{80})_2$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$ is $C_{1-6}$ alkyl; each $R^{70}$ is independently for each occurrence hydrogen or $R^{60}$; each $R^{80}$ is independently for each occurrence $R^{70}$ or alternatively, two $R^{80}$ groups, taken together with the nitrogen atom to which they are bonded, form a 3- to 7-membered heteroalicyclyl which optionally includes from 1 to 4 of the same or different additional heteroatoms selected from O, N and S, of which N optionally has H or $C_1$-$C_3$alkyl substitution; and each $M^+$ is a counter ion with a net single positive charge. Each $M^+$ is independently for each occurrence, for example, an alkali metal ion, such as $K^+$, $Na^+$, $Li^+$; an ammonium ion, such as $^+N(R^{60})_4$; or an alkaline metal earth ion, such as $[Ca^{2+}]_{0.5}$, $[Mg^{2+}]_{0.5}$, or $[Ba^{2+}]_{0.5}$ (a subscript "0.5" means, for example, that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, —$N(R^{80})_2$ includes —$NH_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon can be replaced with =O, =$NR^{70}$, =N—$OR^{70}$, =$N_2$ or =S.

Substituent groups for replacing hydrogen atoms on unsaturated carbon atoms in groups containing unsaturated carbons are, unless otherwise specified, —$R^{60}$, halo, —$O^-M^+$, —$OR^{70}$, —$SR^{70}$, —$N(R^{80})_2$, perhaloalkyl, —CN, —OCN, —SCN, —NO, —$NO_2$, —$N_3$, —$SO_2R^{70}$, —$SO_3^-M^+$, $SO_3R^{70}$, —$OSO_2R^{70}$, —$OSO_3^-M^+$, —$OSO_3R^{70}$, —$PO_3^{-2}(M^+)_2$, —$PO_3^{-2}M^{2+}$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})N(R^{80})_2$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

Substituent groups for replacing hydrogen atoms on nitrogen atoms in groups containing such nitrogen atoms are, unless otherwise specified, —$R^{60}$, —$O^-M^+$, —$OR^{70}$, —$SR^{70}$, —$S^-M^+$, —$N(R^{80})_2$, perhaloalkyl, —CN, —NO, —$NO_2$, —$S(O)_2R^{70}$, —$SO_3^-M^+$, —$SO_3R^{70}$, —$OS(O)_2R^{70}$, —$OSO_3^{-1}M^+$, —$OSO_3R^{70}$, —$PO_3^{2-}(M^+)_2$, —$PO_3^{2-}M^{2+}$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2R^{70}$, —$OC(S)OR^{70}$, —$NR^{70}C(O)R^{70}$, —$NR^{70}C(S)R^{70}$, —$NR^{70}CO_2R^{70}$, —$NR^{70}C(S)OR^{70}$, —$NR^{70}C(O)N(R^{80})_2$, —$NR^{70}C(NR^{70})R^{70}$ and —$NR^{70}C(NR^{70})N(R^{80})_2$, where $R^{60}$, $R^{70}$, $R^{80}$ and $M^+$ are as previously defined.

In one embodiment, a group that is substituted has 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

"Acyl" refers to the group —C(O)R, where R is H, aliphatic, heteroaliphatic, heterocyclic or aryl. Exemplary acyl moieties include, but are not limited to, —C(O)H, —C(O)alkyl, —C(O)$C_1$-$C_6$alkyl, —C(O)$C_1$-$C_6$haloalkyl-C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Aliphatic" refers to a substantially hydrocarbon-based group or moiety, including alkyl, alkenyl, alkynyl groups, cyclic versions thereof, such as cycloalkyl, cycloalkenyl or cycloalkynyl, and further including straight- and branched-chain arrangements, and all stereo and positional isomers as well. Unless expressly stated otherwise, an aliphatic group contains from one to twenty-five carbon atoms; for example, from one to fifteen, from one to ten, from one to six, or from one to four carbon atoms. Unless expressly stated otherwise, a cyclic aliphatic group contains from three to twenty-five carbon atoms; for example, from three to fifteen, from three to ten, or from three to six, carbon atoms. "Lower aliphatic" refers to an aliphatic group, including alkyl, alkenyl and alkynyl containing from one to ten carbon atoms, such as from one to six carbon atoms, or from three to ten carbon atoms, such as from three to six carbon atoms, for a cyclic lower aliphatic group. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group).

"Alkoxy" refers to the group —OR, where R is a substituted or unsubstituted alkyl or cycloalkyl group. In certain examples R is a $C_{1-6}$ alkyl or $C_{3-6}$ cycloalkyl group. Methoxy (—$OCH_3$) and ethoxy (—$OCH_2CH_3$) are exemplary alkoxy groups. In a substituted alkoxy, R is substituted alkyl or substituted cycloalkyl, examples of which useful in the presently disclosed compounds include haloalkoxy groups, such as —OCF$_2$H, and —OCF$_3$.

"Alkoxyalkyl" refers to the group -alkyl-OR, where R is a substituted or unsubstituted alkyl or cycloalkyl group. —CH$_2$CH$_2$—O—CH$_2$CH$_3$ is an exemplary alkoxyalkyl group.

"Alkyl" refers to a saturated aliphatic hydrocarbyl group having from 1 to 25 carbon atoms, typically 1 to 10 carbon atoms such as 1 to 6 carbon atoms and may be designated as $C_1$-$C_6$alkyl. An alkyl moiety may be substituted or unsubstituted. This term includes, by way of example, linear and branched hydrocarbyl groups such as methyl (CH$_3$), ethyl (—CH$_2$CH$_3$), n-propyl (—CH$_2$CH$_2$CH$_3$), isopropyl (—CH(CH$_3$)$_2$), n-butyl (—CH$_2$CH$_2$CH$_2$CH$_3$), isobutyl (—CH$_2$CH$_2$(CH$_3$)$_2$), sec-butyl (—CH(CH$_3$)(CH$_2$CH$_3$), t-butyl (—C(CH$_3$)$_3$), n-pentyl (—CH$_2$CH$_2$CH$_2$CH$_2$CH$_3$), and neopentyl (—CH$_2$C(CH$_3$)$_3$).

"Amino" refers to the group —NH$_2$, —NHR, or —NRR, where each R independently is selected from H, aliphatic, heteroaliphatic, aryl or heterocyclic, or two R groups together with the nitrogen attached thereto form a heterocyclic ring. Examples of such heterocyclic rings include those wherein two R groups together with the nitrogen to which they are attached form a —(CH$_2$)$_{2-5}$— ring optionally interrupted by one or two heteroatom groups, such as —O— or —N(R$^g$) such as in the groups

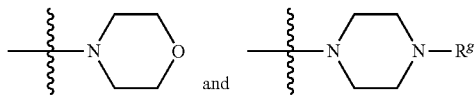

wherein R$^g$ is R$^{70}$, —C(O)R$^{70}$, —C(O)OR$^{60}$ or —C(O)N(R$^{80}$)$_2$.

"Amide" refers to the group —N(H)acyl, or —C(O)amino.

"Aryl" or "aromatic" refers to an aromatic group of, unless specified otherwise, from 5 to 15 ring atoms having a single ring (e.g., phenyl) or multiple fused rings in which at least one ring is aromatic (e.g., naphthyl). Aryl groups may be, for example, monocyclic, bicyclic, tricyclic or tetracyclic. For groups having multiple rings, at least one of which is aromatic and one is not, such groups are nevertheless referred to as "aryl" provided that the point of attachment to the remainder of the compound is through an atom of an aromatic portion of the aryl group. Unless otherwise stated, an aryl group may be substituted or unsubstituted.

"Araliphatic" refers to an aryl group attached to the parent via an aliphatic moiety. Araliphatic includes aralkyl or arylalkyl groups such as benzyl and phenylethyl.

"Azole" refers to a five-membered nitrogen heterocyclic ring that contains at least one other non-carbon atom typically selected from nitrogen, sulfur or oxygen. A "benzazole" is a fused ring comprising an azole ring and a phenyl ring. Exemplary benzazoles include, but are not limited to, benzthiazole, benzoxazole and benzimidazole.

"Carboxyl," or "carboxy" refer to —CO$_2$H.

"Carboxylate" refers to —C(O)O$^-$ or salts thereof.

"Carboxyl ester" or "carboxy ester" refers to the group —C(O)OR, where R is aliphatic, aryl, heteroaliphatic, and heterocyclic, including heteroaryl.

"Cyano" refers to the group —CN.

"Cycloaliphatic" refers to a cyclic aliphatic group having a single ring (e.g., cyclohexyl), or multiple rings, such as in a fused, bridged or spirocyclic system, at least one of which is aliphatic, provided that the point of attachment is through an atom of an aliphatic region of the cycloaliphatic group. Cycloaliphatic includes saturated and unsaturated systems, including cycloalkyl, cycloalkenyl and cycloalkynyl. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Heteroaliphatic" refers to an aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, acyclic or cyclic, such as a heteroalicyclyl group, chiral or achiral, and may include heterocycle, heterocyclyl, heterocycloaliphatic, or heterocyclic groups. One example of a heteroaliphatic group is CH$_3$OCH$_2$CH$_2$—.

"Heteroaryl" refers to an aryl group where one or more carbon atoms, such as methine (—CH═) or vinylene (—CH═CH—) groups, have been replaced by trivalent or divalent heteroatoms, respectively, in such a way as to maintain aromaticity, such as determined by the continuous, delocalized π-electron system characteristic of the aromatic group, and the number of out of plane π-electrons corresponding to the Hückel rule (4n+2).

"Heterocycloalkyl" and "heterocyclylalkyl" refer to a heterocyclyl moiety attached to the parent structure via an alkyl moiety, for example, (tetrahydropyran-4-yl)methyl, (pyridine-4-yl)methyl, morpholinoethyl or piperazin-1-yl-ethyl.

"Heterocyclyl," "heterocyclo" "heterocyclic" and "heterocycle" refer to aromatic and non-aromatic ring systems, and more specifically refer to a stable three- to fifteen-membered ring moiety comprising carbon atoms and at least one heteroatom, such as from one to five heteroatoms. Typical heteroatoms include, but are not limited to, N, O, S, P, Si or B. The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and the nitrogen, phosphorus, carbon, silicon or sulfur atoms in the heterocyclyl moiety can be optionally oxidized to various oxidation states. For convenience, nitrogens, particularly but not exclusively, those defined as annular (in the ring) aromatic nitrogens, are meant to include their corresponding N-oxide form, although not explicitly defined as such in a particular example. Thus, for a compound having, for example, a pyridyl ring, the corresponding pyridyl-N-oxide is included as another compound of the invention, unless expressly excluded by context. In addition, annular nitrogen atoms can be optionally quaternized. Heterocyclyl includes heteroaryl moieties and heteroalicyclyl or heterocycloaliphatic moieties, which are heterocyclyl rings that are partially or fully saturated. Thus a term such as "heterocyclylalkyl" includes heteroalicyclylalkyls and heteroarylalkyls. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, pyrrolopyridinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —NO$_2$.

"Patient" or "Subject" refers to mammals and other animals, particularly humans. Thus, disclosed methods are applicable to both human therapy and veterinary applications.

"Pharmaceutically acceptable excipient" refers to a substance, other than an active ingredient, that is included in a formulation of an active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is an excipient that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

"Pharmaceutically acceptable carrier" refers to an excipient that is a carrier or vehicle, such as a suspension aid, solubilizing aid, or aerosolization aid. See, for example, *Remington: The Science and Practice of Pharmacy*, The University of the Sciences in Philadelphia, Editor, Lippincott, Williams, & Wilkins, Philadelphia, Pa., 21$^{st}$ Edition (2005), incorporated herein by reference, which describes compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines, including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the benzazole compound may be a formate or sodium salt.

"Pharmaceutically effective amount" and "therapeutically effective amount" refer to an amount of a compound sufficient to treat a specified disorder or disease, or to ameliorate or eradicate one or more of its symptoms and/or to prevent the occurrence of the disease or disorder. The therapeutically effective amount can be determined by a person of ordinary skill in the art.

"Prodrug" refers to a compound that is transformed in vivo to yield a biologically active compound, particularly the parent compound, for example, by hydrolysis in the gut or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$ alkyl esters). Other prodrug moieties include phosphate esters, such as —$CH_2$—O—P(O)(OR')$_2$ or a salt thereof, wherein R' is H or lower alkyl, such as $C_{1-6}$ alkyl. Acceptable esters also include cycloalkyl esters and arylalkyl esters such as, but not limited to, benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by a combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein. A "hydrate" is a complex formed by a combination of water molecules with molecules or ions of the solute.

"Sulfonamide" refers to the group or moiety —$SO_2$amino, or —N(R$^c$)sulfonyl, where R$^c$ is H, aliphatic, aryl, heteroaliphatic, cyclic, and heterocyclic, including heteroaryl.

"Sulfonyl" refers to the group or —SH, —S-aliphatic, —S-aryl, —S-heteroaliphatic, —S-cyclic, —S-heterocyclyl, including —S-heteroaryl.

"Sulfinyl" refers to the group or moiety —S(O)H, —S(O)aliphatic, —S(O)aryl, —S(O)heteroaliphatic, —S(O)cyclic, —S(O)heterocyclyl, including —S(O)heteroaryl.

"Sulfonyl" refers to the group: —$SO_2$H, —$SO_2$aliphatic, —$SO_2$aryl, $SO_2$heteroaliphatic, —$SO_2$cyclic, —$SO_2$heterocyclyl, including —$SO_2$heteroaryl.

"Treating" or "treatment" as used herein concerns treatment of a disease or condition of interest in a patient or subject, including human or animal subjects, particularly a human having the disease or condition of interest, and includes by way of example, and without limitation:

(i) preventing the disease or condition from occurring in a patient or subject, in particular, when such patient or subject is predisposed to the condition but has not yet been diagnosed as having it;

(ii) inhibiting the disease or condition, for example, arresting or slowing its development;

(iii) relieving the disease or condition, for example, causing regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

Any of the groups referred to herein may be optionally substituted by at least one, possibly two or more, substituents as defined herein. That is, a substituted group has at least one, possible two or more, substitutable hydrogens replaced by a substituent or substituents as defined herein, unless the context indicates otherwise or a particular structural formula precludes substitution.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims may represent only one of the possible tautomeric, conformational isomeric, optical isomeric, or geometric isomeric forms, it will be understood that the disclosed compounds encompass any tautomeric, conformational isomeric, optical isomeric, and/or geometric isomeric forms of the compounds described herein, as well as mixtures of these various different isomeric forms, unless the context indicates that a single such isomer is intended. In cases of limited rotation, e.g. around the amide bond or between two directly attached rings such as the thiazole and pyridyl rings, atropisomers are also possible and are also specifically included in the compounds of the invention.

II. Benzazole Compounds and Compositions Thereof

A. Benzazole Compounds

Disclosed herein are benzazole compounds, methods of making the compounds, and methods of using the compounds. In one embodiment, the disclosed compounds are tyrosine kinase inhibitors. In a particular embodiment, the compounds are useful in blocking one or more cytokine signaling pathways, such as the IL-17 signaling pathway. For certain embodiments, the benzazole compounds are useful for treating conditions in which inhibition of an interleukin-1 receptor-associated kinase (IRAK) pathway is therapeutically useful. In some embodiments, the compounds directly inhibit an IRAK protein, such as IRAK1, IRAK2, IRAK3 or IRAK4.

Exemplary benzazole compounds within the scope of the present disclosure have a general formula I

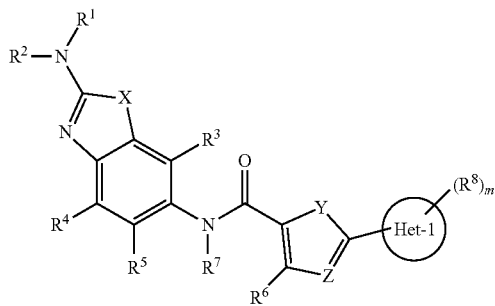

or a pharmaceutically acceptable salt, solvent, hydrate, N-oxide, prodrug, or combination thereof. With respect to formula I, Het-1 is a heterocyclyl, typically a heteroaryl; X is O or S; Y is O or N; and Z is S or $CR^9$. $R^1$ and $R^2$ independently are H; aliphatic, including alkyl, alkenyl, alkynyl, cycloalkyl, and cycloalkenyl; heteroaliphatic; heterocyclyl, including heteroaryl and heterocycloaliphatic; aryl or araliphatic; or together with the nitrogen to which they are attached, form an optionally substituted heterocyclic ring. $R^3$, $R^4$, $R^5$, $R^6$ and $R^9$ independently are H; aliphatic, including alkyl, alkenyl, alkynyl, cycloalkyl, cycloalkenyl and cycloalkynyl; halogen; heteroaliphatic; —O-aliphatic, such as alkoxy; heterocyclyl, including heteroaryl and heterocycloaliphatic; aryl; araliphatic; —O-heterocyclyl; hydroxyl; nitro; cyano; carboxyl; carboxyl ester; acyl; amide; amino; sulfonyl; sulfonamide; sulfanyl; sulfinyl; or haloalkyl; $R^7$ is H; aliphatic, including alkyl, alkenyl, alkynyl, cycloalkyl, and cycloalkenyl; heteroaliphatic; heterocyclyl, including heteroaryl and heterocycloaliphatic; aryl or araliphatic; or any two adjacent groups, such as $R^4$ and $R^5$, $R^5$ and $R^7$, $R^7$ and $R^6$ and/or $R^6$ and $R^9$, independently, together may form an aryl, heteroaryl, cycloaliphatic or heterocyclyl ring. Each $R^8$ independently is aliphatic, including alkyl, alkenyl, alkynyl, cycloalkyl, cycloalkenyl and cycloalkynyl; halogen; heteroaliphatic; —O-aliphatic, such as alkoxy; heterocyclyl, including heteroaryl and heterocycloaliphatic; aryl; araliphatic; —O-heterocyclyl; hydroxyl; nitro; cyano; carboxyl; carboxyl ester; acyl; amide; amino; sulfonyl; sulfonamide; sulfanyl; sulfinyl; or haloalkyl; and m is from 0 to the number of possible substituents on Het-1, such as from 0 to 1, 2, 3, 4, 5, or at least 6. Het-1 can be unsubstituted (when m is 0) or substituted. If Het-1 is unsubstituted a person of ordinary skill in the art will appreciate that there are sufficient implicit hydrogens on all carbons and heteroatoms to satisfy valance requirements. In particular embodiments of the disclosed benzazole compounds, each $R^8$ independently is selected from halo, $C_{1-6}$ haloalkyl such as —$CF_3$, —$CF_2H$ and —$CH_2CF_3$, $C_{1-6}$ alkyl, —$OC_{1-6}$ alkyl, amino or —$CH_2OP(O)(OR^{24})_2$ wherein each $R^{24}$ is independently H, $C_{1-6}$ alkyl or a counterion forming for example a pharmaceutically acceptable base addition salt with the phosphate moiety. In certain embodiments, at least one $R^8$ is amino, such as —$NH_2$; alkyl, such as $C_1$-$C_6$alkyl, such as methyl; or haloalkyl such as —$CF_3$, —$CF_2H$ or —$CH_2CF_3$. In particular embodiments, m is 1 and $R^8$ is —$NH_2$ or methyl.

For certain embodiments, Het-1 may be an optionally substituted 5- or 6-membered monocyclic heteroaryl or a fused heteroaryl comprising a 5- and/or 6-membered heteroaryl. In some examples, Het-1 is furan; thiophene; pyrazole; pyrrole; imidazole; oxazole; thiazole; isoxazole; isothiazole; triazole, such as 1,2,3-triazole, 1,2,4-triazole, or 1,3,4-triazole; oxadiazole, such as 1,2,3-oxadiazole, 1,2,4-oxadiazole, 1,3,4-oxadiazole or 1,2,5-oxadiazole; thiadiazole, such as 1,2,3-thiadiazole, 1,2,4-thiadiazole, 1,3,4-thiadiazole or 1,2,5-thiadiazole; tetrazole; pyrimidine; pyridine; triazine, such as 1,2,3-triazine, 1,2,4-triazine or 1,3,5-triazine; pyrazine; pyridazine; quinoline; isoquinoline; indole; isoindole; benzofuran; benzothiophene; benzoimidazole; benzopyrazole; benzotriazole; or pyrrolopyridine, such as pyrrolo[2,3-b]pyridine, pyrrolo[3,2-b]pyridine, pyrrolo[2,3-c]pyridine, pyrrolo[3,2-c]pyridine, pyrrolo[3,4-b]pyridine or pyrrolo[3,4-c]pyridine. In particular examples, Het-1 is pyrazole, pyridine or pyrrolo[2,3-b]pyridine, such as pyrazol-1-yl, pyrazol-3-yl, pyrazol-4-yl, pyrazol-5-yl, pyridin-2-yl, pyridin-3-yl, pyridin-4-yl, pyrrolo[2,3-b]pyridin-5-yl, pyrrolo[2,3-b]pyridin-2-yl, pyrrolo[2,3-b]pyridin-3-yl, pyrrolo[2,3-b]pyridin-4-yl or pyrrolo[2,3-b]pyridin-6-yl.

Examples of such Het-1 groups are represented by

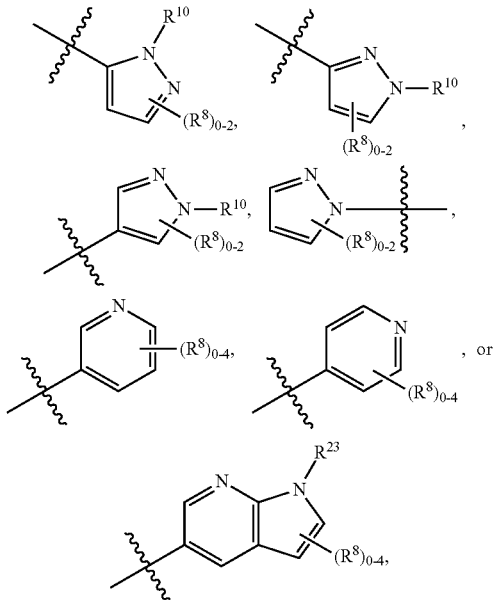

where $R^{10}$ and $R^{23}$ are selected from H, aliphatic, heteroaliphatic, —O-aliphatic, heterocyclyl, aryl, araliphatic, —O-heterocyclyl, hydroxyl, cyano, carboxyl, carboxyl ester, acyl, amide, amino, sulfonyl, sulfonamide, or haloalkyl.

In particular embodiments,

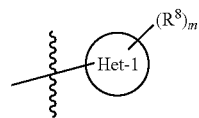

is selected from

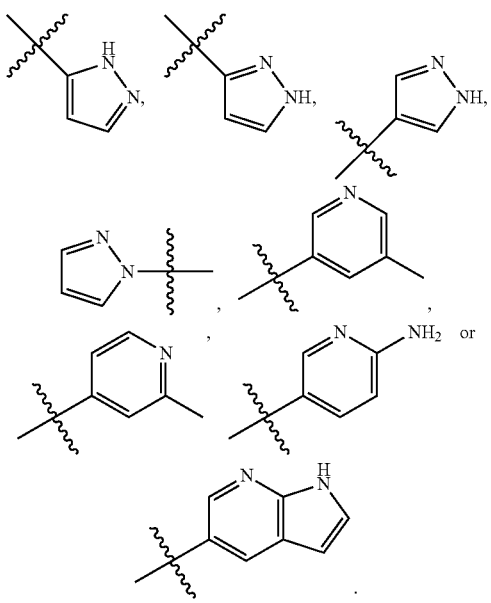

In certain embodiments, $R^5$ is amino, aryl or heterocyclyl. In some embodiments, $R^5$ is amino having a formula —NRR wherein each R independently is H or aliphatic, or both R groups together with the nitrogen attached thereto form a heterocyclic ring. In certain embodiment, $R^5$ is a cyclic amino selected from

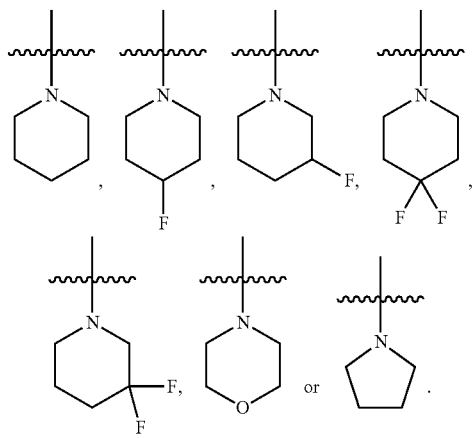

In other embodiments, $R^5$ is selected from

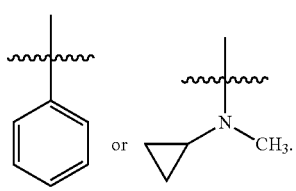 [SMILES: *c1ccccc1 ; *N(C)C1CC1]

In some embodiments, $R^1$ and $R^2$ together with the nitrogen attached thereto form a heterocyclic ring, typically a heteroaliphatic ring. In certain embodiments, the heteroaliphatic ring is morpholine, piperidine or piperazine. In other embodiments, $R^1$ and $R^2$ independently are H, aliphatic or heteroaliphatic. In certain examples, $R^1$ is H or alkyl, such as methyl, ethyl, propyl or isopropyl. In other embodiments, $R^2$ is aliphatic or heteroaliphatic. In certain embodiments, $R^2$ is aliphatic substituted with a heterocycloaliphatic. In particular embodiments, the —N($R^1$)($R^2$) moiety is selected from

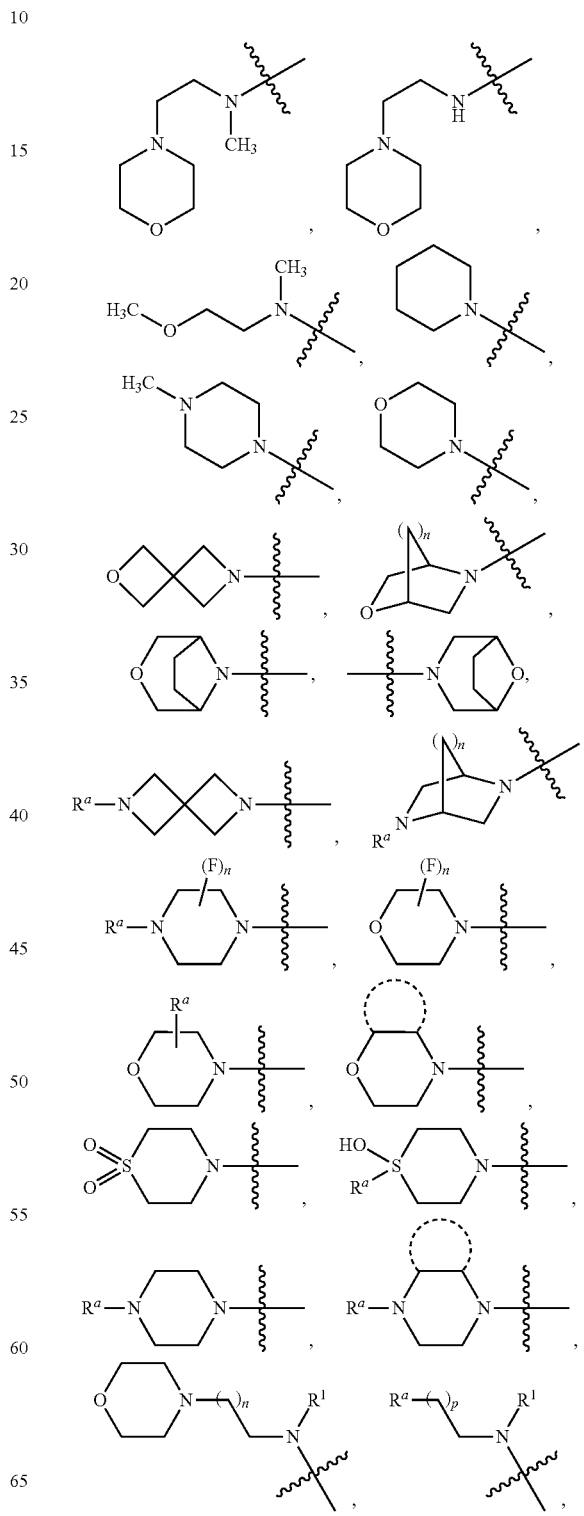

-continued

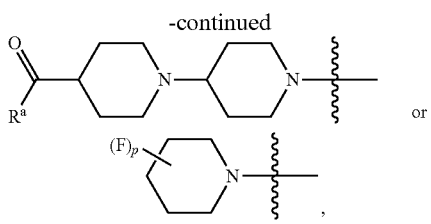

where $R^a$ is aliphatic, haloalkyl or acyl; n is 1 or 2; and p is 0, 1 or 2. $R^a$ may be alkyl, haloalkyl or acyl, such as $CH_3$, $CF_3$, $CF_2H$, or $R^bC(O)$—. In some embodiments, $R^b$ is aliphatic or haloalkyl, such as alkyl or haloalkyl, and in certain embodiments, $R^b$ is $CH_3$, $CF_3$ or $CF_2H$.

Also with respect to formula I, Het-1 may be: 1A) a 5-membered heteroaryl; 1B) a 6-membered heteroaryl; 1C) a fused heteroaryl; 1D) selected from pyridine, pyrazole, or pyrrolopyridine; 1E) pyridine; 1F) pyrazole; 1G) pyrrolopyridine; 1H) pyridin-4-yl; 1I) pyridin-4-yl substituted at least at the 2-position; 1J) pyridin-4-yl substituted at least at the 2-position with an alkyl moiety; 1K) 2-methylpyridin-4-yl; 1L) pyridin-3-yl; 1M) pyridin-3-yl substituted at least at the 6-position; 1N) pyridin-3-yl substituted at least at the 6-position with an amino moiety; 1O) 6-aminopyridin-3-yl; 1P) pyrazol-4-yl; 1Q) pyrazol-3-yl; or 1R) pyrrolo[2,3-b]pyridin-5-yl.

With respect to Het-1 embodiments 1A to 1R, $R^5$ may be, in combination with 1A to 1R: 2A) 5-membered heterocyclyl; 2B) 6-membered heterocyclyl; 2C) selected from piperidine, morpholine or pyrrolidine; 2D) piperidine; 2E) morpholine; 2F) pyrrolidine; 2G) piperidin-1-yl; 2H) 4-fluoropiperidin-1-yl; 2I) 4,4-difluoropiperidin-1-yl; 2J) 3-fluoropiperidin-1-yl; 2K) 3,3-difluoropiperidin-1-yl; 2L) pyrrolidin-1-yl; or 2M) morpholino.

A person of ordinary skill in the art will understand that any of 2A to 2M may be combined with any of 1A to 1R, to form any and all combinations between such substituents.

With respect to the Het-1 embodiments 1A to 1R and the $R^5$ embodiments 2A to 2M, the —$N(R^1)(R^2)$ moiety may be, in any combination with 1A to 1R and 2A to 2M: 3A) heterocyclyl; 3B) selected such that $R^1$ and $R^2$ independently are H, aliphatic or heteroaliphatic; 3C) morpholine; 3D) piperidine; 3E) piperazine; 3F) 4-methyl-1-piperazinyl; 3G) morpholino; 3H) piperidin-1-yl; 3I) selected such that $R^1$ is alkyl and $R^2$ is heteroaliphatic; 3J) selected such that $R^1$ is H or alkyl and $R^2$ is alkyl substituted with a heterocycloaliphatic; 3K) N-(2-methoxyethyl)-N-methylamino; 3L)N-methyl-N-(2-morpholinoethyl)amino; or 3M) (2-morpholinoethyl)amino.

A person of ordinary skill in the art will understand that any of 3A to 3M may be combined with any of 1A to 1R and 2A to 2M, to form any and all combinations between such substituents.

With respect to the Het-1 embodiments 1A to 1R, the $R^5$ embodiments 2A to 2M, and the —$N(R^1)(R^2)$ moiety embodiments 3A to 3M, X may be, in any combination with 1A to 1R, 2A to 2M and 3A to 3M: 4A) oxygen; or 4B) sulfur.

A person of ordinary skill in the art will understand that either of 4A or 4B may be combined with any of 1A to 1R, 2A to 2M and 3A to 3M, to form any and all combinations between such substituents.

With respect to the Het-1 embodiments 1A to 1R, the $R^5$ embodiments 2A to 2M, the —$N(R^1)(R^2)$ moiety embodiments 3A to 3M and the X embodiments 4A to 4B, Y may be, in any combination with 1A to 1R, 2A to 2M, 3A to 3M and 4A to 4B: 5A) oxygen; or 5B) sulfur.

A person of ordinary skill in the art will understand that either of 5A or 5B may be combined with any of 1A to 1R, 2A to 2M, 3A to 3M and 4A to 4B, to form any and all combinations between such substituents.

With respect to the Het-1 embodiments 1A to 1R, the $R^5$ embodiments 2A to 2M, the —$N(R^1)(R^2)$ moiety embodiments 3A to 3M, the X embodiments 4A to 4B, and the Y embodiments 5A to 5B, Z may be, in any combination with 1A to 1R, 2A to 2M, 3A to 3M, 4A to 4B and 5A to 5B: 6A) nitrogen; or 6B) CH.

A person of ordinary skill in the art will understand that either of 6A or 6B may be combined with any of 1A to 1R, 2A to 2M, 3A to 3M, 4A to 4B and 5A to 5B to form any and all combinations between such substituents.

In some embodiments of formula I, Y is O and Z is $CR^9$, leading to compounds having a formula II

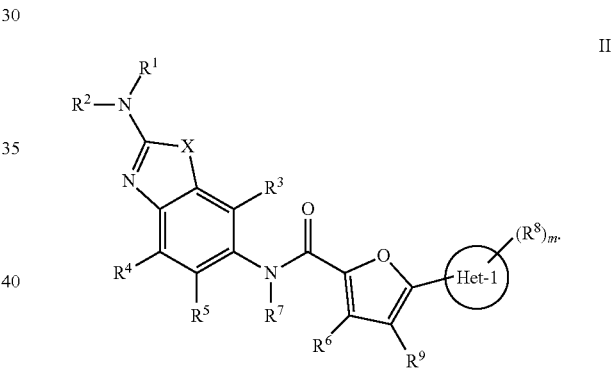

In other embodiments of formula I, Y is S and Z is N, leading to compounds having a formula III

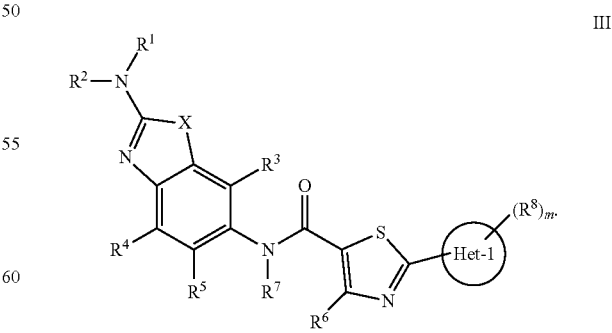

With respect to formulas II and III, $R^1$, $R^2$, $R^3$, $R^4$, $R^5$, $R^6$, $R^7$, $R^8$, $R^9$, m, Het-1 and X are as previously defined for formula I.

In some examples of formula I, Het-1 is pyrazole, pyridine or pyrrolopyridine, leading to compounds having a formula selected from

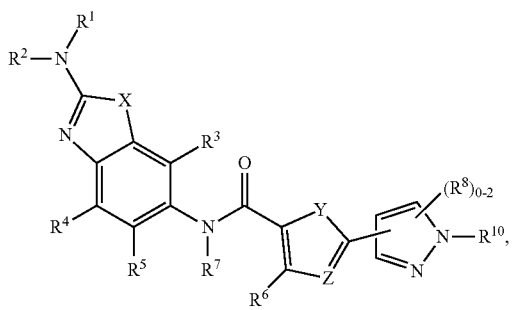
IV

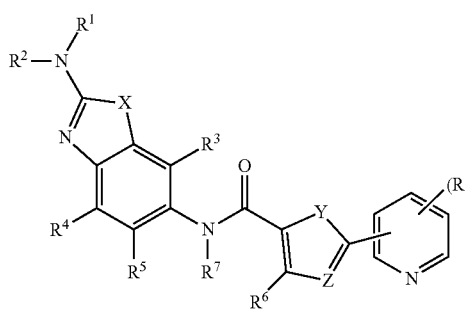
V

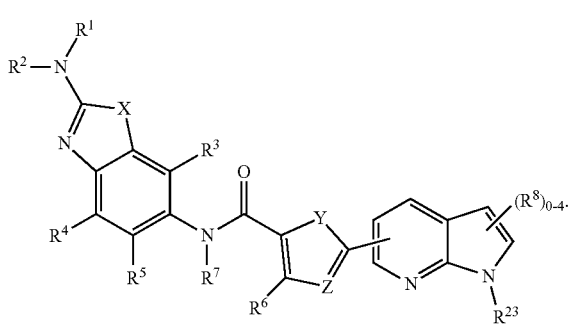
VI

With respect to formulas IV, V and VI, $R^1$, $R^2$, $R^3$, $R^4$, $R^5$, $R^6$, $R^7$, $R^8$, $R^9$, X, Y and Z are as previously defined for formula I, and $R^{10}$ and $R^{23}$ are selected from H, aliphatic, heteroaliphatic, —O-aliphatic, heterocyclyl, aryl, araliphatic, —O-heterocyclyl, hydroxyl, cyano, carboxyl, carboxyl ester, acyl, amide, amino, sulfonyl, sulfonamide, or haloalkyl. Certain substituents, such as $R^8$, in these formulae, are not shown directly bonded to an atom in the ring. This indicates that substituents may be bonded to any available position or combinations of positions on the ring. This is a particular consideration when the substituent is other than hydrogen.

In some embodiments of formula IV, the compound has a formula selected from

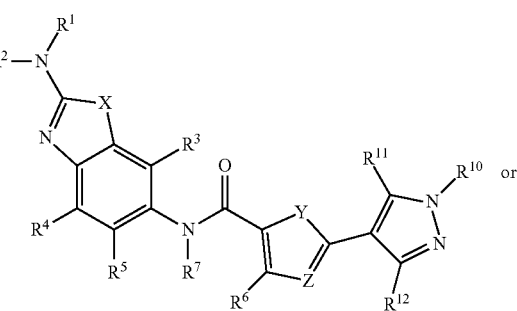
VII

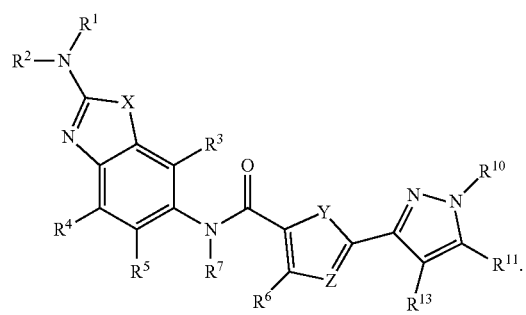
VIII

With respect to formulas VII and VIII, $R^1$, $R^2$, $R^3$, $R^4$, $R^5$, $R^6$, $R^7$, $R^9$, X, Y and Z are as previously defined for formula I. $R^{10}$ is H, aliphatic, aryl or heterocyclyl. $R^{11}$, $R^{12}$ and $R^{13}$ independently are H; aliphatic, including alkyl, alkenyl, alkynyl, cycloalkyl, cycloalkenyl and cycloalkynyl; halogen; heteroaliphatic; —O-aliphatic, such as alkoxy; heterocyclyl, including heteroaryl and heterocycloaliphatic; aryl; araliphatic; —O-heterocyclyl; hydroxyl; nitro; cyano; carboxyl; carboxyl ester; acyl; amide; amino; sulfonyl; sulfonamide; sulfanyl; sulfinyl; or haloalkyl. In some examples, $R^{10}$, $R^{11}$, $R^{12}$ and $R^{13}$ are all H.

In some embodiments of formula V, the compound has a formula selected from

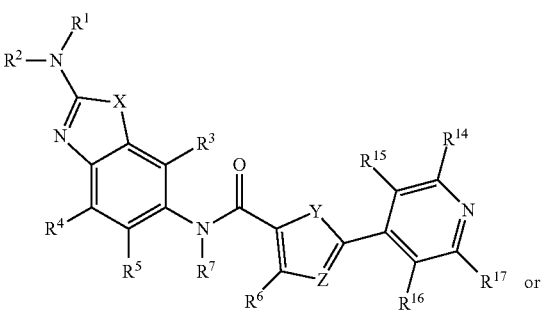
IX

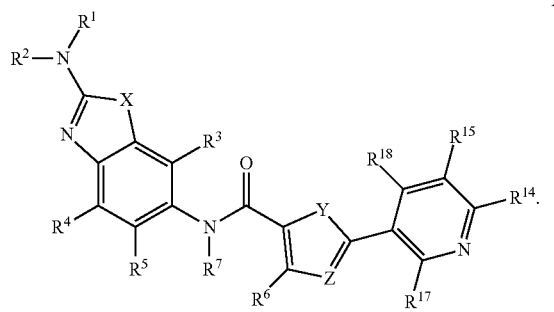

X

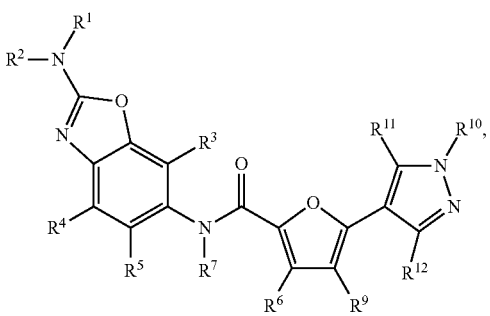

XII

With respect to formulas IX and X, $R^1$, $R^2$, $R^3$, $R^4$, $R^5$, $R^6$, $R^7$, $R^9$, X, Y and Z are as previously defined for formula I, and $R^{14}$, $R^{15}$, $R^{16}$, $R^{17}$ and $R^{18}$ independently are H; aliphatic, including alkyl, alkenyl, alkynyl, cycloalkyl, cycloalkenyl and cycloalkynyl; halogen; heteroaliphatic; —O-aliphatic, such as alkoxy; heterocyclyl, including heteroaryl and heterocycloaliphatic; aryl; aralphatic; —O-heterocyclyl; hydroxyl; nitro; cyano; carboxyl; carboxyl ester; acyl; amide; amino; sulfonyl; sulfonamide; sulfanyl; sulfinyl; or haloalkyl.

In some embodiments of formula IX, $R^{14}$ is alkyl, and may be lower alkyl, particularly $C_{1-6}$ alkyl, such as methyl. In other embodiments of formula IX, $R^{15}$, $R^{16}$, and $R^{17}$ are H.

In some embodiments of formula X, $R^{14}$ is amino, and may be $NH_2$. In other embodiments of formula X, $R^{15}$ is alkyl, and may be $C_1$-$C_6$alkyl such as methyl. In certain embodiments of formula X, $R^{15}$, $R^{16}$ and $R^{18}$ are H.

In some embodiments of formula VI, the compound has a formula XI

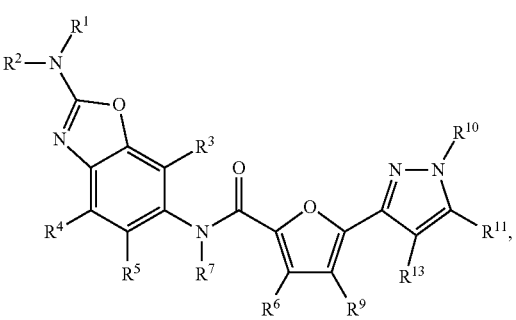

XIII

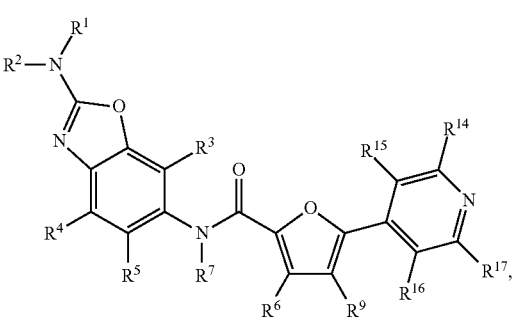

XIV

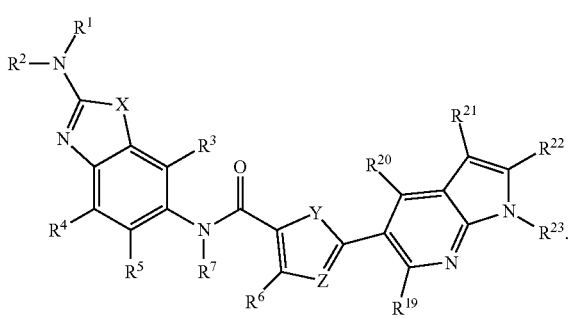

XI

With respect to formula XI, $R^1$, $R^2$, $R^3$, $R^4$, $R^5$, $R^6$, $R^7$, $R^9$, X, Y and Z are as previously defined for formula I. $R^{19}$, $R^{20}$, $R^{21}$ and $R^{22}$ independently are H; aliphatic, including alkyl, alkenyl, alkynyl, cycloalkyl, cycloalkenyl and cycloalkynyl; halogen; heteroaliphatic; —O-aliphatic, such as alkoxy; heterocyclyl, including heteroaryl and heterocycloaliphatic; aryl; aralphatic; —O-heterocyclyl; hydroxyl; nitro; cyano; carboxyl; carboxyl ester; acyl; amide; amino; sulfonyl; sulfonamide; sulfanyl; sulfinyl; or haloalkyl. $R^{23}$ is H, aliphatic, aryl or heterocyclyl. In some embodiments of formula XI, $R^{19}$, $R^{20}$, $R^{21}$, $R^{22}$ and $R^{23}$ are H.

In some embodiments of formula II, the compound has a formula selected from

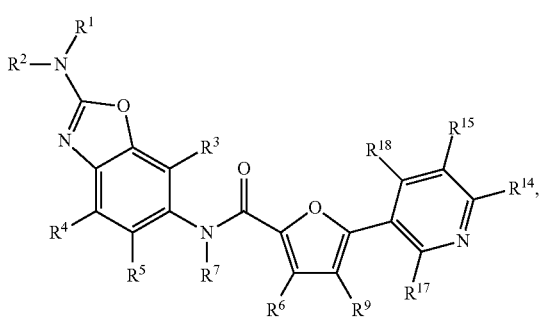

XV

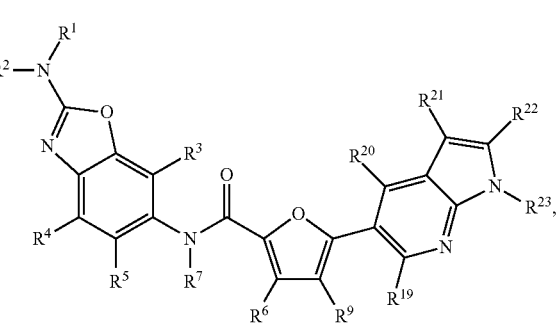

XVI

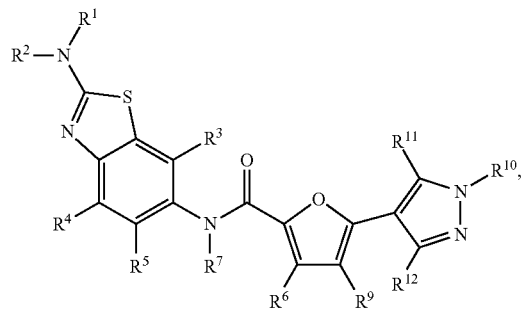
XVII
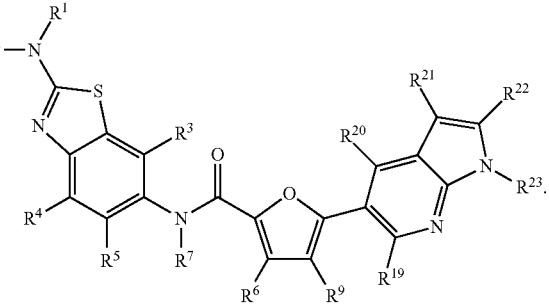
XXI
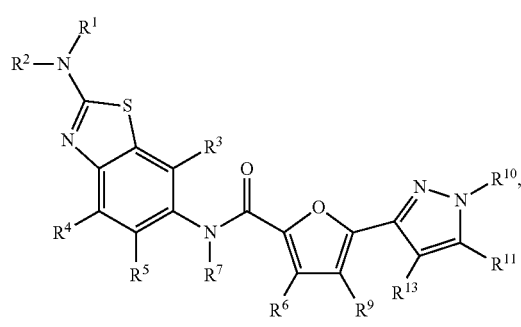
XVIII
In some embodiments of formula III, the compound has a formula selected from
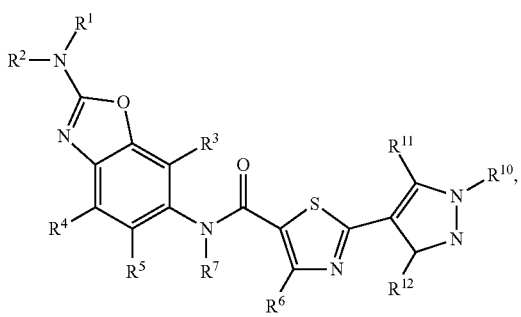
XXII
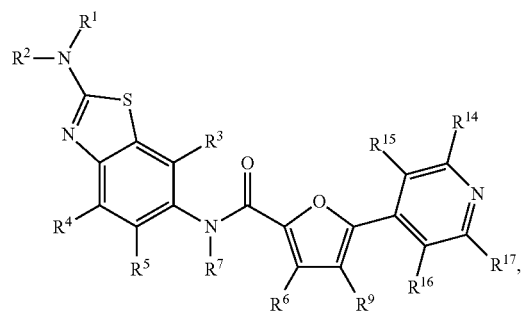
XIX
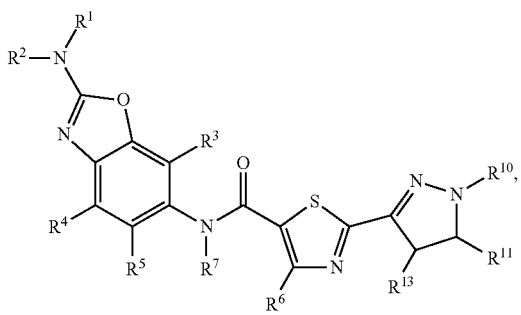
XXIII
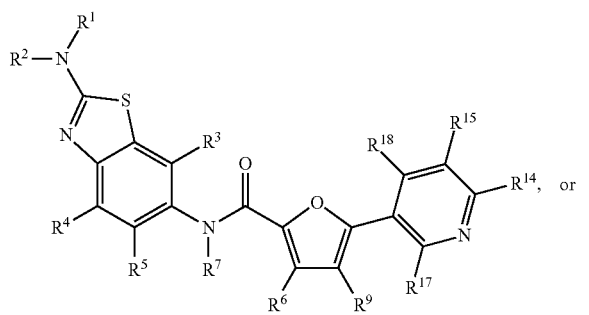
XX
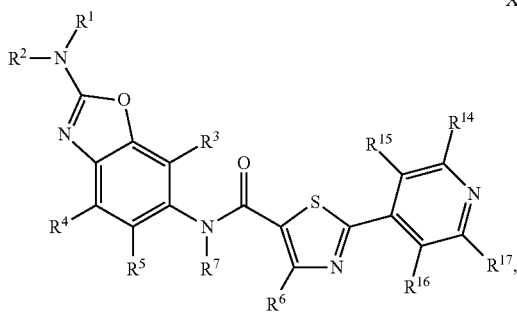
XXIV

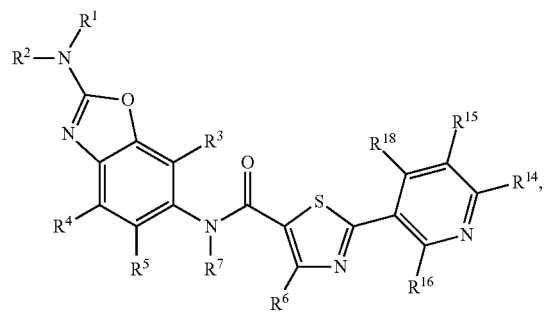

XXV

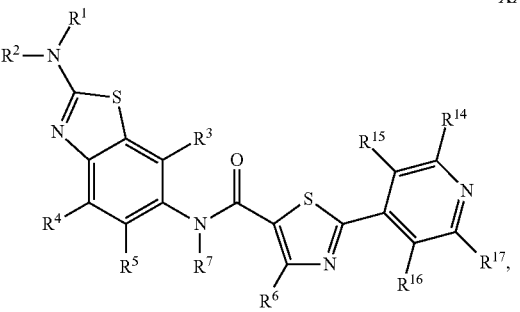

XXIX

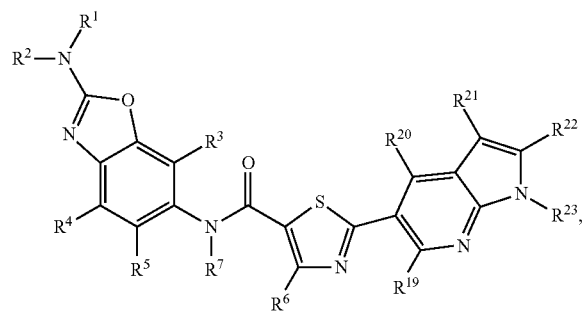

XXVI

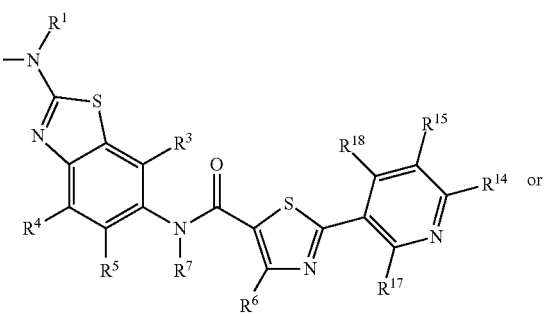

XXX

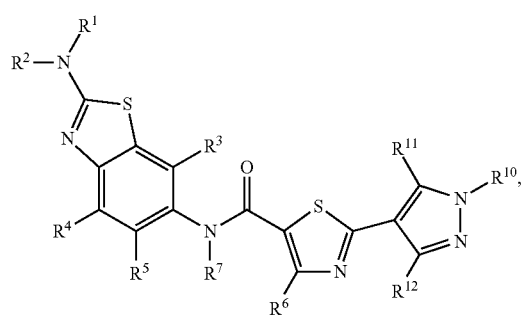

XXVII

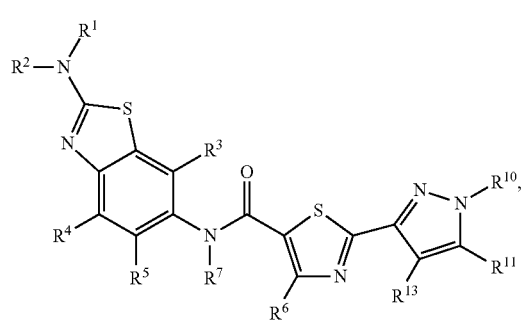

XXVIII

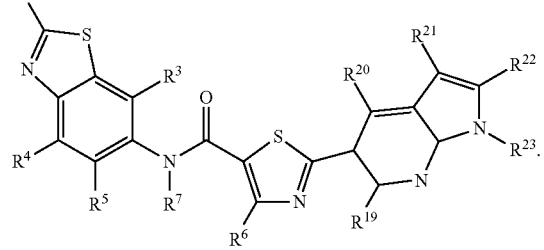

XXXI

With respect to formulas XII to XXXI, $R^1$, $R^2$, $R^3$, $R^4$, $R^5$, $R^6$, $R^7$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are as previously described for formulas I to XI. In some examples, $R^3$, $R^4$, $R^6$, $R^7$, $R^{10}$, $R^{11}$, $R^{12}$, $R^{13}$, $R^{15}$, $R^{16}$, $R^{17}$, $R^{18}$, $R^{19}$, $R^{20}$, $R^{21}$, $R^{22}$ and/or $R^{23}$ are H, and/or, $R^{14}$ is H, alkyl, such as methyl, or amino, such as —$NH_2$.

In some embodiments of formulas I-XXXI, $R^3$, $R^4$, $R^6$ and/or $R^7$ are H.

Exemplary compounds according to formula I include, without limitation, the compounds in the table below and or pharmaceutically acceptable salts thereof:
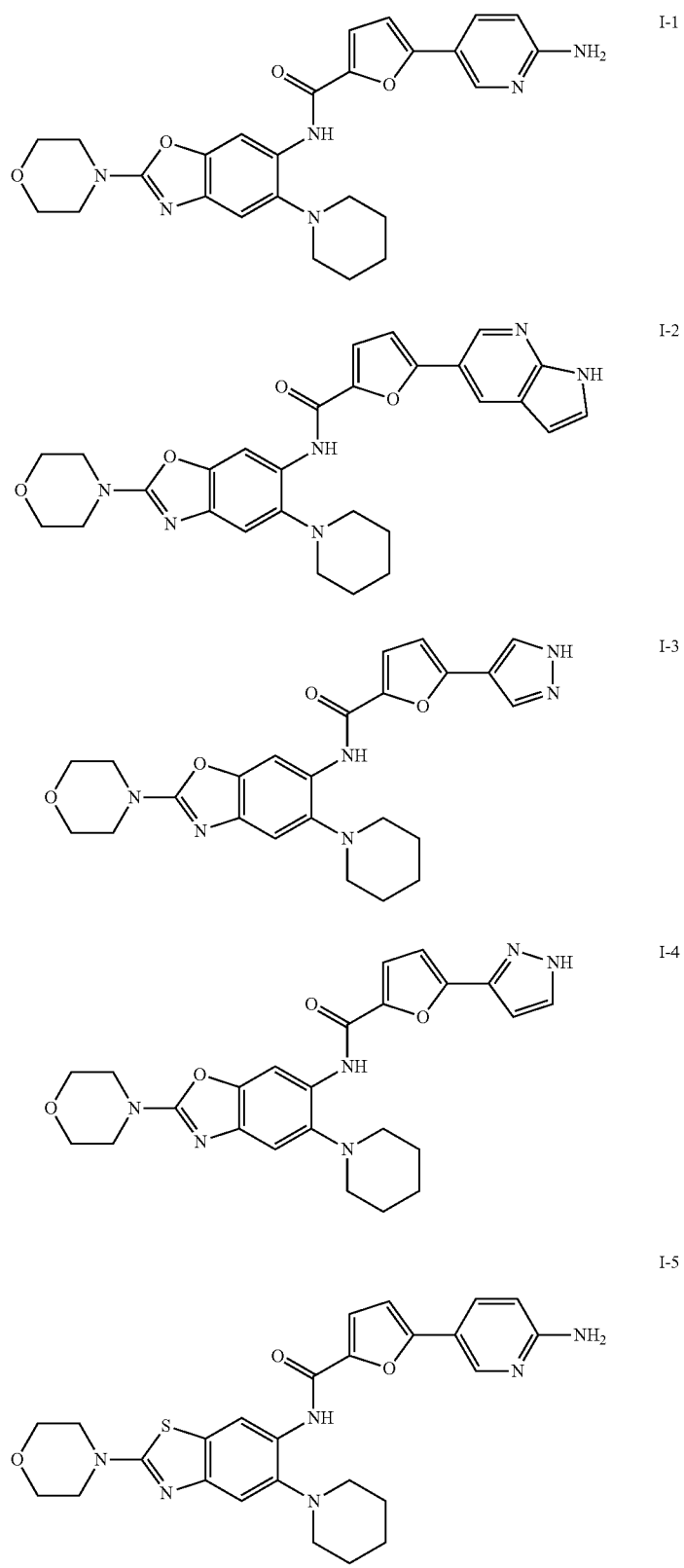
I-1
I-2
I-3
I-4
I-5

-continued
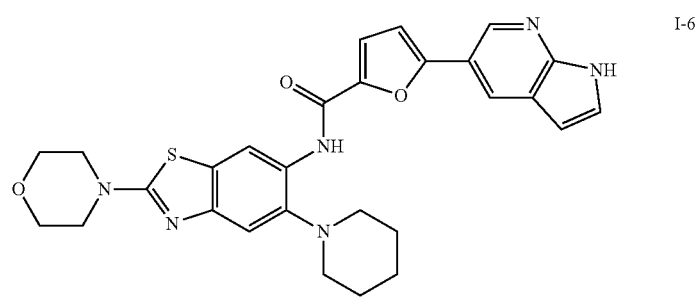
I-6
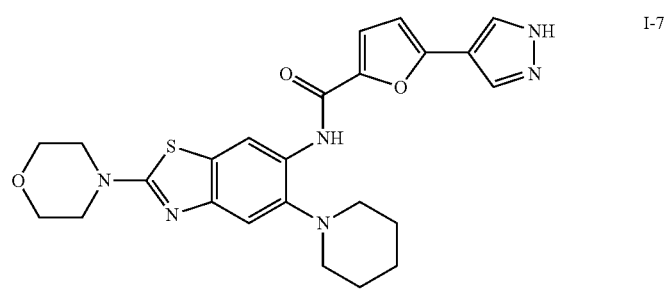
I-7
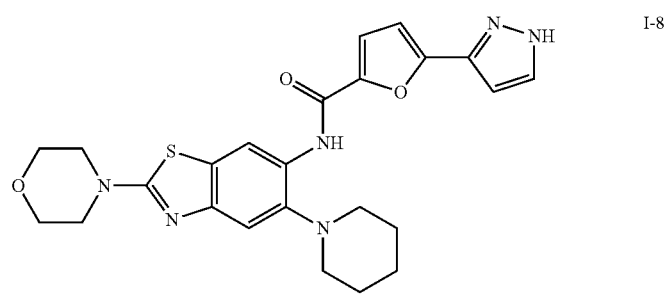
I-8
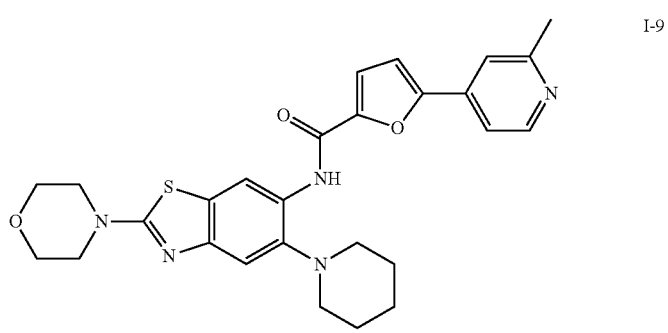
I-9
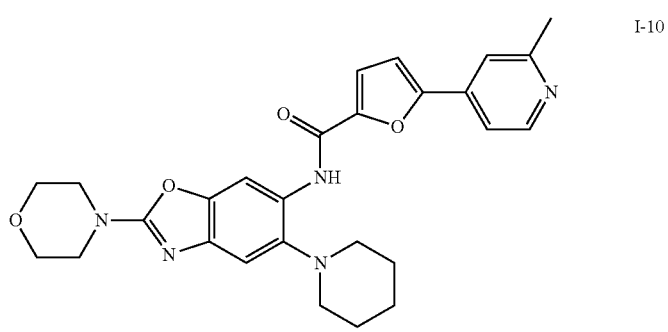
I-10

-continued
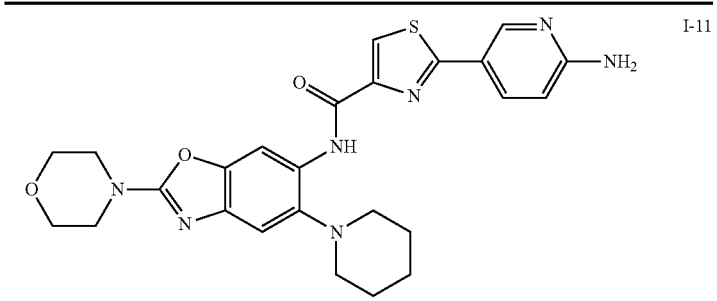
I-11
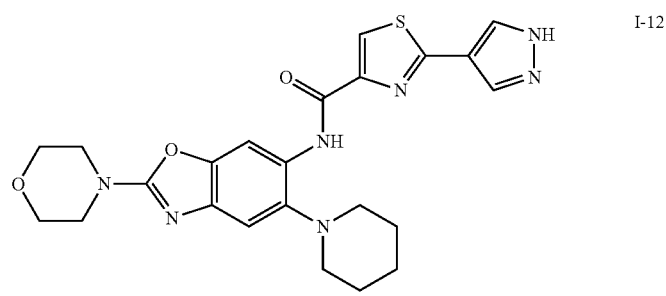
I-12
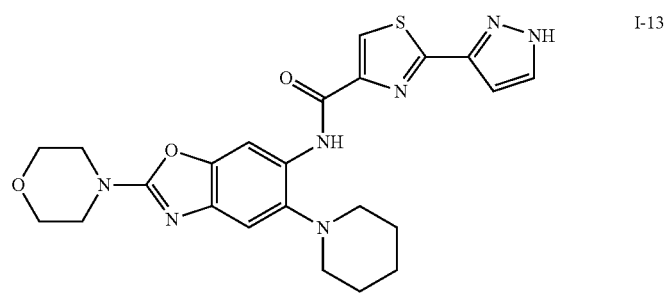
I-13
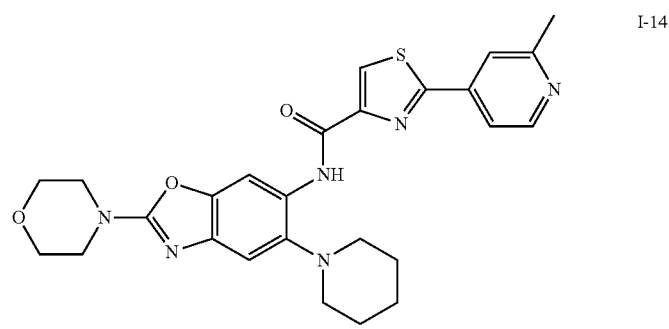
I-14
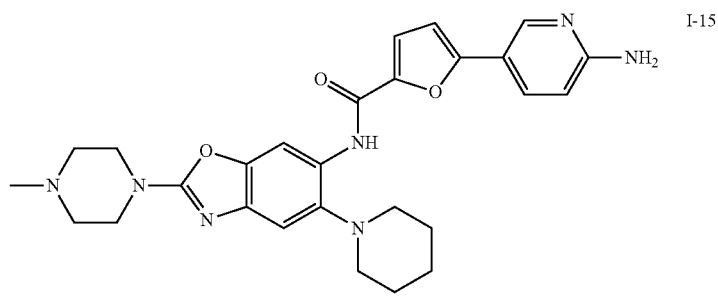
I-15

-continued
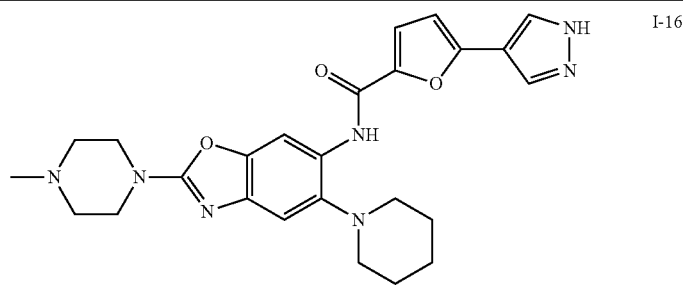
I-16
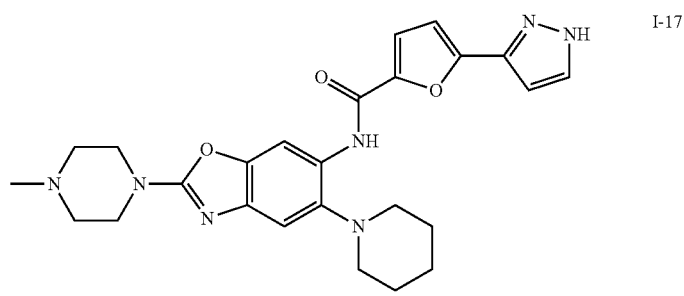
I-17
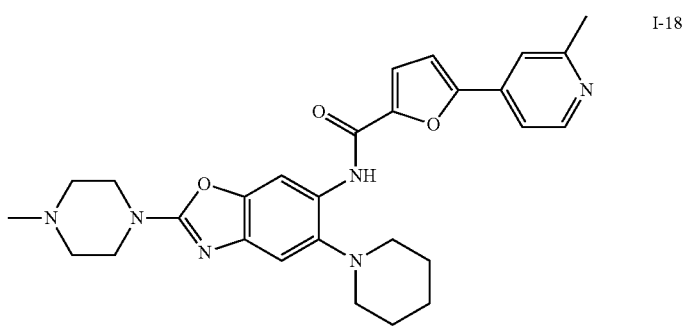
I-18
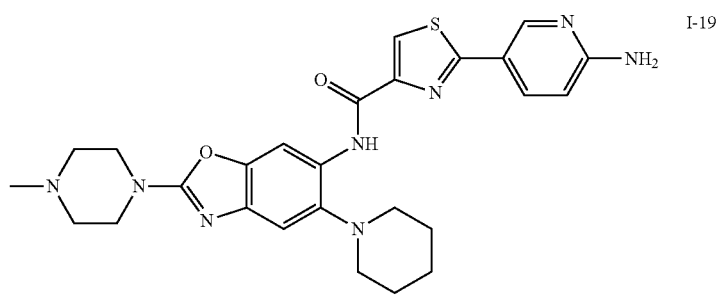
I-19
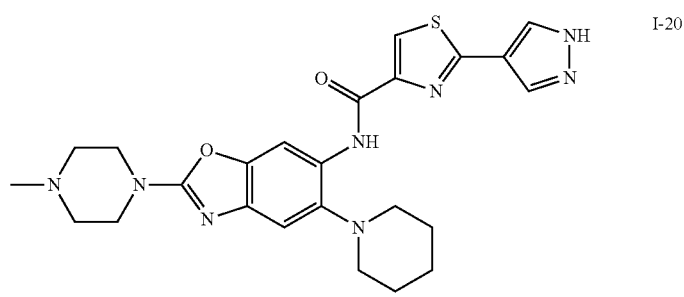
I-20

-continued
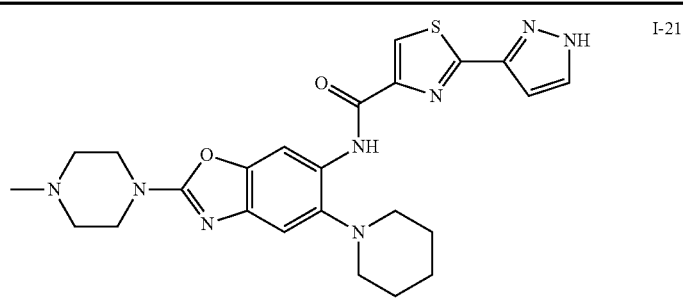
I-21
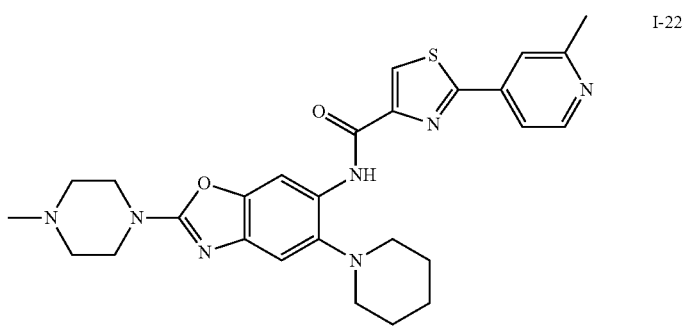
I-22
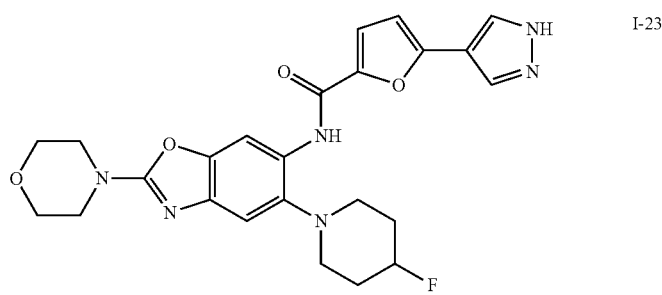
I-23
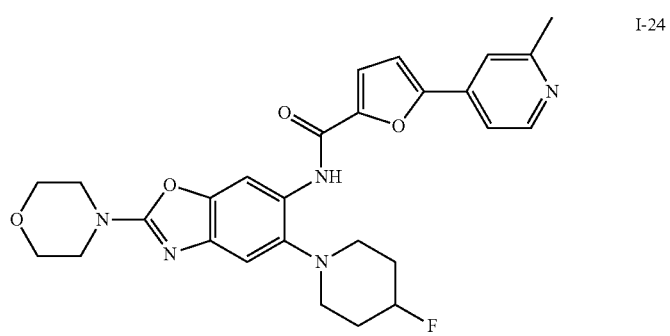
I-24
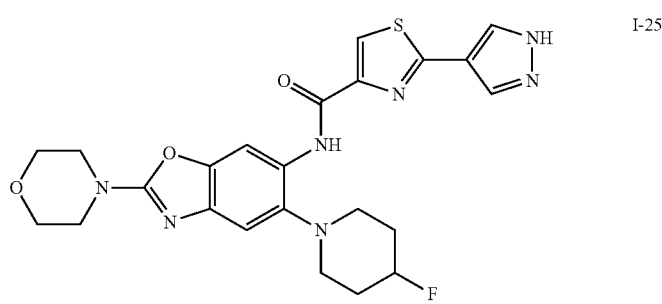
I-25

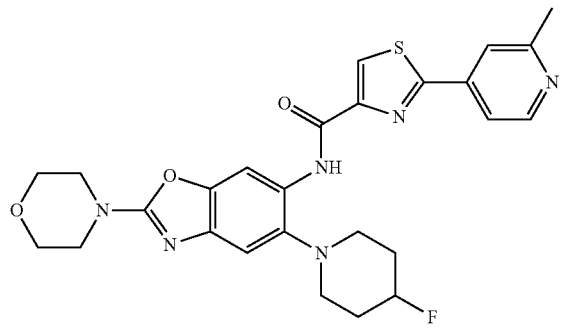 [SMILES: Cc1cc(-c2nc(C(=O)Nc3cc4oc(N5CCOCC5)nc4cc3N3CCC(F)CC3)cs2)ccn1]
I-26
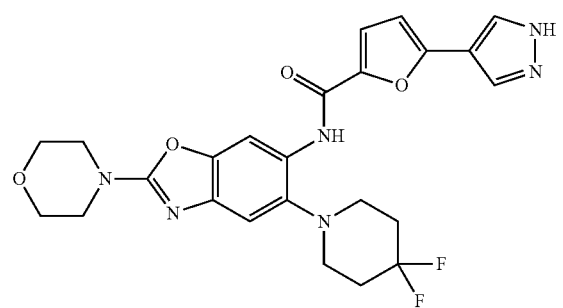 [SMILES: O=C(Nc1cc2oc(N3CCOCC3)nc2cc1N1CCC(F)(F)CC1)c1ccc(-c2cn[nH]c2)o1]
I-27
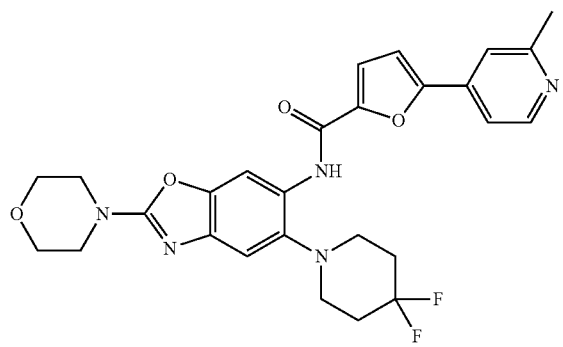 [SMILES: Cc1cc(-c2ccc(C(=O)Nc3cc4oc(N5CCOCC5)nc4cc3N3CCC(F)(F)CC3)o2)ccn1]
I-28
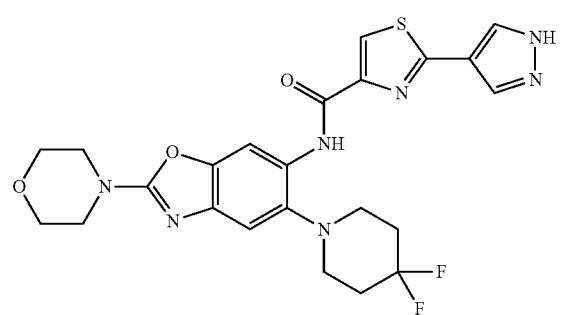 [SMILES: O=C(Nc1cc2oc(N3CCOCC3)nc2cc1N1CCC(F)(F)CC1)c1csc(-c2cn[nH]c2)n1]
I-29
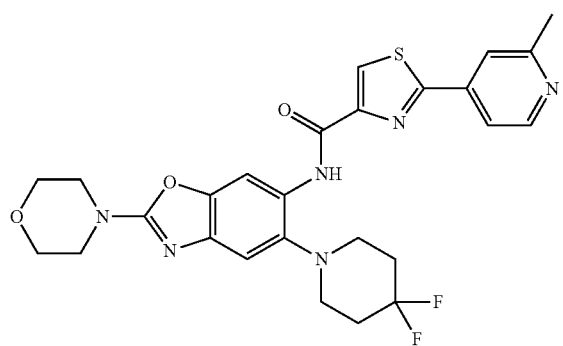 [SMILES: Cc1cc(-c2nc(C(=O)Nc3cc4oc(N5CCOCC5)nc4cc3N3CCC(F)(F)CC3)cs2)ccn1]
I-30

-continued
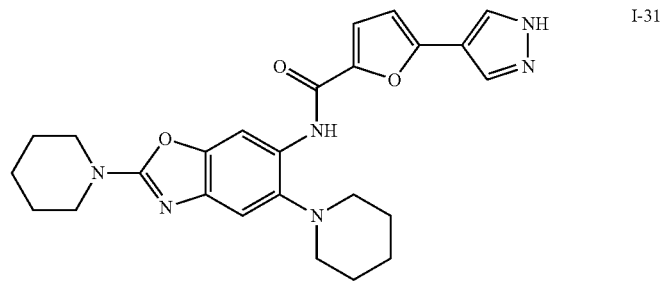
I-31
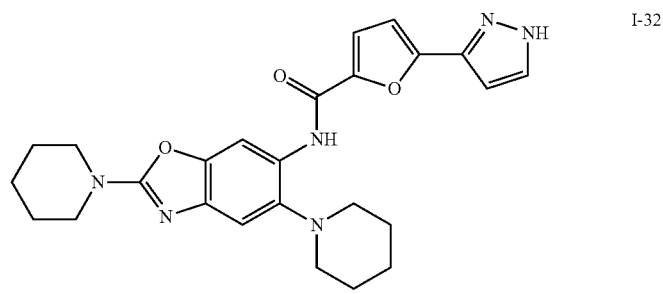
I-32
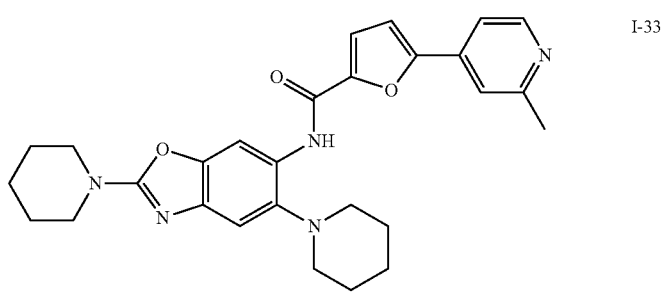
I-33
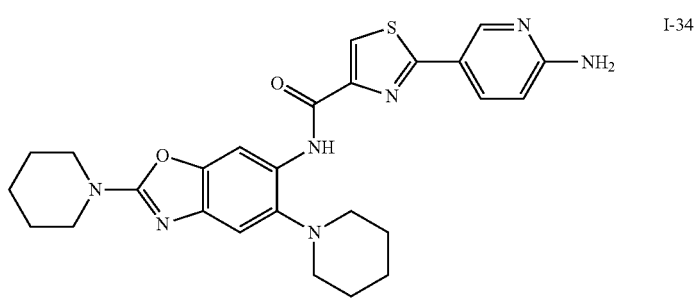
I-34
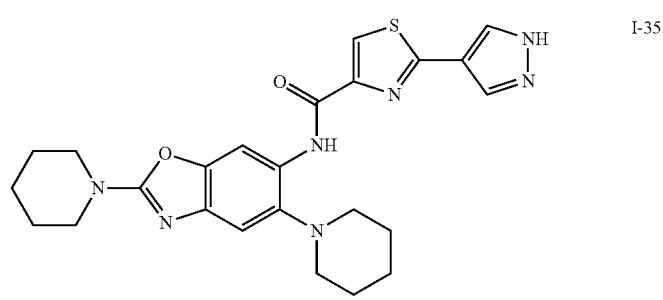
I-35

-continued
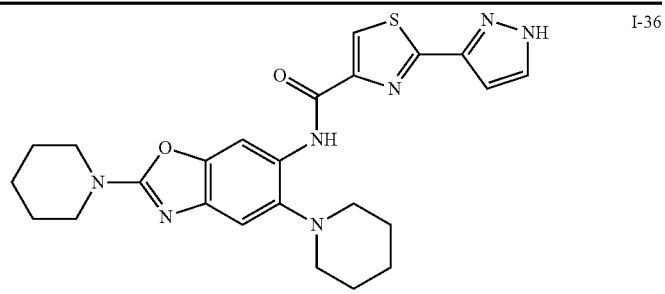
I-36
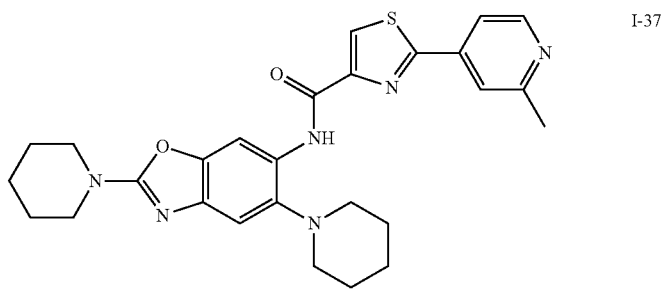
I-37
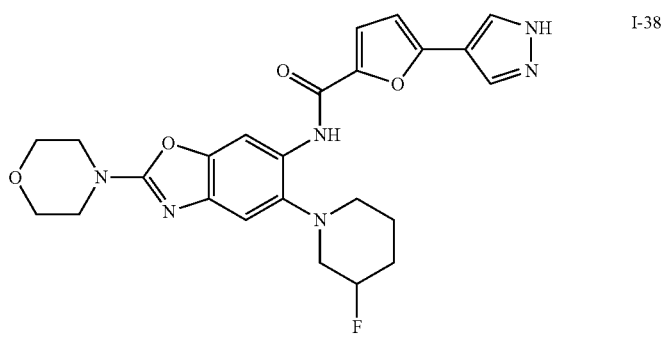
I-38
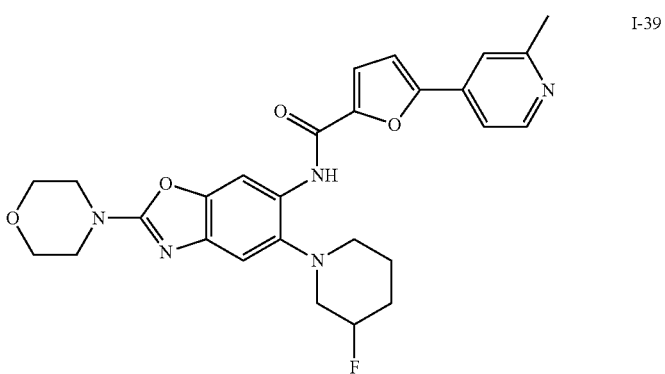
I-39
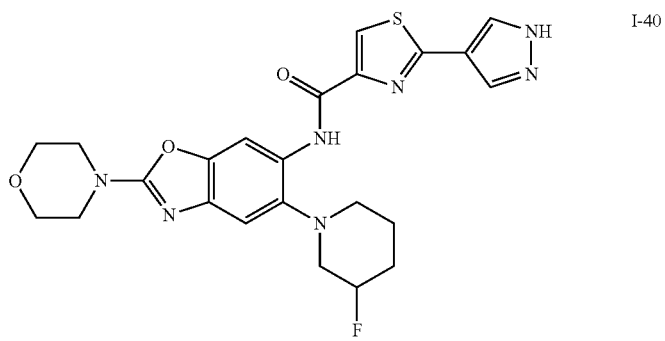
I-40

-continued
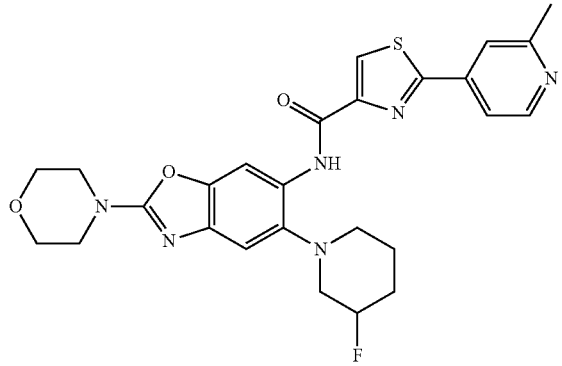 [SMILES: Cc1cc(-c2nc(C(=O)Nc3cc4oc(N5CCOCC5)nc4cc3N3CCCC(F)C3)cs2)ccn1]
I-41
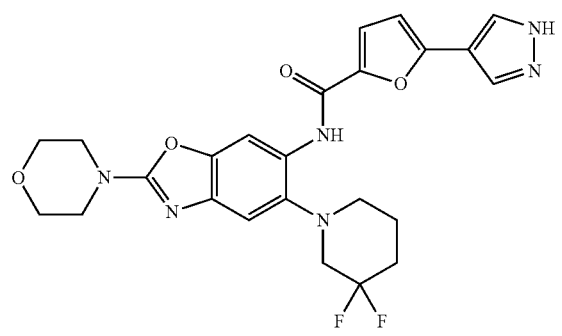 [SMILES: O=C(Nc1cc2oc(N3CCOCC3)nc2cc1N1CCCC(F)(F)C1)c1ccc(-c2cn[nH]c2)o1]
I-42
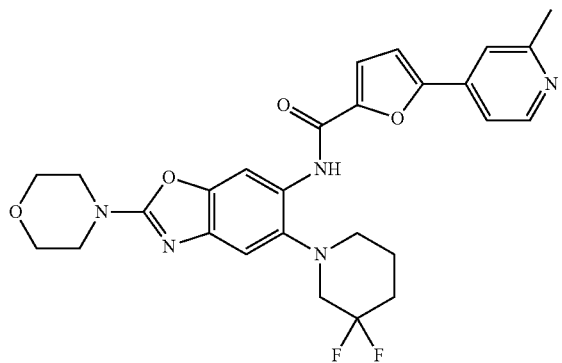 [SMILES: Cc1cc(-c2ccc(C(=O)Nc3cc4oc(N5CCOCC5)nc4cc3N3CCCC(F)(F)C3)o2)ccn1]
I-43
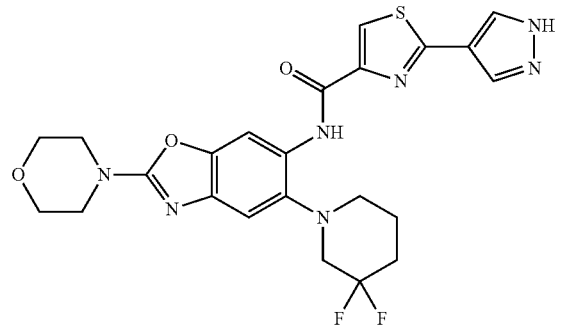 [SMILES: O=C(Nc1cc2oc(N3CCOCC3)nc2cc1N1CCCC(F)(F)C1)c1csc(-c2cn[nH]c2)n1]
I-44

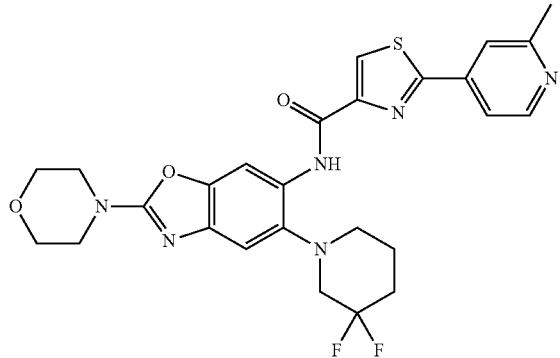 [SMILES: Cc1cc(-c2nc(C(=O)Nc3cc4oc(N5CCOCC5)nc4cc3N3CCCC(F)(F)C3)cs2)ccn1]
I-45
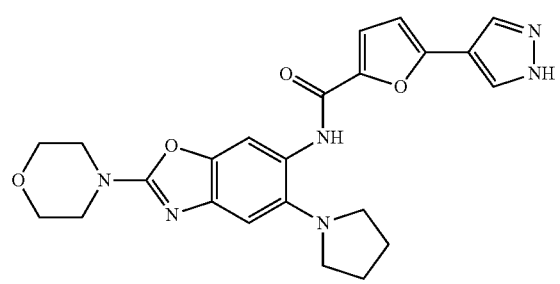 [SMILES: O=C(Nc1cc2oc(N3CCOCC3)nc2cc1N1CCCC1)c1ccc(-c2cn[nH]c2)o1]
I-46
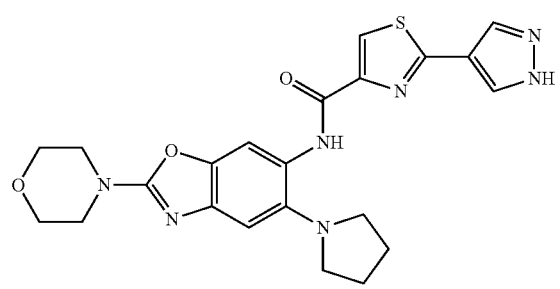 [SMILES: O=C(Nc1cc2oc(N3CCOCC3)nc2cc1N1CCCC1)c1csc(-c2cn[nH]c2)n1]
I-47
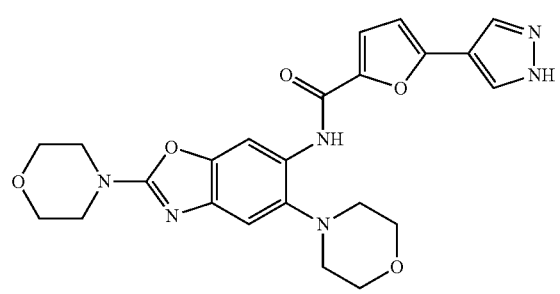 [SMILES: O=C(Nc1cc2oc(N3CCOCC3)nc2cc1N1CCOCC1)c1ccc(-c2cn[nH]c2)o1]
I-48
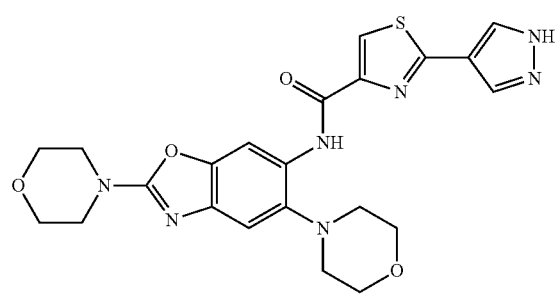 [SMILES: O=C(Nc1cc2oc(N3CCOCC3)nc2cc1N1CCOCC1)c1csc(-c2cn[nH]c2)n1]
I-49

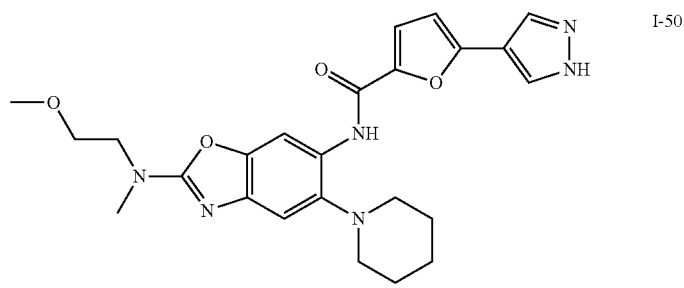
I-50
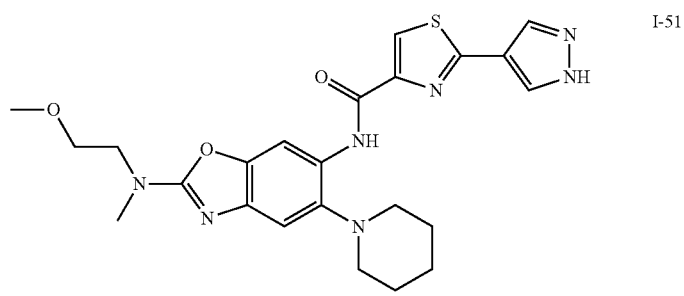
I-51
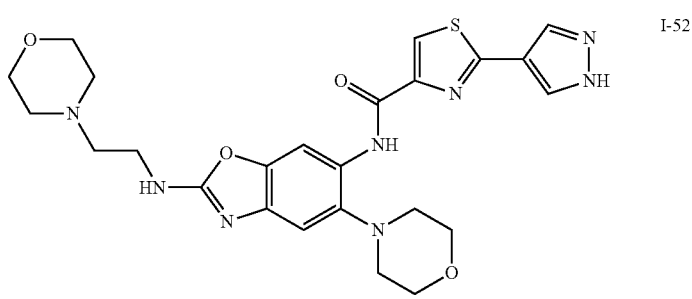
I-52
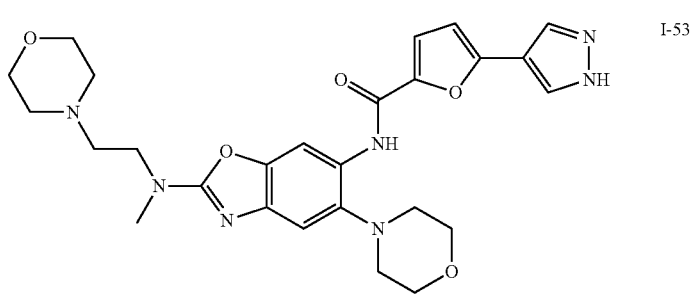
I-53
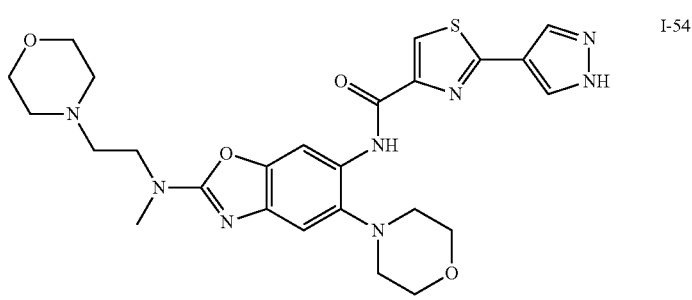
I-54

-continued

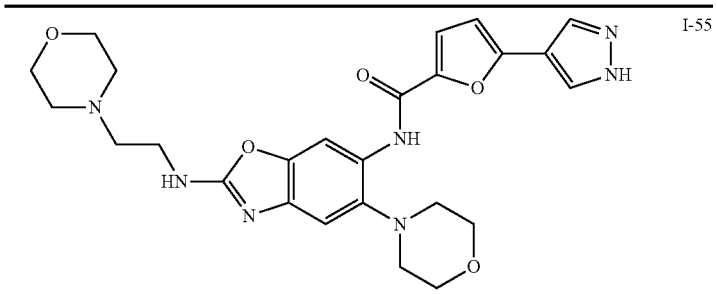

I-55

Exemplary compounds according to formula I include, without limitation, the compounds listed below and pharmaceutically acceptable salts thereof:

I-1: 5-(6-aminopyridin-3-yl)-N-(2-morpholino-5-(piperidin-1-yl)benzo[d]oxazol-6-yl)furan-2-carboxamide;
I-2: N-(2-morpholino-5-(piperidin-1-yl)benzo[d]oxazol-6-yl)-5-(1H-pyrrolo[2,3-b]pyridin-5-yl)furan-2-carboxamide;
I-3: N-(2-morpholino-5-(piperidin-1-yl)benzo[d]oxazol-6-yl)-5-(1H-pyrazol-4-yl)furan-2-carboxamide;
I-4: N-(2-morpholino-5-(piperidin-1-yl)benzo[d]oxazol-6-yl)-5-(1H-pyrazol-3-yl)furan-2-carboxamide;
I-5: 5-(6-aminopyridin-3-yl)-N-(2-morpholino-5-(piperidin-1-yl)benzo[d]thiazol-6-yl)furan-2-carboxamide;
I-6: N-(2-morpholino-5-(piperidin-1-yl)benzo[d]thiazol-6-yl)-5-(1H-pyrrolo[2,3-b]pyridin-5-yl)furan-2-carboxamide;
I-7: N-(2-morpholino-5-(piperidin-1-yl)benzo[d]thiazol-6-yl)-5-(1H-pyrazol-4-yl)furan-2-carboxamide;
I-8: N-(2-morpholino-5-(piperidin-1-yl)benzo[d]thiazol-6-yl)-5-(1H-pyrazol-3-yl)furan-2-carboxamide;
I-9: 5-(2-methylpyridin-4-yl)-N-(2-morpholino-5-(piperidin-1-yl)benzo[d]thiazol-6-yl)furan-2-carboxamide;
I-10: 5-(2-methylpyridin-4-yl)-N-(2-morpholino-5-(piperidin-1-yl)benzo[d]oxazol-6-yl)furan-2-carboxamide;
I-11: 2-(6-aminopyridin-3-yl)-N-(2-morpholino-5-(piperidin-1-yl)benzo[d]oxazol-6-yl)thiazole-4-carboxamide;
I-12: N-(2-morpholino-5-(piperidin-1-yl)benzo[d]oxazol-6-yl)-2-(1H-pyrazol-4-yl)thiazole-4-carboxamide;
I-13: N-(2-morpholino-5-(piperidin-1-yl)benzo[d]oxazol-6-yl)-2-(1H-pyrazol-3-yl)thiazole-4-carboxamide;
I-14: 2-(2-methylpyridin-4-yl)-N-(2-morpholino-5-(piperidin-1-yl)benzo[d]oxazol-6-yl)thiazole-4-carboxamide;
I-15: 5-(6-aminopyridin-3-yl)-N-(2-(4-methylpiperazin-1-yl)-5-(piperidin-1-yl)benzo[d]oxazol-6-yl)furan-2-carboxamide;
I-16: N-(2-(4-methylpiperazin-1-yl)-5-(piperidin-1-yl)benzo[d]oxazol-6-yl)-5-(1H-pyrazol-4-yl)furan-2-carboxamide;
I-17: N-(2-(4-methylpiperazin-1-yl)-5-(piperidin-1-yl)benzo[d]oxazol-6-yl)-5-(1H-pyrazol-3-yl)furan-2-carboxamide;
I-18: N-(2-(4-methylpiperazin-1-yl)-5-(piperidin-1-yl)benzo[d]oxazol-6-yl)-5-(2-methylpyridin-4-yl)furan-2-carboxamide;
I-19: 2-(6-aminopyridin-3-yl)-N-(2-(4-methylpiperazin-1-yl)-5-(piperidin-1-yl)benzo[d]oxazol-6-yl)thiazole-4-carboxamide;
I-20: N-(2-(4-methylpiperazin-1-yl)-5-(piperidin-1-yl)benzo[d]oxazol-6-yl)-2-(1H-pyrazol-4-yl)thiazole-4-carboxamide;
I-21: N-(2-(4-methylpiperazin-1-yl)-5-(piperidin-1-yl)benzo[d]oxazol-6-yl)-2-(1H-pyrazol-3-yl)thiazole-4-carboxamide;
I-22: N-(2-(4-methylpiperazin-1-yl)-5-(piperidin-1-yl)benzo[d]oxazol-6-yl)-2-(2-methylpyridin-4-yl)thiazole-4-carboxamide;
I-23: N-(5-(4-fluoropiperidin-1-yl)-2-morpholinobenzo[d]oxazol-6-yl)-5-(1H-pyrazol-4-yl)furan-2-carboxamide;
I-24: N-(5-(4-fluoropiperidin-1-yl)-2-morpholinobenzo[d]oxazol-6-yl)-5-(2-methylpyridin-4-yl)furan-2-carboxamide;
I-25: N-(5-(4-fluoropiperidin-1-yl)-2-morpholinobenzo[d]oxazol-6-yl)-2-(1H-pyrazol-4-yl)thiazole-4-carboxamide;
I-26: N-(5-(4-fluoropiperidin-1-yl)-2-morpholinobenzo[d]oxazol-6-yl)-2-(2-methylpyridin-4-yl)thiazole-4-carboxamide;
I-27: N-(5-(4,4-difluoropiperidin-1-yl)-2-morpholinobenzo[d]oxazol-6-yl)-5-(1H-pyrazol-4-yl)furan-2-carboxamide;
I-28: N-(5-(4,4-difluoropiperidin-1-yl)-2-morpholinobenzo[d]oxazol-6-yl)-5-(2-methylpyridin-4-yl)furan-2-carboxamide;
I-29: N-(5-(4,4-difluoropiperidin-1-yl)-2-morpholinobenzo[d]oxazol-6-yl)-2-(1H-pyrazol-4-yl)thiazole-4-carboxamide;
I-30: N-(5-(4,4-difluoropiperidin-1-yl)-2-morpholinobenzo[d]oxazol-6-yl)-2-(2-methylpyridin-4-yl)thiazole-4-carboxamide;
I-31: N-(2,5-di(piperidin-1-yl)benzo[d]oxazol-6-yl)-5-(1H-pyrazol-4-yl)furan-2-carboxamide;
I-32: N-(2,5-di(piperidin-1-yl)benzo[d]oxazol-6-yl)-5-(1H-pyrazol-3-yl)furan-2-carboxamide;
I-33: N-(2,5-di(piperidin-1-yl)benzo[d]oxazol-6-yl)-5-(2-methylpyridin-4-yl)furan-2-carboxamide;
I-34: 2-(6-aminopyridin-3-yl)-N-(2,5-di(piperidin-1-yl)benzo[d]oxazol-6-yl)thiazole-4-carboxamide;
I-35: N-(2,5-di(piperidin-1-yl)benzo[d]oxazol-6-yl)-2-(1H-pyrazol-4-yl)thiazole-4-carboxamide;
I-36: N-(2,5-di(piperidin-1-yl)benzo[d]oxazol-6-yl)-2-(1H-pyrazol-3-yl)thiazole-4-carboxamide;
I-37: N-(2,5-di(piperidin-1-yl)benzo[d]oxazol-6-yl)-2-(2-methylpyridin-4-yl)thiazole-4-carboxamide;
I-38: N-(5-(3-fluoropiperidin-1-yl)-2-morpholinobenzo[d]oxazol-6-yl)-5-(1H-pyrazol-4-yl)furan-2-carboxamide;
I-39: N-(5-(3-fluoropiperidin-1-yl)-2-morpholinobenzo[d]oxazol-6-yl)-5-(2-methylpyridin-4-yl)furan-2-carboxamide;
I-40: N-(5-(3-fluoropiperidin-1-yl)-2-morpholinobenzo[d]oxazol-6-yl)-2-(1H-pyrazol-4-yl)thiazole-4-carboxamide;

I-41: N-(5-(3-fluoropiperidin-1-yl)-2-morpholinobenzo[d]oxazol-6-yl)-2-(2-methylpyridin-4-yl)thiazole-4-carboxamide;
I-42: N-(5-(3,3-difluoropiperidin-1-yl)-2-morpholinobenzo[d]oxazol-6-yl)-5-(1H-pyrazol-4-yl)furan-2-carboxamide;
I-43: N-(5-(3,3-difluoropiperidin-1-yl)-2-morpholinobenzo[d]oxazol-6-yl)-5-(2-methylpyridin-4-yl)furan-2-carboxamide;
I-44: N-(5-(3,3-difluoropiperidin-1-yl)-2-morpholinobenzo[d]oxazol-6-yl)-2-(1H-pyrazol-4-yl)thiazole-4-carboxamide;
I-45: N-(5-(3,3-difluoropiperidin-1-yl)-2-morpholinobenzo[d]oxazol-6-yl)-2-(2-methylpyridin-4-yl)thiazole-4-carboxamide;
I-46: N-(2-morpholino-5-(pyrrolidin-1-yl)benzo[d]oxazol-6-yl)-5-(1H-pyrazol-4-yl)furan-2-carboxamide;
I-47: N-(2-morpholino-5-(pyrrolidin-1-yl)benzo[d]oxazol-6-yl)-2-(1H-pyrazol-4-yl)thiazole-4-carboxamide;
I-48: N-(2,5-dimorpholinobenzo[d]oxazol-6-yl)-5-(1H-pyrazol-4-yl)furan-2-carboxamide;
I-49: N-(2,5-dimorpholinobenzo[d]oxazol-6-yl)-2-(1H-pyrazol-4-yl)thiazole-4-carboxamide;
I-50: N-(2-((2-methoxyethyl)(methyl)amino)-5-(piperidin-1-yl)benzo[d]oxazol-6-yl)-5-(1H-pyrazol-4-yl)furan-2-carboxamide;
I-51: N-(2-((2-methoxyethyl)(methyl)amino)-5-(piperidin-1-yl)benzo[d]oxazol-6-yl)-2-(1H-pyrazol-4-yl)thiazole-4-carboxamide;
I-52: N-(2-((2-morpholinoethyl)amino)-5-(piperidin-1-yl)benzo[d]oxazol-6-yl)-2-(1H-pyrazol-4-yl)thiazole-4-carboxamide;
I-53: N-(2-(methyl(2-morpholinoethyl)amino)-5-(piperidin-1-yl)benzo[d]oxazol-6-yl)-5-(1H-pyrazol-4-yl)furan-2-carboxamide;
I-54: N-(2-(methyl(2-morpholinoethyl)amino)-5-(piperidin-1-yl)benzo[d]oxazol-6-yl)-2-(1H-pyrazol-4-yl)thiazole-4-carboxamide; or
I-55: N-(2-((2-morpholinoethyl)amino)-5-(piperidin-1-yl)benzo[d]oxazol-6-yl)-5-(1H-pyrazol-4-yl)furan-2-carboxamide.

B. Synthesis

Disclosed benzazole compounds can be prepared as exemplified below, and as will be understood by a person of ordinary skill in the art in organic synthesis. An exemplary synthesis may include the following first reaction step according to Scheme 1:

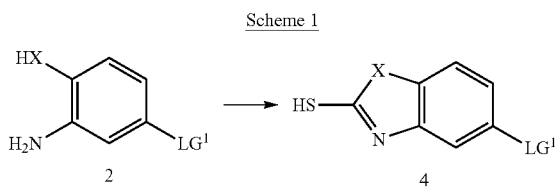

Aniline 2 is reacted with CS$_2$ in the presence of a base to form benzazole 4. X is typically oxygen or sulfur, and LG$^1$ is a leaving group. Suitable leaving groups include, but are not limited to, fluoride, chloride, bromide, iodide, mesylate or tosylate. The reaction is performed in a suitable solvent, such as a polar solvent. Suitable solvents include, but are not limited to, alcohols, such as methanol, ethanol, propanol, isopropanol or combinations thereof. The base can be any base that facilitates the reaction. Exemplary bases include, but are not limited to, hydroxides, particularly metal hydroxides, such as potassium hydroxide, sodium hydroxide, and lithium hydroxide. The reaction is performed at a temperature suitable to facilitate the reaction. A suitable reaction is typically from 50° C. to 100° C.

A second reaction step in the exemplary synthesis is provided below according to Scheme 2:

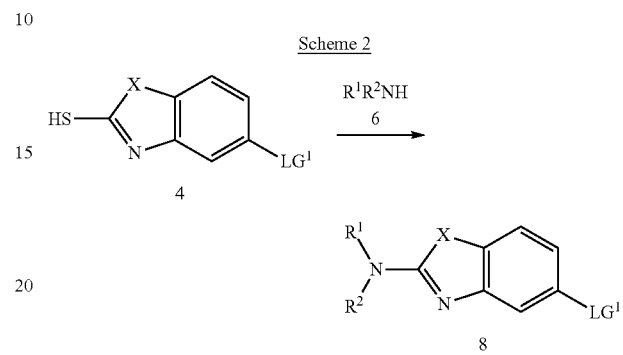

Benzazole 4 is reacted with amine 6 to form compound 8. The reaction is performed in a solvent suitable to facilitate the reaction. Suitable solvents include aprotic solvents, such as dioxane. The reaction is typically heated to a temperature suitable to facilitate the reaction, such as from 60° C. to 100° C.

A third reaction step in the exemplary synthesis is provided below according to Scheme 3:

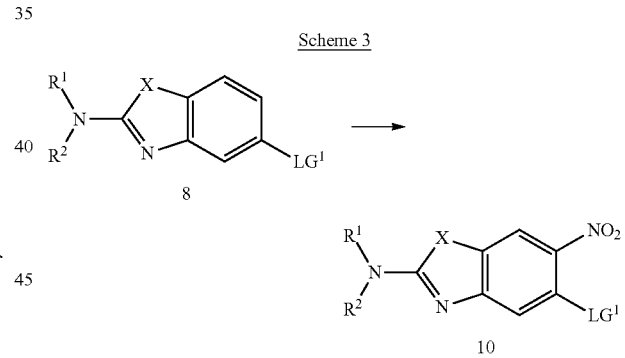

Compound 8 is reacted with a nitrating agent and/or mixture to form compound 10. Suitable nitrating agents and/or mixtures include, but are not limited to, nitric acid such as fuming nitric acid, fuming nitric acid/sulfuric acid or nitric acid/acetic anhydride.

A fourth reaction step in the exemplary synthesis is provided below according to Scheme 4:

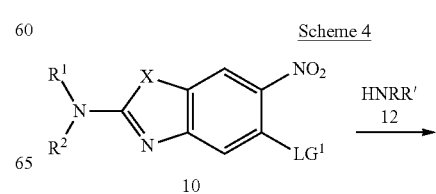

-continued

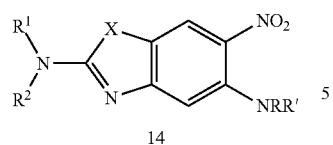
14

Compound 10 is reacted with amine 12 to form compound 14. The reaction is performed in a solvent suitable to facilitate the reaction. Suitable solvents include aprotic solvents, such as dioxane or acetonitrile. The reaction may be performed in the presence of a base, such as potassium carbonate, sodium carbonate, triethylamine or diisopropylethylamine (DIEA). Alternatively, excess amine may be used as the base, such as by using two or more molar equivalents of amine 12 in the reaction. The reaction is typically heated to a temperature suitable to facilitate the reaction, such as from 75° C. to 120° C.

A fifth reaction step in the exemplary synthesis is provided below according to Scheme 5:

Scheme 5

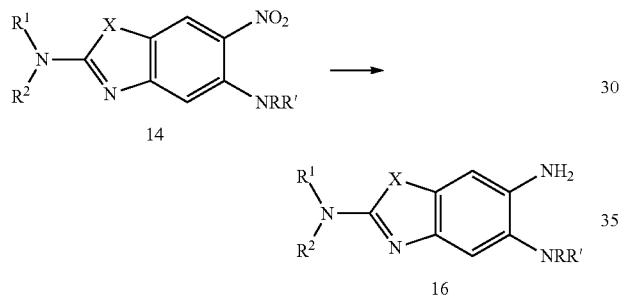

The nitro-functional group on compound 14 is reduced to form compound 16. Any suitable reducing agent can be used, such as $H_2$/palladium on carbon, $H_2$/platinum (IV) oxide, $H_2$/Raney nickel, Fe/HCl, Fe/acetic acid, zinc/acid, zinc/ammonium chloride, or tin chloride. The reaction is performed in a suitable solvent, such as alcohol, including methanol, ethanol, propanol, or isopropanol; acetic acid; water; or a combination thereof. A person of ordinary skill in the art will appreciate that compound 16 may form as a free base or a salt, such as an HCl salt or acetic acid salt, depending on the method used to reduce the nitro group.

A sixth reaction step in the exemplary synthesis is provided below according to Scheme 6:

Scheme 6

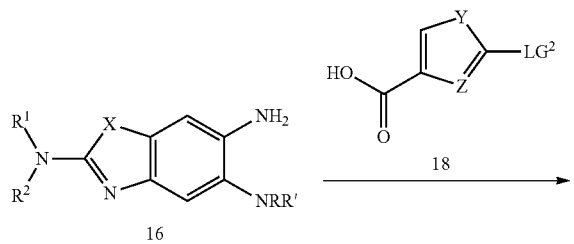

-continued

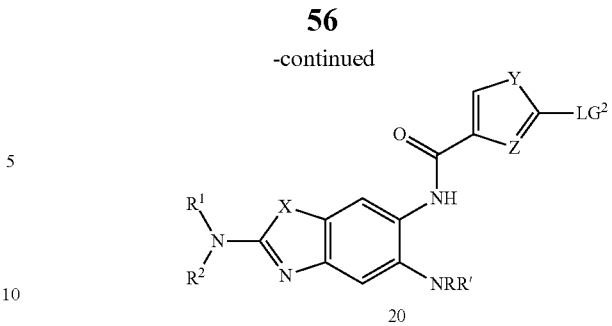
20

Compound 16 is reacted with carboxylic acid 18 to form compound 20. Y is oxygen or sulfur and Z is nitrogen or CR, where R is typically H or aliphatic. The carboxylic acid 18 is activated by any suitable method and then reacted with the amine on compound 16. Suitable activation methods include, but are not limited to: forming the acid chloride by treatment with thionyl chloride; by treatment with 1-[Bis(dimethylamino)methylene]-1H-1,2,3-triazolo[4,5-b]pyridinium 3-oxid hexafluorophosphate (HATU) and a base such as diisopropylethylamine (DIEA); by treatment with carbonyldiimidazole (CDI); or by treatment with a carbodiimide, such as dicyclohexylcarbodiimide (DCC) or 1-Ethyl-3-(3-dimethylaminopropyl)carbodiimide (EDC). The reaction is performed in a solvent suitable to facilitate the reaction. Suitable solvents include, but are not limited to, chloroform, dichloromethane, dioxane, toluene, acetonitrile, DMF, tetrahydrofuran, or a combination thereof.

A seventh reaction step in the exemplary synthesis is provided below according to Scheme 7:

Scheme 7

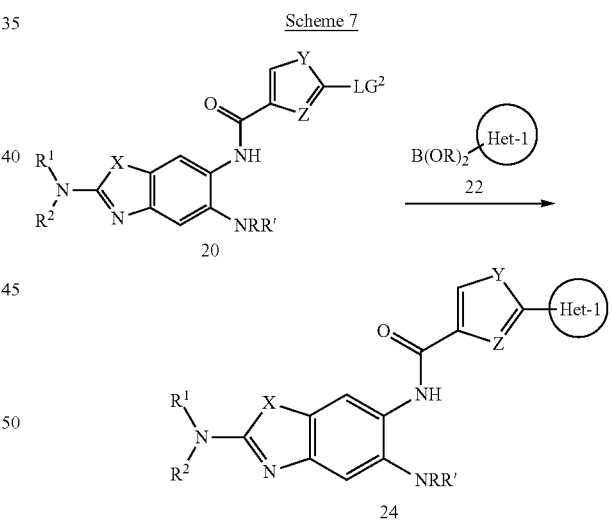

Compound 20 is coupled with compound 22 to form compound 24 using any coupling reaction suitable to form a bond between two rings. In the example above, a boronic acid coupling is shown, where the leaving group $LG^2$ on compound 20 is halo, such as bromo or iodo. Other suitable coupling functional groups include trialkyl tin or boronic esters, such as a boronic acid pinacol ester. The coupling reaction typically proceeds in the presence of a suitable catalyst. For a boronic acid coupling, the catalyst typically is a palladium catalyst, such as $PdCl_2(dppf)_2$, palladium acetate and triphenyl phosphine, or tetrakis(triphenylphosphine)palladium(O). The reaction is performed in the presence of a base, such as metal carbonates, including sodium, potassium or cesium carbonate, and is performed in a suitable solvent or solvent mixture, such as dioxane/water or DME/ethanol/water. The reaction may be heated at a suitable temperature, such as from 50° C. to 140° C., typically about 120° C., and/or agitated for a suitable period of time, such as from 1 hour to 3 days, from 6 hours to 24 hours, or from 12 hours to 18 hours, to facilitate the reaction proceeding to completion. The reaction may be performed in a microwave, which typically reduces the reaction time. Compound 24 is then isolated from the reaction mixture and purified by a suitable technique.

C. Additional Therapeutic Agents for Combination

The compounds of the present invention may be used alone, in combination with one another, or as an adjunct to, or in combination with, other established therapies. In another aspect, the compounds of the present invention may be used in combination with other therapeutic agents useful for the disorder or condition being treated. These compounds may be administered simultaneously or sequentially in any order. The compounds may be administered within a time period such that a subject experiences an overlapping beneficial effect from both the benzazole compound and the additional therapeutic agent(s). The benzazole compound and the additional therapeutic agent(s) may be administered by the same route of administration, or by a different route. It is specifically intended that the present compounds be administered in combination with one or more additional therapeutic agents, including in combination with one or more agents described in this section.

In some embodiments, the second therapeutic agent is an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with other anti-cancer or cytotoxic agents. Various classes of anti-cancer and anti-neoplastic compounds for use with the presently disclosed inhibitors include, but are not limited to, alkylating agents, antimetabolites, vinca alkyloids, taxanes, antibiotics, enzymes, cytokines, platinum coordination complexes, substituted ureas, kinase inhibitors, hormones and hormone antagonists and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an anti-neoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesteron caproate, medroxyprogesterone; and anti-estrogen compound tamoxifen.

Other chemotherapeutic agents for combination include immunooncology agents, such as anti-PD-1 and/or anti-PD-L1 antibodies, such as nivolumab, pembrolizumab, lambrolizumab, pidilizumab, BMS-936559, MPDL3280A, AMP-224 or MEDI4736; anti-CTLA-4 antibodies, such as ipilimumab or tremelimumab; anti-KIR antibodies, such as lirilumab; anti-LAG3 antibodies, such as BMS-986016; anti-CD137 antibodies, such as urelumab; anti-SLAM antibodies, such as anti-SLAMF7 for example elotuzumab; PI3K inhibitors, such as idelalisib, AZD8186, INCB40093 and INCB50465; and indole dioxygenase (IDO) and/or tryptophan dioxygenase inhibitors (TDO), such as 1-methyltryptophan, indoximod, NSC 36398 (dihydroquercetin, taxifolin), NLG919, INCB024360 (epacodostat), and F001287. In particular embodiments, two or more immunooncology agents are combined with a disclosed benzazole compound. Typically, the immunooncology agents in such combinations act on different targets. For example, the combination of an anti-PD-1 agent, such as nivolumab with an anti-CTLA-4 agent, such as ipilimumab, is particularly useful in combination with a benzazole compound.

In some embodiments, the benzazole compound may be used in combination with an immunooncology agent and/or with other anti-cancer or cytotoxic agents. In particular embodiments, the present compounds are combined with an immunooncology agent and are further combined with one or more agents from the current standard of care for a given malignancy. The following table displays exemplary cancers treatable in the combination therapies comprising the presently disclosed benzazole compounds and lists additional treatments for use in combination with the benzazole compounds and immunooncology agent disclosed herein:

| Cancer | Drug or Treatment |
| --- | --- |
| Glioma | lomustine, temozolide and/or radiation |
| hepatocellular carcinoma | sorafenib, regorafenib |
| myelodysplastic syndromes | decitabine or azacytidine |
| pancreatic cancer | Gemcitabine |
| ovarian cancer, such as epithelial ovarian carcinoma | carboplatin, cisplatin, doxorubicin, gemcitabine, paclitaxel |
| breast cancer | Trastuzumab |
| basal and squamous skin carcinomas | 5-fluorouracil, imiquimod, photodynamic therapy (e.g. with 5-aminolevulinic acid), |
| head and neck carcinoma | bleomycin, cisplatin, cetuximab, docetaxel, fluorouracil, methotrexate |
| triple negative breast cancer | Paclitaxel |
| Prostate | abiraterone, enzalutamide |

These and other useful anti-cancer compounds are described in Merck Index, 13th Ed. (O'Neil M. J. et al., ed) Merck Publishing Group (2001) and Goodman and Gilmans The Pharmacological Basis of Therapeutics, 10th Edition, Hardman, J. G. and Limbird, L. E. eds., pg. 1381-1287, McGraw Hill, (1996), both of which are incorporated by reference herein.

Among the CTLA 4 antibodies that can be used in combination with the presently disclosed inhibitors is ipilimumab, marketed as YERVOY® by Bristol-Myers Squibb.

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

In particular embodiments, including the treatment of leukemias, including CLL, mantle cell lymphoma and ALL, the presently disclosed compounds are used in combination with a B-cell lymphoma 2 (BCL2) inhibitor, such as ABT-199 or ABT737.

Examples of kinase inhibitors that are useful in combination with the presently disclosed compounds, particularly in treating malignancies include, Btk inhibitors, such as ibrutinib; CDK inhibitors, such as palbociclib; EGFR inhibitors, such as afatinib, erlotinib, gefitinib, lapatinib and vandetinib; Mek inhibitors, such as trametinib; Raf inhibitors, such as dabrafenib, sorafenib and vemurafenib; VEGFR inhibitors, such as axitinib, lenvatinib, nintedanib, and pazopanib; BCR-Abl inhibitors, such as bosutinib, dasatinib, imatinib and nilotinib; PI3-kinase inhibitors, such as idelalisib; Syk inhibitors, such as fostamatinib; and JAK inhibitors, such as baricitinib, ruxolitinib and tofacitinib. In other embodiments, the second or additional therapeutic agent or agents for combination with the presently disclosed inhibitors may be selected from any of the following:

analgesics—morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics—aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides) e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicilllins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies—anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab;

anticoagulants—warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents—steroids, e.g., budesonide, nonsteroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants—mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase—C receptor agonists or intestinal secretagogues, for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

D. Compositions Comprising Benzazole Compounds

The disclosed benzazole compounds may be used alone, in any combination, and in combination with, or adjunctive to, at least one second therapeutic agent, and further the benzazole compounds, and the at least one second therapeutic, may be used in combination with any suitable additive useful for forming compositions for administration to a subject. Additives can be included in pharmaceutical compositions for a variety of purposes, such as to dilute a composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. Typical additives include, by way of example and without limitation: pharmaceutically acceptable excipients; pharmaceutically acceptable carriers; and/or adjuvants, such as mono-, di-, and polysaccharides, sugar alcohols and other polyols, such as, lactose, glucose, raffinose, melezitose, lactitol, maltitol, trehalose, sucrose, mannitol, starch, or combinations thereof; surfactants, such as sorbitols, diphosphatidyl choline, and lecithin; bulking agents; buffers, such as phosphate and citrate buffers; anti-adherents, such as magnesium stearate; binders, such as saccharides (including disaccharides, such as sucrose and lactose), polysaccharides (such as starches, cellulose, microcrystalline cellulose, cellulose ethers (such as hydroxypropyl cellulose), gelatin, synthetic polymers (such as polyvinylpyrrolidone, polyalkylene gylcols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

III. Methods of Use

A. Diseases/Disorders

The disclosed benzazole compounds, as well as combinations and/or compositions thereof, may be used to ameliorate, treat or prevent a variety of diseases and/or disorders. In particular embodiments, the benzazole compound, combinations of benzazole compounds, or compositions thereof, may be used to treat or prevent auto-immune diseases, inflammatory disorders, cardiovascular diseases, nerve disorders, neurodegenerative disorders, allergic disorders, asthma, pancreatitis, multi-organ failure, kidney diseases, platelet aggregation, cancer, transplantation, sperm motility, erythrocyte deficiency, graft rejection, lung injuries, respiratory diseases, ischemic conditions, bacterial infections and/or viral infections.

In some embodiments, the benzazole compound, combinations of benzazole compounds, or compositions thereof, may be used to treat or prevent allergic diseases, amyotrophic lateral sclerosis (ALS), systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy or asthma.

The benzazole compound, combinations of benzazole compounds, or compositions thereof, may also be useful for ameliorating, treating or preventing immune regulatory disorders related to bone marrow or organ transplant rejection or graft-versus-host disease. Examples of inflammatory and immune regulatory disorders that can be treated with the present compounds include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjögren's syndrome, adiposis, eosinophilic fasciitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, non-alcoholic steatohepatitis (NASH), hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, or chronic bacterial infection.

In certain embodiments the present compounds are useful for treating nerve disorders. For example, the present compounds can be used to treat nerve pain, including neuropathic pain and inflammation induced pain.

In certain embodiments, the benzazole compound, combinations of benzazole compounds, or compositions thereof, are useful for treating and/or preventing alcoholic liver disease (steatohepatitis), rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (including Crohn's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, pseudogout, sapho syndrome, Castleman's disease, sepsis, stroke, atherosclerosis, celiac disease, DIRA (deficiency of Il-1 receptor antagonist), Alzheimer's disease, Parkinson's disease.

Proliferative diseases that may be treated by the benzazole compound, combinations of benzazole compounds, or compositions thereof, include benign or malignant tumors, solid tumors and liquid tumors, including carcinoma of the brain, kidney, liver, adrenal gland, bladder, breast, head and neck, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), pleural effusion lymphoma, smoldering or indolent multiple myeloma, or hematological malignancies (including leukemia, DLBCL, ABC DLBCL, chronic lymphocytic leukemia (CLL), chronic lymphocytic lymphoma, primary effusion lymphoma, Burkitt lymphoma/leukemia, acute lymphocytic leukemia (ALL), B-cell prolymphocytic leukemia, lymphoplasmacytic lymphoma, myelodysplastic syndrome, myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors, those resistant to IRAK inhibitors, ibrutinib resistant malignancies, including ibrutinib resistant hematological malignancies, such as ibrutinib resistant CLL and ibrutinib resistant Waldenström's macroglobulinemia.

Examples of allergic disorders that may be treated using the benzazole compound, combinations of benzazole compounds, or compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, post-nasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The benzazole compound, combinations of benzazole compounds, or compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

B. Formulations and Administration

Pharmaceutical compositions comprising the disclosed compounds (or prodrugs thereof) may be manufactured by conventional mixing, dissolving, granulating, dragee-making, levigating, emulsifying, encapsulating, entrapping or lyophilization processes. The compositions may be formulated in conventional manner using one or more physiologically acceptable excipients, diluents, carriers, adjuvants or auxiliaries to provide preparations which can be used pharmaceutically.

The active compound or prodrug may be formulated in the pharmaceutical compositions per se, or in the form of a hydrate, solvate, N-oxide or pharmaceutically acceptable salt. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s), hydrate, solvate, N-oxide or pharmaceutically acceptable salt or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases, such as cocoa butter or other glycerides.

For nasal administration or administration by inhalation or insufflation, the active compound(s), hydrate, solvate, N-oxide, pharmaceutically acceptable salt or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5 20 mg/ml); benzalkonium chloride (0.1 0.2 mg/mL); polysorbate 80 (TWEEN® 80; 0.5 5 mg/ml); carboxymethylcellulose sodium or microcrystalline cellulose (115 mg/ml); phenylethanol (14 mg/ml); and dextrose (20 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL compound or prodrug, 1% (v/v) Polysorbate 80 (TWEEN® 80), 50 mM citrate and/or 0.9% sodium chloride.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, which are incorporated herein by reference.

For prolonged delivery, the active compound(s) or prodrug(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, which are incorporated herein by reference.

Alternatively, other pharmaceutical delivery systems may be employed. Liposomes and emulsions are well-known examples of delivery vehicles that may be used to deliver active compound(s) or prodrug(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

C. Dosages

The benzazole compound or combinations of benzazole compounds will generally be used in an amount effective to achieve the intended result, for example, in an amount effective to treat or prevent a particular condition. The benzazole compound(s), or compositions thereof, can be administered therapeutically to achieve therapeutic benefit or prophylactically to achieve prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of benzazole compounds will also depend on various factors, including the age, weight, general health, and severity of the condition of the patient or subject being treated. Dosage may also need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, and respiratory infections. Dosage, and frequency of administration of the benzazole compound(s) or compositions thereof, will also depend on whether the benzazole compound(s) are formulated for treatment of acute episodes of a condition or for the prophylactic treatment of a disorder. A person or ordinary skill in the art will be able to determine the optimal dose for a particular individual.

For prophylactic administration, the benzazole compound, combinations of benzazole compounds, or compositions thereof, can be administered to a patient or subject at risk of developing one of the previously described conditions. For example, if it is unknown whether a patient or subject is allergic to a particular drug, the benzazole compound, combinations of benzazole compounds, or compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, a benzazole compound(s), or composition thereof, can be administered to an allergy sufferer prior to expected exposure to the allergen. A benzazole compound, combinations of benzazole compounds, or compositions thereof, can also be administered prophylactically to healthy individuals who are repeatedly exposed to agents known to one of the above-described maladies to prevent the onset of the disorder. For example, a benzazole compound, combinations of benzazole compounds, or compositions thereof, can be administered to a healthy individual who is repeatedly exposed to an allergen known to induce allergies, such as latex, in an effort to prevent the individual from developing an allergy. Alternatively, a benzazole compound, combinations of benzazole compounds, or compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ from greater than 0 to 20 µM, such as from greater than 0 to 10 µM, from greater than 0 to 5 µM, from greater than 0 to 1 µM, from greater than 0 to 0.5 µM, or from greater than 0 to 0.1 µM.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

Dosage amounts of disclosed benzazole compounds will typically be in the range of from greater than 0 mg/kg/day, such as 0.0001 mg/kg/day or 0.001 mg/kg/day or 0.01 mg/kg/day, up to at least 100 mg/kg/day. More typically, the dosage (or effective amount) may range from 0.0025 mg/kg to about 1 mg/kg administered at least once per day, such as from 0.01 mg/kg to 0.5 mg/kg or from 0.05 mg/kg to 0.15 mg/kg. The total daily dosage typically ranges from 0.1 mg/kg to 5 mg/kg or to 20 mg/kg per day, such as from 0.5 mg/kg to 10 mg/kg per day or from 0.7 mg/kg per day to 2.5 mg/kg/day. Dosage amounts can be higher or lower depending upon, among other factors, the activity of the benzazole compound, its bioavailability, the mode of administration, and various factors discussed above.

Dosage amount and dosage interval can be adjusted for individuals to provide plasma levels of the benzazole compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Compositions comprising one or more of the disclosed benzazole compounds typically comprise from greater than 0 up to 99% of the benzazole compound, or compounds, and/or other therapeutic agent by total weight percent. More typically, compositions comprising one or more of the disclosed benzazole compounds comprise from 1 to 20 total weight percent of the benzazole compound and other therapeutic agent, and from 80 to 99 weight percent of a pharmaceutically acceptable additive.

Preferably, the benzazole compound, combinations of benzazole compounds, or compositions thereof, will provide therapeutic or prophylactic benefit without causing substantial toxicity. Toxicity of the benzazole compound can be determined using standard pharmaceutical procedures. The dose ratio between toxic and therapeutic (or prophylactic) effect is the therapeutic index. Benzazole compounds that exhibit high therapeutic indices are preferred.

IV. Examples

Example 1

Preparation of 5-fluorobenzo[d]oxazole-2-thiol

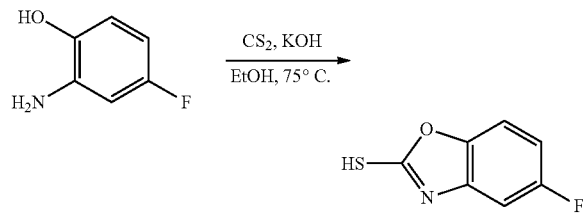

A solution of 2-amino-4-fluorophenol (10 g, 78.8 mmol), carbon disulfide (35 mL), and potassium hydroxide (5.3 g, 94.6 mmol) in ethanol (200 mL) was heated to reflux overnight. The reaction mixture was concentrated to dryness then diluted with water. This solution was neutralized with 1M HCl then washed with ethyl acetate several times. The combined organic phases were washed with brine, dried over $Na_2SO_4$, and concentrated in vacuo giving 9.3 g (70% yield) of the desired 5-fluorobenzo[d]oxazole-2-thiol. $^1$H NMR (300 MHz, DMSO-$d_6$) δ 7.51 (ddd, J=8.8, 4.2, 0.6 Hz, 1H), 7.15-7.04 (m, 2H), 3.31 (br s, 1H). LC-MS (m/z): 170.2.

Example 2

Preparation of 5-fluoro-N-(2-methoxyethyl)-N-methylbenzo[d]oxazol-2-amine

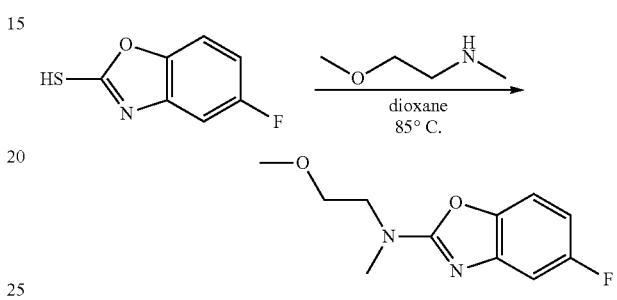

A solution of 5-fluorobenzo[d]oxazole-2-thiol (1.17 g, 6.92 mmol) and (2-methoxyethyl)methylamine (3.7 mL, 34.1 mmol) in dioxane (6 mL) was heated at 85° C. overnight. The reaction was concentrated to dryness and the resulting product, 5-fluoro-N-(2-methoxyethyl)-N-methyl-benzo[d]oxazol-2-amine, was used crude.

Example 3

Preparation of 5-fluoro-N-(2-methoxyethyl)-N-methyl-6-nitrobenzo[d]oxazol-2-amine

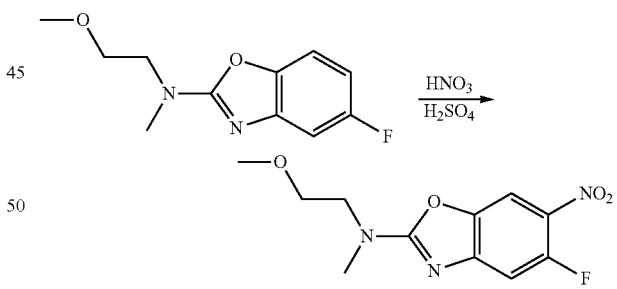

To a solution of 5-fluoro-N-(2-methoxyethyl)-N-methyl-6-nitrobenzo[d]oxazol-2-amine (6.92 mmol) in $H_2SO_4$ (9 mL) cooled in an ice bath was added fuming $HNO_3$ (600 μL) dropwise. The reaction was permitted to warm to room temperature then gently heated at 35° C. overnight. The reaction was complete when monitored by LC-MS and allowed to cool to room temperature. The reaction mixture was then poured over ice and made basic by addition of 4M NaOH to pH 9. The solid formed was filtered and dried giving the desired product N-(2-methoxyethyl)-N-methyl-6-nitro-5-(piperidin-1-yl)benzo[d]oxazol-2-amine (1.25 g, 4.62 mmol) in a 67% yield.

Example 4

Preparation of N-(2-methoxyethyl)-N-methyl-6-nitro-5-(piperidin-1-yl)benzo[d]oxazol-2-amine

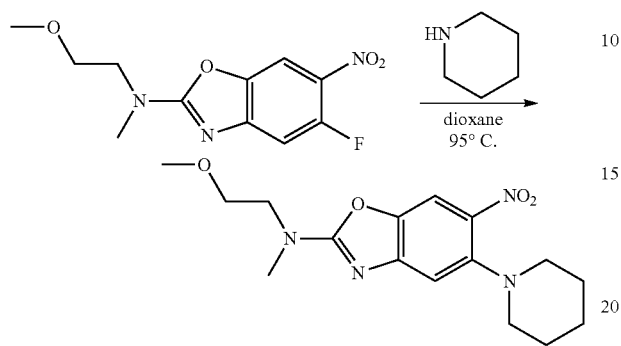

A solution of 5-fluoro-N-(2-methoxyethyl)-N-methyl-6-nitrobenzo[d]oxazol-2-amine (1.24 g, 4.63 mmol), piperidine (915 µL, 9.26 mmol) in dioxane (40 mL) was heated at 95° C. for 5 hours. Upon cooling to room temperature, the reaction was concentrated in vacuo and purified by Si gel chromatography eluting with 0-90% ethyl acetate in hexanes. The desired N-(2-methoxyethyl)-N-methyl-6-nitro-5-(piperidin-1-yl)benzo[d]oxazol-2-amine product eluted at 35% EtOAc/Hex giving 1.22 g (79% yield). LC-MS (m/z): 335.3.

Example 5

Preparation of N2-(2-methoxyethyl)-N2-methyl-5-(piperidin-1-yl)benzo[d]oxazole-2,6-diamine hydrochloride

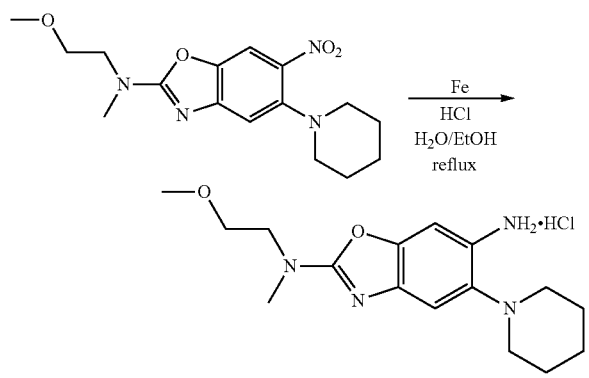

To a solution of N-(2-methoxyethyl)-N-methyl-6-nitro-5-(piperidin-1-yl)benzo[d]oxazol-2-amine (1.22 g, 3.65 mmol) and concentrated hydrochloric acid (600 µL) in water (1 mL) and ethanol (20 mL) was added iron dust (2 g, 36.5 mmol). The mixture was heated to reflux for about 1 hour, when the reaction was complete by LC-MS monitoring. The mixture was filtered through celite, concentrated in vacuo, and used as crude. LC-MS (m/z): 305.7.

Example 6

Preparation of 2-bromo-N-(2-((2-methoxyethyl)(methyl)amino)-5-(piperidin-1-yl)benzo[d]oxazol-6-yl)thiazole-4-carboxamide

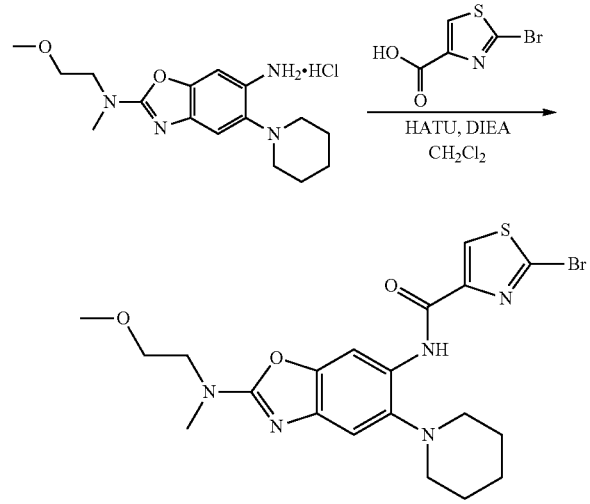

A solution of N2-(2-methoxyethyl)-N2-methyl-5-(piperidin-1-yl)benzo[d]oxazole-2,6-diamine hydrochloride (170 mg, 0.5 mmol), 2-Bromothiazole-4-carboxylic acid (125 mg, 0.6 mmol), and N,N-diisopropylethylamine (435 µL, 2.5 mmol) in $CH_2Cl_2$ (5 mL) was stirred at room temperature overnight. The solution was concentrated in vacuo then diluted with ethyl acetate, washed with water, saturated $NaHCO_3$ solution, and brine. After drying over $Na_2SO_4$, the solution was concentrated in vacuo and purified via Si gel chromatography eluting with 0-100% ethyl acetate in hexanes. The product eluted at 80-100% EtOAc/Hex yielding 2-bromo-N-(2-((2-methoxyethyl)(methyl)amino)-5-(piperidin-1-yl)benzo[d]oxazol-6-yl)thiazole-4-carboxamide (204 mg, 0.413 mmol, 83% yield) as a pale khaki solid. $^1$H NMR (300 MHz, DMSO-$d_6$) δ 10.50 (s, 1H), 8.43 (s, 1H), 8.39 (s, 1H), 7.21 (s, 1H), 3.65 (t, J=5.4 Hz, 2H), 3.56 (t, J=5.4 Hz, 2H), 3.25 (s, 3H), 3.12 (s, 3H), 2.82-2.75 (m, 4H), 1.77 (p, J=6.0 Hz, 4H), 1.63-1.52 (m, 2H). LC-MS (m/z): 494.8.

Example 7

Preparation of N-(2-((2-methoxyethyl)(methyl)amino)-5-(piperidin-1-yl)benzo[d]oxazol-6-yl)-2-(1H-pyrazol-4-yl)thiazole-4-carboxamide (I-51)

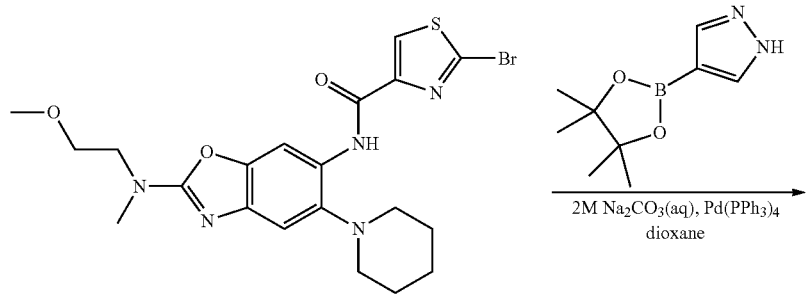

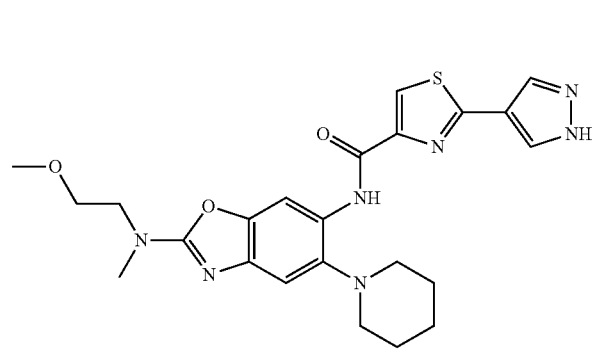

In a microwave vial was prepared a mixture of 2-bromo-N-(2-((2-methoxyethyl)(methyl)amino)-5-(piperidin-1-yl)benzo[d]oxazol-6-yl)thiazole-4-carboxamide (75 mg, 0.15 mmol), pyrazole-4-boronic acid pinacol ester (87 mg, 0.45 mmol), and 2M $Na_2CO_3$ aqueous solution (225 µL, 0.45 mmol) in dioxane (3.5 mL). After purging the vessel under nitrogen gas, tetrakis(triphenylphosphine) palladium (17 mg, 0.015 mmol) and the reaction was heated in a microwave at 120° C. for 1 hour monitoring by LC-MS. The mixture was filtered through celite and the solvent concentrated. The crude reaction mixture was purified by Si gel chromatography eluting with 0-12% 2M $NH_3$/MeOH in $CH_2Cl_2$. This solid was further triturated with EtOAc to yield N-(2-((2-methoxyethyl)(methyl)amino)-5-(piperidin-1-yl)benzo[d]oxazol-6-yl)-2-(1H-pyrazol-4-yl)thiazole-4-carboxamide (38 mg, 0.079 mmol, 53% yield).

$^1$H NMR (300 MHz, DMSO-$d_6$) δ 13.42 (s, 1H), 10.67 (s, 1H), 8.45 (s, 1H), 8.41 (s, 1H), 8.29 (s, 1H), 8.02 (s, 1H), 7.22 (s, 1H), 3.65 (t, J=5.6 Hz, 2H), 3.57 (t, J=5.6 Hz, 2H), 3.25 (s, 3H), 3.13 (s, 3H), 2.85-2.77 (m, 4H), 1.87-1.76 (m, 4H), 1.66-1.55 (m, 2H). LC-MS (m/z): 482.6

Example 8

Compounds I-1 through I-55 were made in a similar manner as Examples 1-7 above. Characterization data for compounds I-1 through I-54 are provided below.

I-1: 5-(6-aminopyridin-3-yl)-N-(2-morpholino-5-(piperidin-1-yl)benzo[d]oxazol-6-yl)furan-2-carboxamide

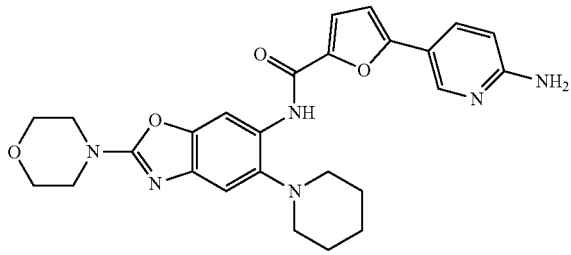 [SMILES: Nc1ccc(-c2ccc(C(=O)Nc3cc4oc(N5CCOCC5)nc4cc3N3CCCCC3)o2)cn1]

$^1$H NMR (300 MHz, DMSO-$d_6$) δ 9.88 (s, 1H), 8.38 (s, 1H), 7.83 (dd, J=8.7, 2.5 Hz, 1H), 7.30 (s, 1H), 7.28 (d, J=3.6 Hz, 1H), 6.91 (d, J=3.6 Hz, 1H), 6.52 (d, J=8.7 Hz, 1H), 6.44 (s, 2H), 3.70 (t, J=4.9 Hz, 4H), 2.80 (t, J=4.9 Hz, 4H), 1.76 (p, J=5.7 Hz, 4H), 1.58 (br s, 2H).

LCMS (m/z): 489.7 (MH$^+$).

I-2: N-(2-morpholino-5-(piperidin-1-yl)benzo[d]oxazol-6-yl)-5-(1H-pyrrolo[2,3-b]pyridin-5-yl)furan-2-carboxamide

¹H NMR (300 MHz, DMSO-d₆) δ 11.94 (s, 1H), 10.03 (s, 1H), 8.82 (d, J=2.1 Hz, 1H), 8.44 (d, J=2.1 Hz, 1H), 8.41 (s, 1H), 7.57 (d, J=3.5 Hz, 1H), 7.35 (d, J=3.6 Hz, 1H), 7.32 (s, 1H), 7.19 (d, J=3.6 Hz, 1H), 6.47 (d, J=3.4 Hz, 1H), 3.75-3.66 (m, 4H), 3.59-3.52 (m, 4H), 2.83 (t, J=5.2 Hz, 4H), 1.83 (p, J=5.8 Hz, 4H), 1.61 (br s, 2H).
LCMS (m/z): 513.8 (MH⁺).

I-3: N-(2-morpholino-5-(piperidin-1-yl)benzo[d]oxazol-6-yl)-5-(1H-pyrazol-4-yl)furan-2-carboxamide

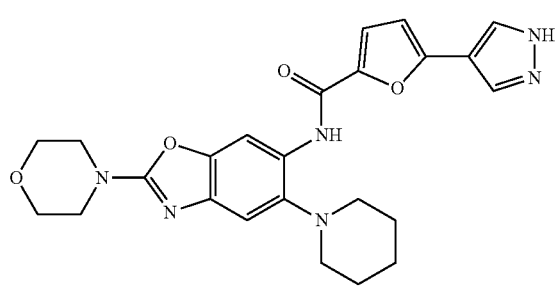 [SMILES: O=C(Nc1cc2oc(N3CCOCC3)nc2cc1N1CCCCC1)c1ccc(-c2cn[nH]c2)o1]

¹H NMR (300 MHz, DMSO-d₆) δ 13.26 (s, 1H), 9.79 (s, 1H), 8.36 (s, 1H), 8.17 (s, 1H), 7.90 (s, 1H), 7.28 (s, 1H), 7.27 (d, J=3.6 Hz, 1H), 6.77 (d, J=3.6 Hz, 1H), 3.73-3.67 (m, 4H), 3.58-3.51 (m, 4H), 2.84-2.77 (m, 4H), 1.77 (p, J=5.8 Hz, 4H), 1.59 (br s, 2H).
LCMS (m/z): 463.7 (MH⁺).

I-4: N-(2-morpholino-5-(piperidin-1-yl)benzo[d]oxazol-6-yl)-5-(1H-pyrazol-3-yl)furan-2-carboxamide

¹H NMR (300 MHz, DMSO-d₆) δ 13.21 (s, 1H), 9.92 (s, 1H), 8.38 (s, 1H), 7.89 (dd, J=2.4, 1.4 Hz, 1H), 7.30 (d, J=3.6 Hz, 1H), 7.29 (s, 1H), 6.91 (d, J=3.6 Hz, 1H), 6.66 (t, J=2.1 Hz, 1H), 3.72-3.68 (m, 4H), 3.57-3.53 (m, 4H), 2.80 (t, J=5.2 Hz, 4H), 1.80 (p, 5.8 Hz, 4H), 1.59 (br s, 2H).
LCMS (m/z): 463.7 (MH⁺).

I-5: 5-(6-aminopyridin-3-yl)-N-(2-morpholino-5-(piperidin-1-yl)benzo[d]thiazol-6-yl)furan-2-carboxamide

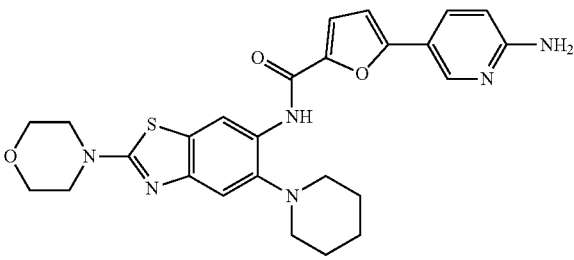 [SMILES: Nc1ccc(-c2ccc(C(=O)Nc3cc4sc(N5CCOCC5)nc4cc3N3CCCCC3)o2)cn1]

¹H NMR (300 MHz, DMSO-d₆) δ 9.74 (s, 1H), 8.64 (s, 1H), 8.50 (d, J=2.5 Hz, 1H), 7.83 (dd, J=8.8, 2.4 Hz, 1H), 7.41 (s, 1H), 7.28 (d, J=3.6 Hz, 1H), 6.91 (d, J=3.6 Hz, 1H), 6.52 (d, J=8.7 Hz, 1H), 6.44 (s, 2H), 3.72 (t, J=4.8 Hz, 4H), 3.50 (t, J=4.8 Hz, 4H), 2.83 (t, J=5.1 Hz, 4H), 1.77 (br s, 4H), 1.58 (br s, 2H).

LCMS (m/z): 505.7 (MH⁺).

I-6: N-(2-morpholino-5-(piperidin-1-yl)benzo[d]thiazol-6-yl)-5-(1H-pyrrolo[2,3-b]pyridin-5-yl)furan-2-carboxamide

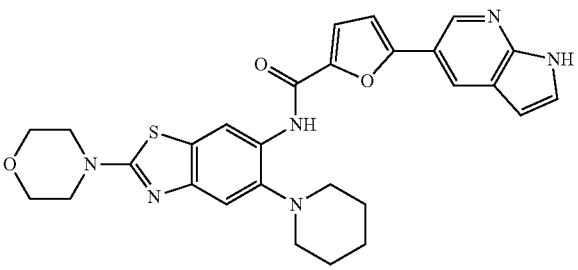 [SMILES: O=C(Nc1cc2sc(N3CCOCC3)nc2cc1N1CCCCC1)c1ccc(-c2cnc3[nH]ccc3c2)o1]

¹H NMR (300 MHz, DMSO-d₆) δ 11.94 (s, 1H), 9.90 (s, 1H), 8.82 (d, J=1.9 Hz, 1H), 8.67 (s, 1H), 8.46 (d, J=1.9 Hz, 1H), 7.57 (d, J=3.5 Hz, 1H), 7.44 (s, 1H), 7.36 (d, J=3.6 Hz, 1H), 7.20 (d, J=3.7 Hz, 1H), 6.48 (d, J=3.4 Hz, 1H), 3.76-3.69 (m, 4H), 3.51 (t, J=4.8 Hz, 4H), 2.86 (t, J=5.0 Hz, 4H), 1.83 (br s, 4H), 1.61 (br s, 2H).

LCMS (m/z): 529.9 (MH⁺).

I-7: N-(2-morpholino-5-(piperidin-1-yl)benzo[d]thiazol-6-yl)-5-(1H-pyrazol-4-yl)furan-2-carboxamide

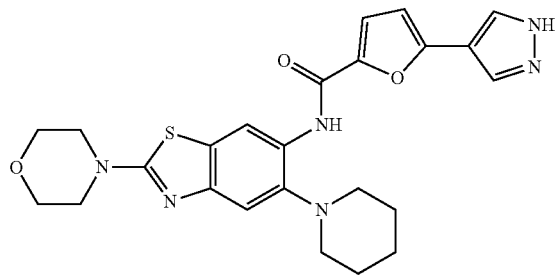 [SMILES: O=C(Nc1cc2sc(N3CCOCC3)nc2cc1N1CCCCC1)c1ccc(-c2cn[nH]c2)o1]

$^1$H NMR (300 MHz, DMSO-d$_6$) δ 13.26 (s, 1H), 9.64 (s, 1H), 8.62 (s, 1H), 8.18 (s, 1H), 7.91 (s, 1H), 7.39 (s, 1H), 7.28 (d, J=3.6 Hz, 1H), 6.77 (d, J=3.6 Hz, 1H), 3.72 (t, J=4.8 Hz, 4H), 3.50 (t, J=4.8 Hz, 4H), 2.83 (t, J=5.2 Hz, 4H), 1.77 (br s, 4H), 1.59 (br s, 2H).
LCMS (m/z): 479.7 (MH$^+$).

I-8: N-(2-morpholino-5-(piperidin-1-yl)benzo[d]thiazol-6-yl)-5-(1H-pyrazol-3-yl)furan-2-carboxamide

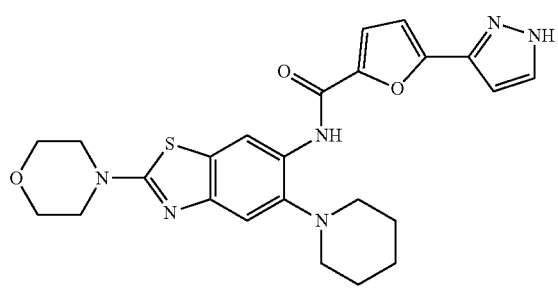 [SMILES: O=C(Nc1cc2sc(N3CCOCC3)nc2cc1N1CCCCC1)c1ccc(-c2cc[nH]n2)o1]

$^1$H NMR (300 MHz, DMSO-d$_6$) δ 13.21 (s, 1H), 9.76 (s, 1H), 8.64 (s, 1H), 7.89 (s, 1H), 7.39 (s, 1H), 7.31 (d, J=3.6 Hz, 1H), 6.91 (d, J=3.6 Hz, 1H), 6.66 (s, 1H), 3.72 (t, J=4.8 Hz, 4H), 3.50 (t, J=4.8 Hz, 4H), 2.83 (t, J=5.1 Hz, 4H), 1.80 (br s, 4H), 1.59 (br s, 2H).
LCMS (m/z): 479.7 (MH$^+$).

I-9: 5-(2-methylpyridin-4-yl)-N-(2-morpholino-5-(piperidin-1-yl)benzo[d]thiazol-6-yl)furan-2-carboxamide

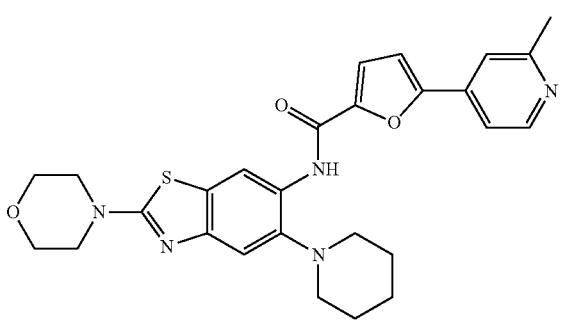 [SMILES: Cc1cc(-c2ccc(C(=O)Nc3cc4sc(N5CCOCC5)nc4cc3N3CCCCC3)o2)ccn1]

$^1$H NMR (300 MHz, DMSO-d$_6$) δ 9.85 (s, 1H), 8.63 (s, 1H), 8.54 (d, J=5.2 Hz, 1H), 7.70 (s, 1H), 7.64 (d, J=5.2 Hz, 1H), 7.47 (d, J=3.7 Hz, 1H), 7.43 (s, 1H), 7.40 (d, J=3.7 Hz, 1H), 3.75-3.69 (m, 4H), 3.54-3.48 (m, 4H), 2.85 (t, J=5.1 Hz, 4H), 2.53 (s, 3H), 1.79 (br s, 4H), 1.61 (br s, 2H).
LCMS (m/z): 504.7 (MH$^+$).

I-10: 5-(2-methylpyridin-4-yl)-N-(2-morpholino-5-(piperidin-1-yl)benzo[d]oxazol-6-yl)furan-2-carboxamide

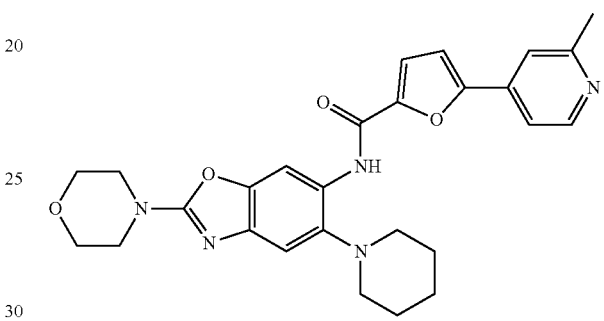

$^1$H NMR (300 MHz, DMSO-d$_6$) δ 9.98 (s, 1H), 8.55 (d, J=5.2 Hz, 1H), 8.38 (s, 1H), 7.69 (s, 1H), 7.63 (d, J=5.2 Hz, 1H), 7.47 (d, J=3.7 Hz, 1H), 7.39 (d, J=3.7 Hz, 1H), 7.32 (s, 1H), 3.72-3.68 (m, 4H), 3.57-3.53 (m, 4H), 2.83 (t, J=5.2 Hz, 4H), 2.53 (s, 3H), 1.80 (br s, 4H), 1.61 (br s, 2H).
LCMS (m/z): 488.7 (MH$^+$).

I-11: 2-(6-aminopyridin-3-yl)-N-(2-morpholino-5-(piperidin-1-yl)benzo[d]oxazol-6-yl)thiazole-4-carboxamide

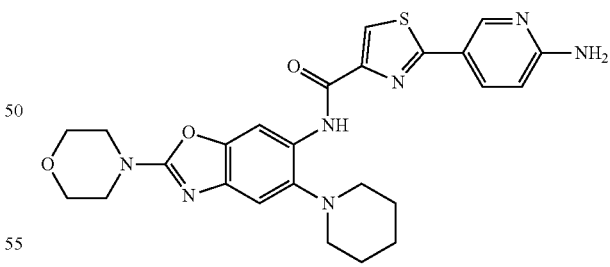

$^1$H NMR (300 MHz, DMSO-d$_6$) δ 10.76 (s, 1H), 8.68 (d, J=2.4 Hz, 1H), 8.49 (s, 1H), 8.29 (s, 1H), 7.96 (dd, J=8.7, 2.5 Hz, 1H), 7.28 (s, 1H), 6.69 (s, 2H), 6.54 (d, J=8.8 Hz, 1H), 3.73-3.68 (m, 4H), 3.58-3.53 (m, 4H), 2.80 (t, J=5.1 Hz, 4H), 1.80 (br s, 4H), 1.59 (br s, 2H).
LCMS (m/z): 506.6 (MH$^+$).

I-12: N-(2-morpholino-5-(piperidin-1-yl)benzo[d]oxazol-6-yl)-2-(1H-pyrazol-4-yl)thiazole-4-carboxamide

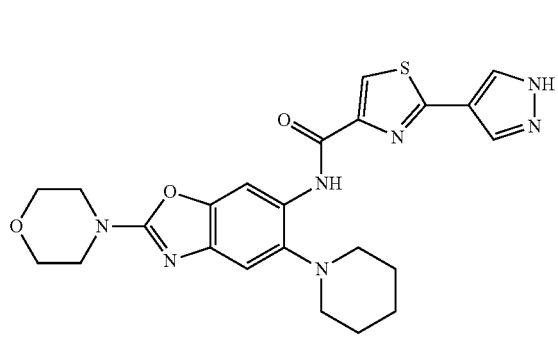 [SMILES: O=C(Nc1cc2oc(N3CCOCC3)nc2cc1N1CCCCC1)c1csc(-c2cn[nH]c2)n1]

¹H NMR (300 MHz, DMSO-d₆) δ 13.42 (s, 1H), 10.68 (s, 1H), 8.48 (s, 1H), 8.41 (d, J=1.3 Hz, 1H), 8.30 (s, 1H), 8.01 (d, J=1.8 Hz, 1H), 7.27 (s, 1H), 3.74-3.67 (m, 4H), 3.59-3.53 (m, 4H), 2.81 (t, J=5.3 Hz, 4H), 1.81 (br s, 4H), 1.61 (br s, 2H).

LCMS (m/z): 480.7 (MH⁺).

I-13: N-(2-morpholino-5-(piperidin-1-yl)benzo[d]oxazol-6-yl)-2-(1H-pyrazol-3-yl)thiazole-4-carboxamide

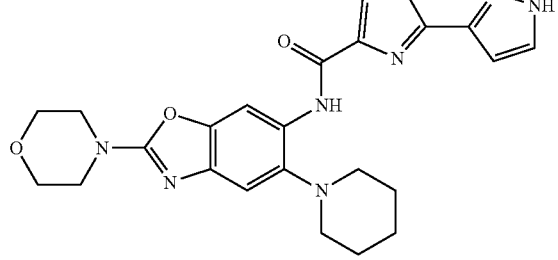

¹H NMR (300 MHz, DMSO-d₆) δ 13.40 (s, 1H), 10.72 (s, 1H), 8.49 (s, 1H), 8.37 (s, 1H), 7.99 (dd, J=2.4, 1.4 Hz, 1H), 7.27 (s, 1H), 6.76 (t, J=2.1 Hz, 1H), 3.73-3.68 (m, 4H), 3.58-3.53 (m, 4H), 2.81 (t, J=5.2 Hz, 4H), 1.83 (s, 4H), 1.61 (s, 2H).

LCMS (m/z): 480.7 (MH⁺).

I-14: 2-(2-methylpyridin-4-yl)-N-(2-morpholino-5-(piperidin-1-yl)benzo[d]oxazol-6-yl)thiazole-4-carboxamide

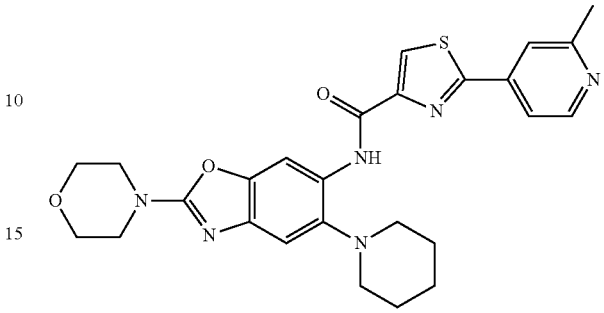

¹H NMR (300 MHz, DMSO-d₆) δ 10.79 (s, 1H), 8.64 (d, J=5.0 Hz, 1H), 8.62 (s, 1H), 8.49 (s, 1H), 7.91 (s, 1H), 7.77 (dd, J=5.2, 1.6 Hz, 1H), 7.31 (s, 1H), 3.74-3.67 (m, 4H), 3.58-3.53 (m, 4H), 2.82 (t, J=5.1 Hz, 4H), 2.57 (s, 3H), 1.83 (s, 4H), 1.63 (s, 2H).

LCMS (m/z): 505.7 (MH⁺).

I-15: 5-(6-aminopyridin-3-yl)-N-(2-(4-methylpiperazin-1-yl)-5-(piperidin-1-yl)benzo[d]oxazol-6-yl)furan-2-carboxamide

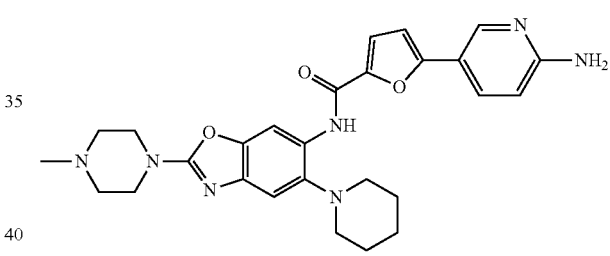

¹H NMR (300 MHz, DMSO-d₆) δ 9.88 (s, 1H), 8.50 (d, J=2.4 Hz, 1H), 8.37 (s, 1H), 7.83 (dd, J=8.7, 2.4 Hz, 1H), 7.30-7.25 (m, 2H), 6.91 (d, J=3.6 Hz, 1H), 6.52 (d, J=8.7 Hz, 1H), 6.44 (s, 2H), 3.60-3.54 (m, 4H), 2.80 (t, J=5.1 Hz, 4H), 2.40 (t, J=5.1 Hz, 4H), 2.21 (s, 3H), 1.76 (s, 4H), 1.58 (s, 2H).

LCMS (m/z): 502.8 (MH⁺).

I-16: N-(2-(4-methylpiperazin-1-yl)-5-(piperidin-1-yl)benzo[d]oxazol-6-yl)-5-(1H-pyrazol-4-yl)furan-2-carboxamide

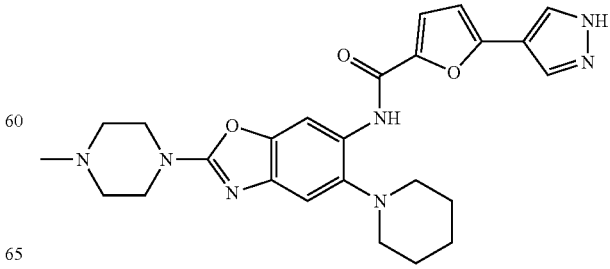

¹H NMR (300 MHz, DMSO-d₆) δ 13.26 (s, 1H), 9.79 (s, 1H), 8.35 (s, 1H), 8.18 (s, 1H), 7.90 (s, 1H), 7.29-7.25 (m, 2H), 6.77 (d, J=3.6 Hz, 1H), 3.57 (t, J=4.9 Hz, 4H), 2.80 (t, J=5.1 Hz, 4H), 2.41 (s, 4H), 2.21 (s, 3H), 1.77 (br s, 4H), 1.59 (br s, 2H).

LCMS (m/z): 476.8 (MH⁺).

I-17: N-(2-(4-methylpiperazin-1-yl)-5-(piperidin-1-yl)benzo[d]oxazol-6-yl)-5-(1H-pyrazol-3-yl)furan-2-carboxamide

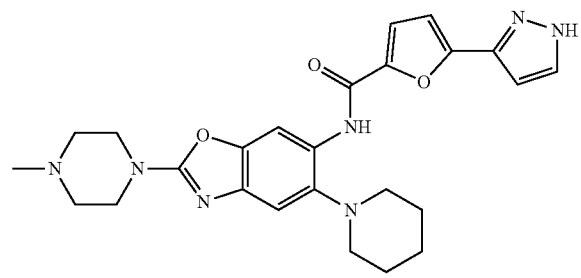 [SMILES: CN1CCN(c2nc3cc(N4CCCCC4)c(NC(=O)c4ccc(-c5cc[nH]n5)o4)cc3o2)CC1]

¹H NMR (300 MHz, DMSO-d₆) δ 13.21 (s, 1H), 9.92 (s, 1H), 8.36 (s, 1H), 7.89 (s, 1H), 7.30 (d, J=3.4 Hz, 1H), 7.26 (s, 1H), 6.91 (d, J=3.6 Hz, 1H), 6.66 (s, 1H), 3.57 (t, J=4.9 Hz, 4H), 2.80 (t, J=5.1 Hz, 4H), 2.40 (t, J=5.0 Hz, 4H), 2.21 (s, 3H), 1.80 (br s, 4H), 1.60 (br s, 2H).

LCMS (m/z): 476.8 (MH⁺).

I-18: N-(2-(4-methylpiperazin-1-yl)-5-(piperidin-1-yl)benzo[d]oxazol-6-yl)-5-(2-methylpyridin-4-yl)furan-2-carboxamide

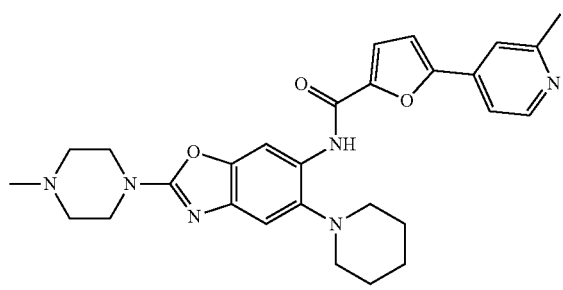

¹H NMR (300 MHz, DMSO-d₆) δ 9.98 (s, 1H), 8.55 (d, J=5.4 Hz, 1H), 8.36 (s, 1H), 7.69 (s, 1H), 7.63 (d, J=5.5 Hz, 1H), 7.48 (d, J=3.7 Hz, 1H), 7.40 (d, J=3.7 Hz, 1H), 7.30 (s, 1H), 3.57 (t, J=5.0 Hz, 4H), 2.82 (t, J=5.0 Hz, 4H), 2.53 (s, 3H), 2.40 (t, J=5.1 Hz, 4H), 2.21 (s, 3H), 1.80 (s, 4H), 1.61 (s, 2H).

LCMS (m/z): 501.7 (MH⁺).

I-19: 2-(6-aminopyridin-3-yl)-N-(2-(4-methylpiperazin-1-yl)-5-(piperidin-1-yl)benzo[d]oxazol-6-yl)thiazole-4-carboxamide

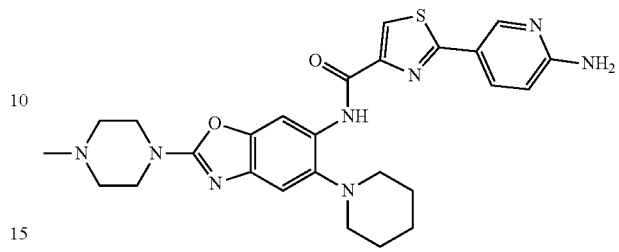

¹H NMR (300 MHz, DMSO-d₆) δ 10.76 (s, 1H), 8.68 (d, J=2.5 Hz, 1H), 8.47 (s, 1H), 8.29 (s, 1H), 7.96 (dd, J=8.7, 2.5 Hz, 1H), 7.26 (s, 1H), 6.69 (s, 2H), 6.54 (d, J=8.7 Hz, 1H), 3.57 (t, J=5.0 Hz, 4H), 2.80 (t, J=5.1 Hz, 4H), 2.40 (t, J=5.0 Hz, 6H), 2.21 (s, 3H), 1.80 (br s, 4H), 1.59 (br s, 2H).

LCMS (m/z): 519.7 (MH⁺).

I-20: N-(2-(4-methylpiperazin-1-yl)-5-(piperidin-1-yl)benzo[d]oxazol-6-yl)-2-(1H-pyrazol-4-yl)thiazole-4-carboxamide

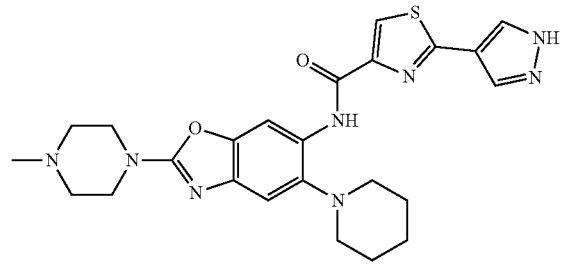 [SMILES: CN1CCN(c2nc3cc(N4CCCCC4)c(NC(=O)c4csc(-c5cn[nH]c5)n4)cc3o2)CC1]

¹H NMR (300 MHz, DMSO-d₆) δ 13.42 (s, 1H), 10.68 (s, 1H), 8.47 (s, 1H), 8.41 (s, 1H), 8.30 (s, 1H), 8.02 (s, 1H), 7.25 (s, 1H), 3.57 (t, J=5.0 Hz, 4H), 2.81 (t, J=4.9 Hz, 4H), 2.41 (t, J=5.0 Hz, 4H), 2.21 (s, 3H), 1.82 (p, J=5.7 Hz, 5H), 1.60 (br s, 2H).

LCMS (m/z): 493.7 (MH⁺).

I-21: N-(2-(4-methylpiperazin-1-yl)-5-(piperidin-1-yl)benzo[d]oxazol-6-yl)-2-(1H-pyrazol-3-yl)thiazole-4-carboxamide

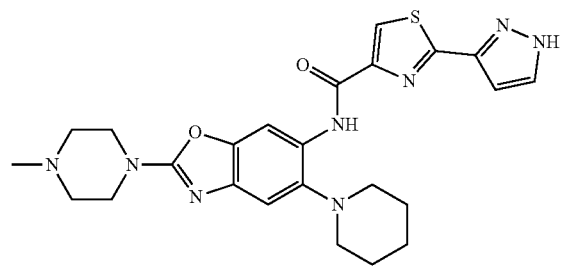 [SMILES: CN1CCN(c2nc3cc(N4CCCCC4)c(NC(=O)c4csc(-c5cc[nH]n5)n4)cc3o2)CC1]

¹H NMR (300 MHz, DMSO-d₆) δ 13.40 (s, 1H), 10.71 (s, 1H), 8.48 (s, 1H), 8.37 (s, 1H), 7.99 (s, 1H), 7.25 (s, 1H), 6.76 (s, 1H), 3.62-3.52 (br m, 4H), 2.86-2.77 (br m, 4H), 2.45-2.38 (br m, 4H), 2.21 (s, 3H), 1.83 (s, 4H), 1.62 (br s, 2H).

LCMS (m/z): 493.8 (MH⁺).

I-22: N-(2-(4-methylpiperazin-1-yl)-5-(piperidin-1-yl)benzo[d]oxazol-6-yl)-2-(2-methylpyridin-4-yl)thiazole-4-carboxamide

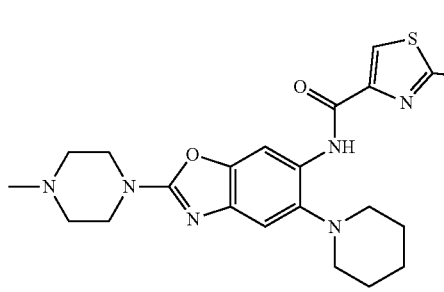

¹H NMR (300 MHz, DMSO-d₆) δ 10.80 (s, 1H), 8.68-8.61 (m, 2H), 8.49 (s, 1H), 7.93 (s, 1H), 7.79 (d, J=6.1 Hz, 1H), 7.29 (s, 1H), 3.61-3.55 (br m, 4H), 2.86-2.80 (br m, 4H), 2.58 (s, 3H), 2.41 (br s, 4H), 2.21 (s, 3H), 1.83 (br s, 4H), 1.65 (br s, 2H).

LCMS (m/z): 518.7 (MH⁺).

I-23: N-(5-(4-fluoropiperidin-1-yl)-2-morpholinobenzo[d]oxazol-6-yl)-5-(1H-pyrazol-4-yl)furan-2-carboxamide

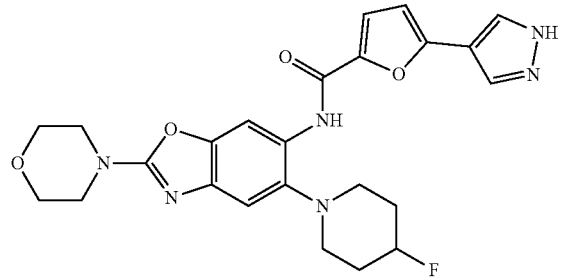 [SMILES: O=C(Nc1cc2oc(N3CCOCC3)nc2cc1N1CCC(F)CC1)c1ccc(-c2cn[nH]c2)o1]

¹H NMR (300 MHz, DMSO-d₆) δ 13.25 (s, 1H), 9.65 (s, 1H), 8.34 (s, 1H), 8.18 (s, 1H), 7.29 (d, J=3.7 Hz, 2H), 6.77 (d, J=3.7 Hz, 1H), 4.86 (br d, J=48.3 Hz, 1H), 3.73-3.67 (br m, 4H), 3.58-3.52 (br m, 4H), 3.04-2.93 (br m, 2H), 2.88-2.75 (br m, 1H), 2.21-1.90 (br m, 1H).

LCMS (m/z): 481.8 (MH⁺).

I-24: N-(5-(4-fluoropiperidin-1-yl)-2-morpholinobenzo[d]oxazol-6-yl)-5-(2-methylpyridin-4-yl)furan-2-carboxamide

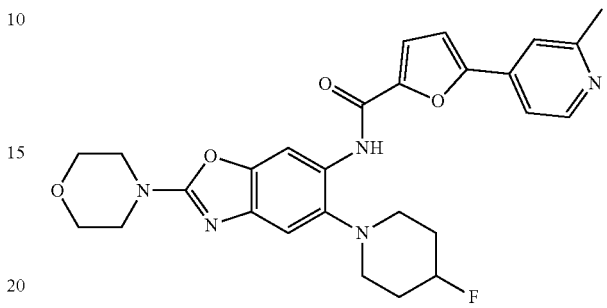

¹H NMR (300 MHz, DMSO-d₆) δ 9.86 (s, 1H), 8.52 (d, J=5.1 Hz, 1H), 8.35 (s, 1H), 7.68 (s, 1H), 7.62 (d, J=5.4 Hz, 1H), 7.47 (d, J=3.7 Hz, 1H), 7.41 (d, J=3.7 Hz, 1H), 7.33 (s, 1H), 4.88 (br d, J=48.0 Hz, 1H), 3.71 (t, J=4.8 Hz, 4H), 3.56 (t, J=4.8 Hz, 4H), 3.05-2.96 (br m, 2H), 2.88-2.80 (br m, 2H), 2.52 (s, 3H), 2.21-1.95 (br m, 4H).

LCMS (m/z): 506.7 (MH⁺).

I-25: N-(5-(4-fluoropiperidin-1-yl)-2-morpholinobenzo[d]oxazol-6-yl)-2-(1H-pyrazol-4-yl)thiazole-4-carboxamide

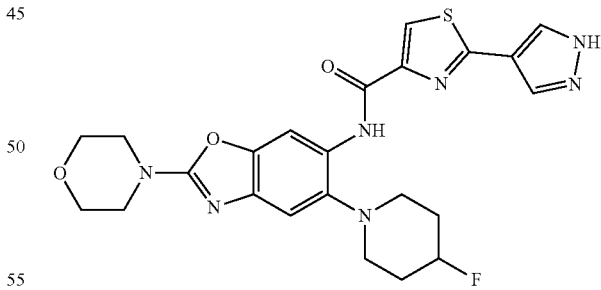

¹H NMR (300 MHz, DMSO-d₆) δ 13.43 (s, 1H), 10.56 (s, 1H), 8.48 (s, 1H), 8.40 (s, 1H), 8.31 (s, 1H), 8.02 (s, 1H), 7.29 (s, 1H), 4.88 (br d, J=48.7 Hz, 1H), 3.70 (t, J=4.8 Hz, 4H), 3.56 (t, J=4.8 Hz, 4H), 3.04-2.93 (br m, 2H), 2.90-2.78 (br m, 2H), 2.24-2.00 (br m, 4H).

LCMS (m/z): 498.7 (MH⁺).

I-26: N-(5-(4-fluoropiperidin-1-yl)-2-morpholinobenzo[d]oxazol-6-yl)-2-(2-methylpyridin-4-yl)thiazole-4-carboxamide

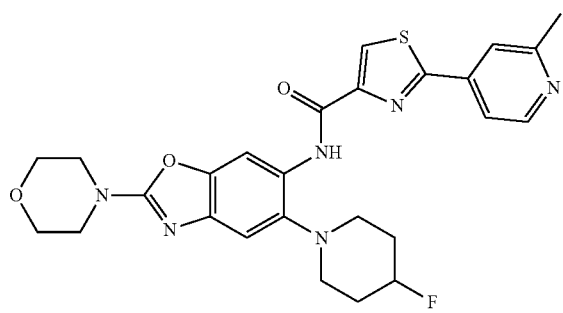 [SMILES: Cc1cc(-c2nc(C(=O)Nc3cc4oc(N5CCOCC5)nc4cc3N3CCC(F)CC3)cs2)ccn1]

¹H NMR (300 MHz, DMSO-d₆) δ 10.65 (s, 1H), 8.63 (s, 1H), 8.61 (d, J=5.8 Hz, 1H), 8.49 (s, 1H), 7.85 (s, 1H), 7.75 (d, J=5.2 Hz, 1H), 7.32 (s, 1H), 4.88 (br d, J=48.4 Hz, 1H), 3.71 (t, J=4.8 Hz, 4H), 3.56 (t, J=4.8 Hz, 4H), 3.07-2.94 (br m, 2H), 2.90-2.79 (br m, 2H), 2.56 (s, 3H), 2.25-1.98 (br m, 4H).

LCMS (m/z): 523.8 (MH⁺).

I-27: N-(5-(4,4-difluoropiperidin-1-yl)-2-morpholinobenzo[d]oxazol-6-yl)-5-(1H-pyrazol-4-yl)furan-2-carboxamide

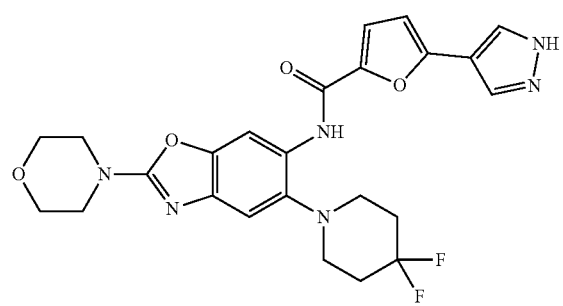 [SMILES: O=C(Nc1cc2oc(N3CCOCC3)nc2cc1N1CCC(F)(F)CC1)c1ccc(-c2cn[nH]c2)o1]

¹H NMR (300 MHz, DMSO-d₆) δ 13.27 (s, 1H), 9.59 (s, 1H), 8.32 (s, 1H), 8.17 (s, 1H), 7.89 (s, 1H), 7.34 (s, 1H), 7.30 (d, J=3.6 Hz, 1H), 6.77 (d, J=3.6 Hz, 1H), 3.70 (t, J=4.8 Hz, 4H), 3.55 (t, J=4.8 Hz, 4H), 2.98 (t, J=5.5 Hz, 4H), 2.31-2.14 (br m, 4H).

LCMS (m/z): 499.7 (MH⁺).

I-28: N-(5-(4,4-difluoropiperidin-1-yl)-2-morpholinobenzo[d]oxazol-6-yl)-5-(2-methylpyridin-4-yl)furan-2-carboxamide

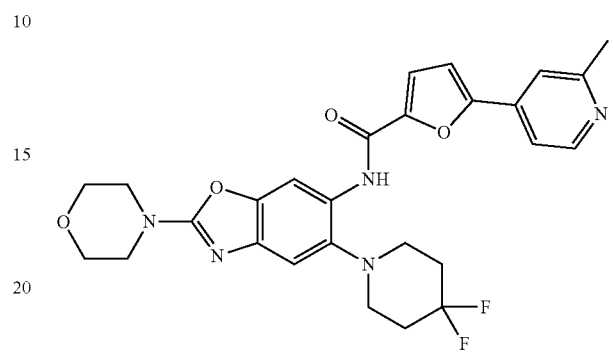

¹H NMR (300 MHz, DMSO-d₆) δ 9.80 (s, 1H), 8.49 (d, J=5.2 Hz, 1H), 8.31 (s, 1H), 7.69 (s, 1H), 7.61 (d, J=5.2 Hz, 1H), 7.46 (d, J=3.7 Hz, 1H), 7.42 (d, J=3.7 Hz, 1H), 7.37 (s, 1H), 3.71 (t, J=4.8 Hz, 4H), 3.56 (t, J=4.8 Hz, 4H), 2.99 (t, J=5.5 Hz, 4H), 2.51 (s, 3H), 2.30-2.16 (br m, 4H).

LCMS (m/z): 524.8 (MH⁺).

I-29: N-(5-(4,4-difluoropiperidin-1-yl)-2-morpholinobenzo[d]oxazol-6-yl)-2-(1H-pyrazol-4-yl)thiazole-4-carboxamide

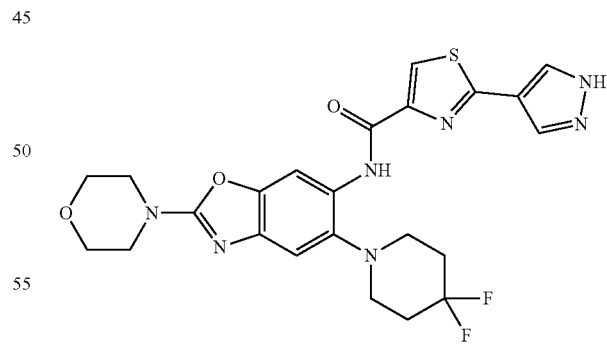

¹H NMR (300 MHz, DMSO-d₆) δ 13.46 (s, 1H), 10.50 (s, 1H), 8.47 (s, 1H), 8.38 (s, 1H), 8.32 (s, 1H), 7.99 (s, 1H), 7.35 (s, 1H), 3.71 (t, J=4.8 Hz, 4H), 3.56 (t, J=4.8 Hz, 4H), 2.99 (t, J=5.6 Hz, 4H), 2.36-2.21 (br m, 4H).

LCMS (m/z): 516.6 (MH⁺).

I-30: N-(5-(4,4-difluoropiperidin-1-yl)-2-morpholinobenzo[d]oxazol-6-yl)-2-(2-methylpyridin-4-yl)thiazole-4-carboxamide

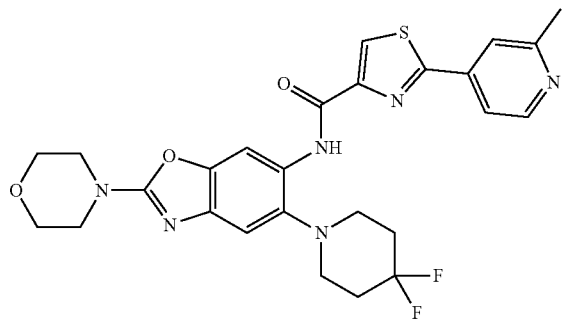 [SMILES: Cc1cc(-c2nc(C(=O)Nc3cc4oc(N5CCOCC5)nc4cc3N3CCC(F)(F)CC3)cs2)ccn1]

$^1$H NMR (300 MHz, DMSO-d$_6$) δ 10.59 (s, 1H), 8.65 (s, 1H), 8.58 (d, J=5.1 Hz, 1H), 8.49 (s, 1H), 7.83 (s, 1H), 7.74 (d, J=5.7 Hz, 1H), 7.39 (s, 1H), 3.71 (t, J=4.8 Hz, 4H), 3.57 (t, J=4.8 Hz, 4H), 3.01 (t, J=5.6 Hz, 4H), 2.56 (s, 3H), 2.34-2.20 (br m, 4H).
LCMS (m/z): 541.9 (MH$^+$).

I-31: N-(2,5-di(piperidin-1-yl)benzo[d]oxazol-6-yl)-5-(1H-pyrazol-4-yl)furan-2-carboxamide

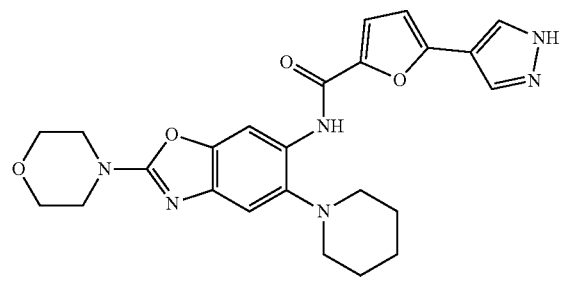 [SMILES: O=C(Nc1cc2oc(N3CCOCC3)nc2cc1N1CCCCC1)c1ccc(-c2cn[nH]c2)o1]

$^1$H NMR (300 MHz, DMSO-d$_6$) δ 13.26 (s, 1H), 9.78 (s, 1H), 8.33 (s, 1H), 8.17 (s, 1H), 7.90 (s, 1H), 7.33-7.17 (m, 2H), 6.77 (d, J=3.7 Hz, 1H), 3.56 (br s, 4H), 2.80 (t, J=5.1 Hz, 4H), 1.77 (br s, 4H), 1.60 (br s, 8H).
LCMS (m/z): 461.7 (MH$^+$).

I-32: N-(2,5-di(piperidin-1-yl)benzo[d]oxazol-6-yl)-5-(1H-pyrazol-3-yl)furan-2-carboxamide

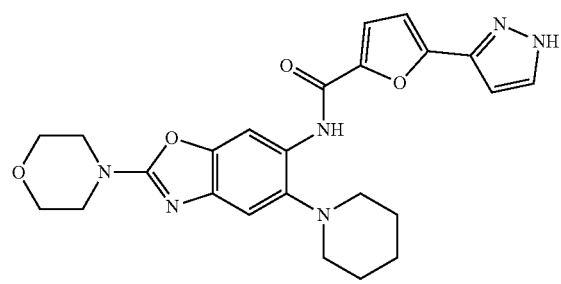 [SMILES: O=C(Nc1cc2oc(N3CCOCC3)nc2cc1N1CCCCC1)c1ccc(-c2cc[nH]n2)o1]

$^1$H NMR (300 MHz, DMSO-d$_6$) δ 13.21 (s, 1H), 9.91 (s, 1H), 8.35 (s, 1H), 7.90 (s, 1H), 7.29 (d, J=3.7 Hz, 1H), 7.24 (s, 1H), 6.91 (d, J=3.7 Hz, 1H), 6.66 (s, 1H), 3.56 (br s, 4H), 2.80 (br s, 4H), 1.80 (br s, 4H), 1.59 (br s, 8H).
LCMS (m/z): 461.7 (MH$^+$).

I-33: N-(2,5-di(piperidin-1-yl)benzo[d]oxazol-6-yl)-5-(2-methylpyridin-4-yl)furan-2-carboxamide

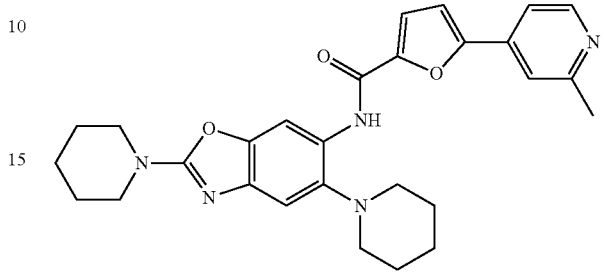

$^1$H NMR (300 MHz, DMSO-d$_6$) δ 9.97 (s, 1H), 8.55 (d, J=5.0 Hz, 1H), 8.35 (s, 1H), 7.69 (s, 1H), 7.63 (d, J=5.0 Hz, 1H), 7.47 (dd, J=3.6, 1.3 Hz, 1H), 7.39 (dd, J=3.6, 1.3 Hz, 1H), 7.28 (d, J=1.3 Hz, 1H), 3.58-3.52 (m, 4H), 2.84-2.80 (m, 4H), 2.53 (s, 3H), 1.84-1.78 (m, 4H), 1.63-1.54 (m, 8H).
LCMS (m/z): 486.8 (MH$^+$).

I-34: 2-(6-aminopyridin-3-yl)-N-(2,5-di(piperidin-1-yl)benzo[d]oxazol-6-yl)thiazole-4-carboxamide

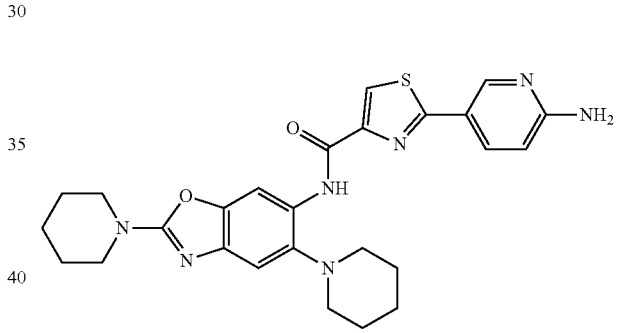

$^1$H NMR (300 MHz, DMSO-d$_6$) δ 10.75 (s, 1H), 8.68 (d, J=2.4 Hz, 1H), 8.46 (s, 1H), 8.29 (s, 1H), 7.96 (dd, J=8.7, 2.4 Hz, 1H), 7.24 (s, 1H), 6.69 (s, 2H), 6.54 (d, J=9.3 Hz, 1H), 3.57-3.53 (m, 4H), 2.84-2.76 (m, 4H), 1.84-1.75 (m, 4H), 1.65-1.52 (m, 8H).
LCMS (m/z): 504.3 (MH$^+$).

I-35: N-(2,5-di(piperidin-1-yl)benzo[d]oxazol-6-yl)-2-(1H-pyrazol-4-yl)thiazole-4-carboxamide

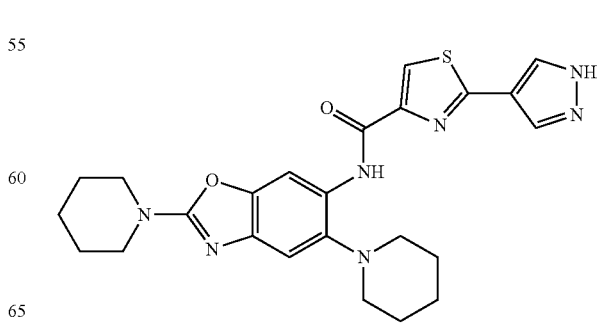

¹H NMR (300 MHz, DMSO-d₆) δ 13.42 (s, 1H), 10.67 (s, 1H), 8.45 (s, 1H), 8.41 (s, 1H), 8.29 (s, 1H), 8.02 (s, 1H), 7.22 (s, 1H), 3.60-3.52 (m, 4H), 2.84-2.77 (m, 4H), 1.86-1.75 (m, 4H), 1.60 (br s, 8H).

LCMS (m/z): 478.7 (MH⁺).

I-36: N-(2,5-di(piperidin-1-yl)benzo[d]oxazol-6-yl)-2-(1H-pyrazol-3-yl)thiazole-4-carboxamide

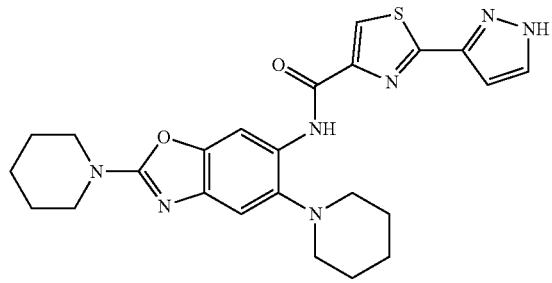 [SMILES: O=C(Nc1cc2oc(N3CCCCC3)nc2cc1N1CCCCC1)c1csc(-c2cc[nH]n2)n1]

¹H NMR (300 MHz, DMSO-d₆) δ 13.40 (s, 1H), 10.71 (s, 1H), 8.46 (s, 1H), 8.36 (s, 1H), 8.00 (s, 1H), 7.23 (s, 1H), 6.76 (s, 1H), 3.60-3.52 (m, 4H), 2.85-2.77 (m, 4H), 1.86-1.79 (m, 4H), 1.60 (br s, 8H).

LCMS (m/z): 478.7 (MH⁺).

I-37: N-(2,5-di(piperidin-1-yl)benzo[d]oxazol-6-yl)-2-(2-methylpyridin-4-yl)thiazole-4-carboxamide

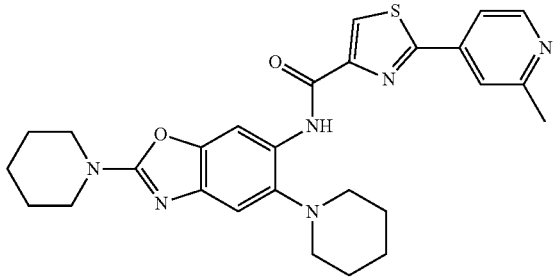 [SMILES: Cc1cc(-c2nc(C(=O)Nc3cc4oc(N5CCCCC5)nc4cc3N3CCCCC3)cs2)ccn1]

¹H NMR (300 MHz, DMSO-d₆) δ 10.78 (s, 1H), 8.68-8.59 (m, 2H), 8.46 (s, 1H), 7.92 (s, 1H), 7.78 (d, J=6.6 Hz, 1H), 7.26 (s, 1H), 3.59-3.52 (m, 4H), 2.89-2.74 (m, 4H), 1.83 (q, J=6.8, 5.6 Hz, 4H), 1.60 (br s, 8H).

LCMS (m/z): 503.7 (MH⁺).

I-38: N-(5-(3-fluoropiperidin-1-yl)-2-morpholinobenzo[d]oxazol-6-yl)-5-(1H-pyrazol-4-yl)furan-2-carboxamide

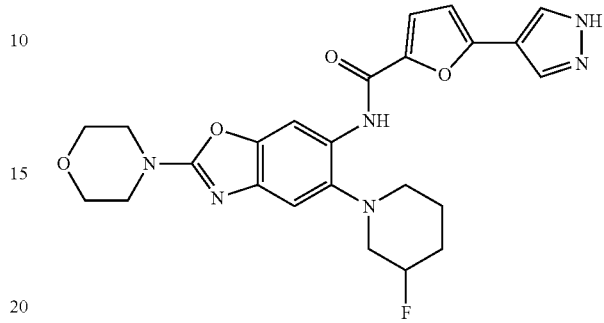

¹H NMR (300 MHz, DMSO-d₆) δ 13.22 (s, 1H), 9.77 (s, 1H), 8.43 (s, 1H), 8.20 (s, 1H), 7.96 (s, 1H), 7.34 (s, 1H), 7.26 (d, J=3.6 Hz, 1H), 6.76 (d, J=3.6 Hz, 1H), 4.96 (d, J=47.0 Hz, 1H), 3.74-3.68 (m, 4H), 3.57-3.53 (m, 4H), 3.13-3.02 (m, 2H), 2.86-2.79 (m, 2H), 2.09-1.65 (m, 4H).

LCMS (m/z): 481.7 (MH⁺).

I-39: N-(5-(3-fluoropiperidin-1-yl)-2-morpholinobenzo[d]oxazol-6-yl)-5-(2-methylpyridin-4-yl)furan-2-carboxamide

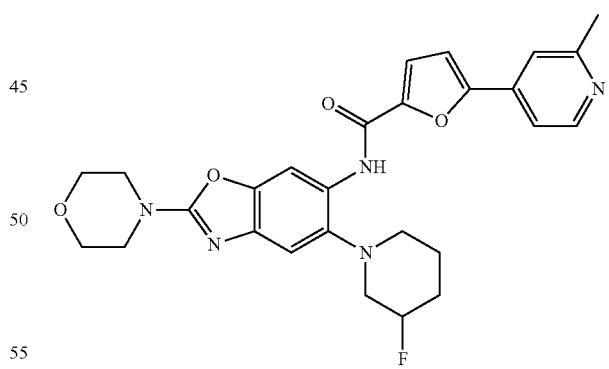

¹H NMR (300 MHz, DMSO-d₆) δ 9.94 (s, 1H), 8.52 (d, J=5.2 Hz, 1H), 8.43 (s, 1H), 7.74 (s, 1H), 7.66 (d, J=5.2 Hz, 1H), 7.46 (d, J=3.7 Hz, 1H), 7.40-7.36 (m, 2H), 4.97 (d, J=47.4 Hz, 1H), 3.74-3.68 (m, 4H), 3.59-3.53 (m, 4H), 3.14-3.02 (m, 2H), 2.89-2.82 (m, 2H), 2.52 (s, 3H), 2.13-1.69 (m, 4H).

LCMS (m/z): 506.9 (MH⁺).

I-40: N-(5-(3-fluoropiperidin-1-yl)-2-morpholinobenzo[d]oxazol-6-yl)-2-(1H-pyrazol-4-yl)thiazole-4-carboxamide

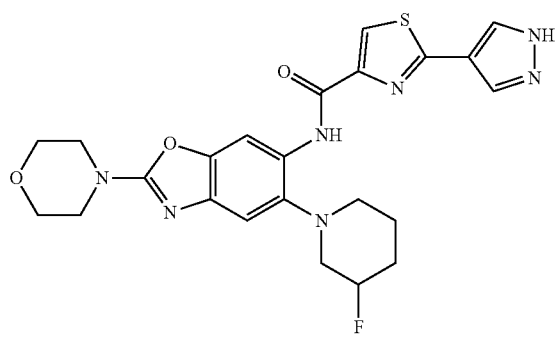 [SMILES: O=C(Nc1cc2oc(N3CCOCC3)nc2cc1N1CCCC(F)C1)c1csc(-c2cn[nH]c2)n1]

$^1$H NMR (300 MHz, DMSO-d$_6$) δ 13.39 (s, 1H), 10.60 (s, 1H), 8.51 (s, 1H), 8.43 (s, 1H), 8.29 (s, 1H), 8.08 (s, 1H), 7.32 (s, 1H), 4.97 (d, J=47.2 Hz, 1H), 3.75-3.67 (m, 4H), 3.60-3.53 (m, 4H), 3.21 (dd, J=25.5, 11.5 Hz, 1H), 3.09-2.98 (br m, 1H), 2.84-2.67 (br m, 2H), 2.11 (br s, 1H), 2.01-1.81 (m, 2H), 1.71 (br s, 1H).

LCMS (m/z): 498.7 (MH$^+$).

I-41: N-(5-(3-fluoropiperidin-1-yl)-2-morpholinobenzo[d]oxazol-6-yl)-2-(2-methylpyridin-4-yl)thiazole-4-carboxamide

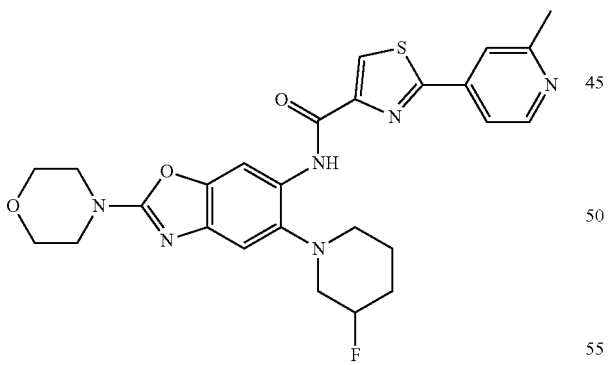

$^1$H NMR (300 MHz, DMSO-d$_6$) δ 10.69 (s, 1H), 8.62 (m, J=5.8 Hz, 2H), 8.53 (s, 1H), 7.97 (s, 1H), 7.81 (d, J=5.8 Hz, 1H), 7.36 (s, 1H), 4.99 (d, J=50.0 Hz, 1H), 3.75-3.67 (m, 4H), 3.61-3.53 (m, 4H), 3.28-3.13 (br m, 1H), 3.12-2.99 (br m, 1H), 2.86-2.69 (br m, 2H), 2.57 (s, 3H), 2.12 (br s, 1H), 2.02-1.79 (br m, 2H), 1.72 (br s, 1H).

LCMS (m/z): 523.9 (MH$^+$).

I-42: N-(5-(3,3-difluoropiperidin-1-yl)-2-morpholinobenzo[d]oxazol-6-yl)-5-(1H-pyrazol-4-yl)furan-2-carboxamide

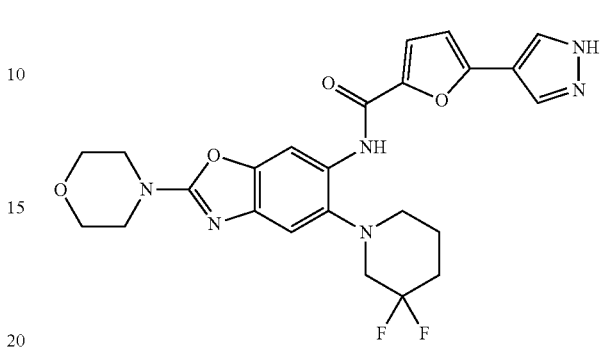

$^1$H NMR (300 MHz, DMSO-d$_6$) δ 13.23 (s, 1H), 9.63 (s, 1H), 8.44 (s, 1H), 8.15 (s, 1H), 7.93 (s, 1H), 7.40 (s, 1H), 7.26 (d, J=3.6 Hz, 1H), 6.77 (d, J=3.6 Hz, 1H), 3.73-3.68 (m, 4H), 3.59-3.52 (m, 4H), 3.20 (br t, J=11.3 Hz, 2H), 2.89-2.82 (br m, 2H), 2.16-2.04 (br m, 2H), 1.95-1.87 (br m, 2H).

LCMS (m/z): 499.7 (MH$^+$).

I-43: N-(5-(3,3-difluoropiperidin-1-yl)-2-morpholinobenzo[d]oxazol-6-yl)-5-(2-methylpyridin-4-yl)furan-2-carboxamide

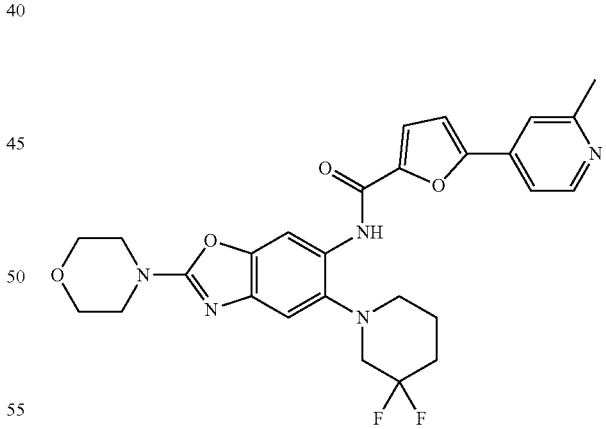

$^1$H NMR (300 MHz, DMSO-d$_6$) δ 9.78 (s, 1H), 8.53 (d, J=5.5 Hz, 1H), 8.44 (s, 1H), 7.68 (s, 1H), 7.63 (d, J=5.1 Hz, 1H), 7.47 (d, J=3.7 Hz, 1H), 7.43 (s, 1H), 7.39 (d, J=3.7 Hz, 1H), 3.75-3.68 (m, 4H), 3.61-3.54 (m, 4H), 3.25-3.15 (m, 2H), 2.92-2.86 (br m, 2H), 2.53 (s, 3H), 2.20-2.03 (br m, 2H), 2.01-1.88 (m, 2H).

LCMS (m/z): 524.8 (MH$^+$).

I-44: N-(5-(3,3-difluoropiperidin-1-yl)-2-morpholinobenzo[d]oxazol-6-yl)-2-(1H-pyrazol-4-yl)thiazole-4-carboxamide

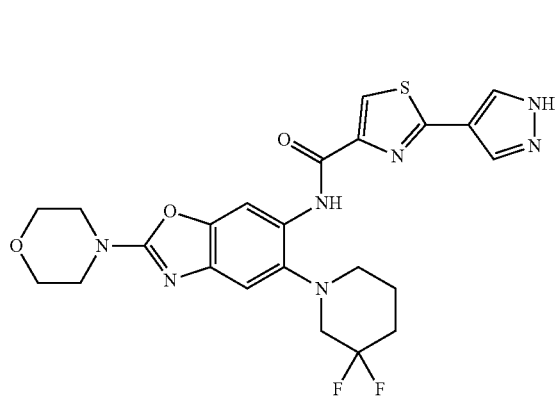 [SMILES: O=C(Nc1cc2oc(N3CCOCC3)nc2cc1N1CCCC(F)(F)C1)c1csc(-c2cn[nH]c2)n1]

¹H NMR (300 MHz, DMSO-d₆) δ 13.39 (s, 1H), 10.53 (s, 1H), 8.52 (s, 1H), 8.39 (s, 1H), 8.29 (s, 1H), 8.06 (s, 1H), 7.38 (s, 1H), 3.74-3.67 (m, 4H), 3.60-3.54 (m, 4H), 3.25 (br d, J=12.0 Hz, 2H), 2.78 (br s, 2H), 2.16-1.90 (br m, 4H).

LCMS (m/z): 516.6 (MH⁺).

I-45: N-(5-(3,3-difluoropiperidin-1-yl)-2-morpholinobenzo[d]oxazol-6-yl)-2-(2-methylpyridin-4-yl)thiazole-4-carboxamide

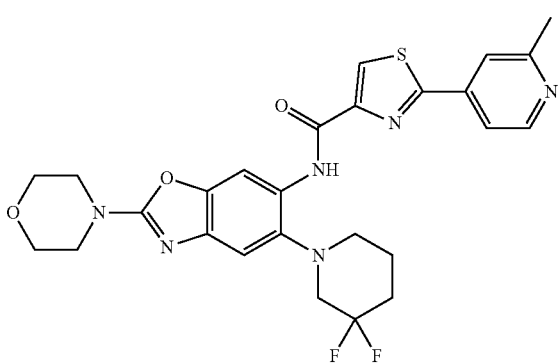 [SMILES: Cc1cc(-c2nc(C(=O)Nc3cc4oc(N5CCOCC5)nc4cc3N3CCCC(F)(F)C3)cs2)ccn1]

¹H NMR (300 MHz, DMSO-d₆) δ 10.58 (s, 1H), 8.67-8.58 (m, 2H), 8.55 (s, 1H), 7.93 (s, 1H), 7.79 (d, J=6.4 Hz, 1H), 7.42 (s, 1H), 3.74-3.67 (m, 4H), 3.59-3.54 (m, 4H), 3.26 (d, J=11.1 Hz, 2H), 2.81 (s, 0H), 2.58 (s, 3H), 2.23-2.00 (m, 0H), 1.95 (s, 2H).

LCMS (m/z): 541.7 (MH⁺).

I-46: N-(2-morpholino-5-(pyrrolidin-1-yl)benzo[d]oxazol-6-yl)-5-(1H-pyrazol-4-yl)furan-2-carboxamide

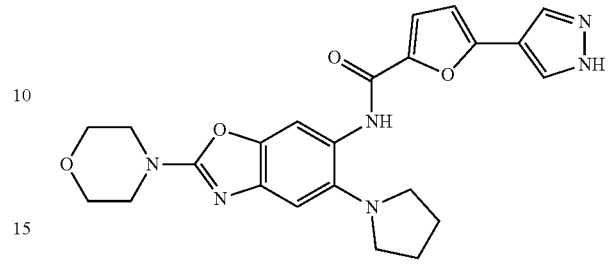

¹H NMR (300 MHz, DMSO-d₆) δ 13.20 (s, 1H), 9.63 (s, 1H), 8.19 (s, 1H), 7.95-7.85 (m, 2H), 7.26 (d, J=3.5 Hz, 1H), 7.13 (s, 1H), 6.72 (d, J=3.5 Hz, 1H), 3.74-3.66 (m, 4H), 3.60-3.52 (m, 4H), 3.10-3.05 (br m, 4H), 1.95-1.88 (br m, 4H).

LCMS (m/z): 449.7 (MH⁺).

I-47: N-(2-morpholino-5-(pyrrolidin-1-yl)benzo[d]oxazol-6-yl)-2-(1H-pyrazol-4-yl)thiazole-4-carboxamide

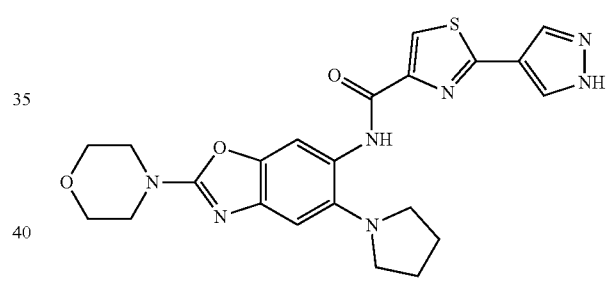

¹H NMR (300 MHz, DMSO-d₆) δ 13.40 (s, 1H), 10.40 (s, 1H), 8.40 (s, 2H), 8.29 (s, 1H), 7.98 (s, 1H), 7.29 (s, 1H), 3.74-3.67 (m, 4H), 3.60-3.52 (m, 4H), 3.06-2.99 (br m, 4H), 2.00-1.96 (br m, 4H).

LCMS (m/z): 466.6 (MH⁺).

I-48: N-(2,5-dimorpholinobenzo[d]oxazol-6-yl)-5-(1H-pyrazol-4-yl)furan-2-carboxamide

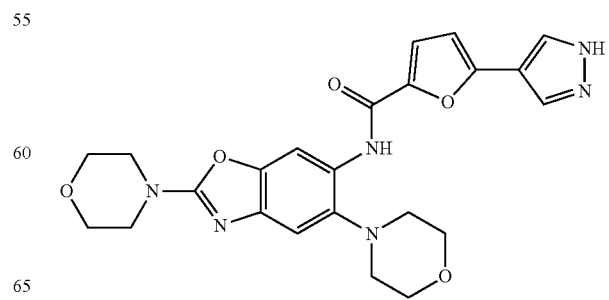

¹H NMR (300 MHz, DMSO-d₆) δ 13.28 (s, 1H), 9.75 (s, 1H), 8.37 (s, 1H), 8.22 (s, 1H), 7.94 (s, 1H), 7.36 (s, 1H), 7.29 (d, J=3.6 Hz, 1H), 6.77 (d, J=3.6 Hz, 1H), 3.87-3.79 (m, 4H), 3.74-3.67 (m, 4H), 3.59-3.53 (m, 4H), 2.90-2.82 (m, 4H). LCMS (m/z): 465.7 (MH⁺).

I-49: N-(2,5-dimorpholinobenzo[d]oxazol-6-yl)-2-(1H-pyrazol-4-yl)thiazole-4-carboxamide

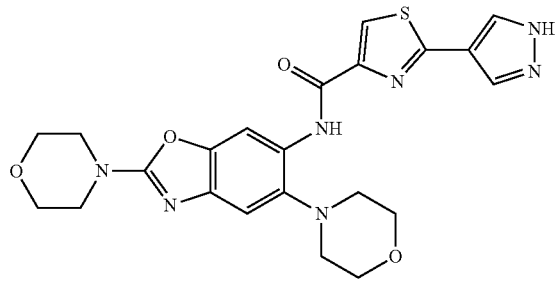

¹H NMR (300 MHz, DMSO-d₆) δ 13.45 (s, 1H), 10.64 (s, 1H), 8.50 (s, 1H), 8.45 (s, 1H), 8.31 (s, 1H), 8.06 (s, 1H), 7.35 (s, 1H), 3.91-3.85 (m, 4H), 3.74-3.67 (m, 4H), 3.60-3.52 (m, 4H), 2.90-2.83 (m, 4H).

LCMS (m/z): 482.7 (MH⁺).

I-50: N-(2-((2-methoxyethyl)(methyl)amino)-5-(piperidin-1-yl)benzo[d]oxazol-6-yl)-5-(1H-pyrazol-4-yl)furan-2-carboxamide

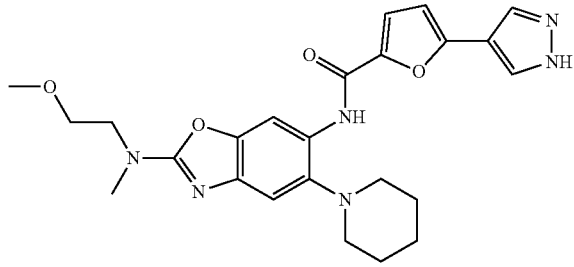 [SMILES: COCCN(C)c1nc2cc(N3CCCCC3)c(NC(=O)c3ccc(-c4cn[nH]c4)o3)cc2o1]

¹H NMR (300 MHz, DMSO-d₆) δ 13.26 (s, 1H), 9.78 (s, 1H), 8.33 (s, 1H), 8.17 (s, 1H), 7.90 (s, 1H), 7.27 (d, J=3.6 Hz, 1H), 7.23 (s, 1H), 6.77 (d, J=3.6 Hz, 1H), 3.65 (t, J=5.2 Hz, 2H), 3.56 (t, J=5.2 Hz, 2H), 3.25 (s, 3H), 3.13 (s, 3H), 2.84-2.76 (m, 4H), 1.82-1.73 (br m, 4H), 1.65-1.54 (br m, 2H).

LCMS (m/z): 465.7 (MH⁺).

I-51: N-(2-((2-methoxyethyl)(methyl)amino)-5-(piperidin-1-yl)benzo[d]oxazol-6-yl)-2-(1H-pyrazol-4-yl)thiazole-4-carboxamide

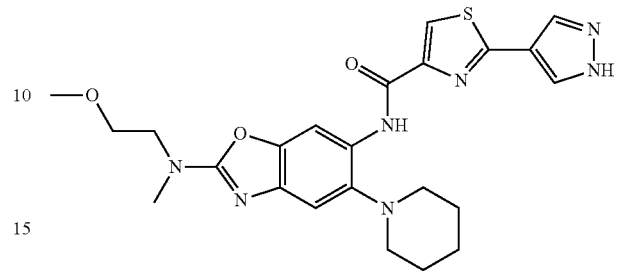

¹H NMR (300 MHz, DMSO-d₆) δ 13.42 (s, 1H), 10.67 (s, 1H), 8.45 (s, 1H), 8.41 (s, 1H), 8.29 (s, 1H), 8.02 (s, 1H), 7.22 (s, 1H), 3.65 (t, J=5.6 Hz, 2H), 3.57 (t, J=5.6 Hz, 2H), 3.25 (s, 3H), 3.13 (s, 3H), 2.85-2.77 (m, 4H), 1.87-1.76 (m, 4H), 1.66-1.55 (m, 2H).

LCMS (m/z): 482.6 (MH⁺).

I-52: N-(2-((2-morpholinoethyl)amino)-5-(piperidin-1-yl)benzo[d]oxazol-6-yl)-2-(1H-pyrazol-4-yl)thiazole-4-carboxamide

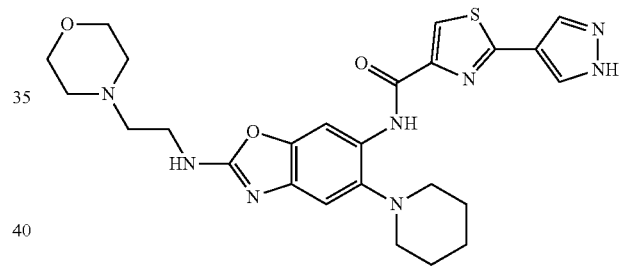

¹H NMR (300 MHz, DMSO-d₆) δ 13.42 (s, 1H), 10.67 (s, 1H), 8.40 (s, 2H), 8.27 (s, 1H), 8.01 (s, 1H), 7.79 (t, J=5.8 Hz, 1H), 7.20 (s, 1H), 3.58-3.51 (m, 4H), 3.39 (q, J=6.4 Hz, 2H), 2.84-2.77 (m, 4H), 2.53-2.49 (m, 2H), 2.44-2.37 (m, 4H), 1.86-1.76 (m, 4H), 1.65-1.55 (m, 2H).

LCMS (m/z): 523.7 (MH⁺).

I-53: N-(2-(methyl(2-morpholinoethyl)amino)-5-(piperidin-1-yl)benzo[d]oxazol-6-yl)-5-(1H-pyrazol-4-yl)furan-2-carboxamide

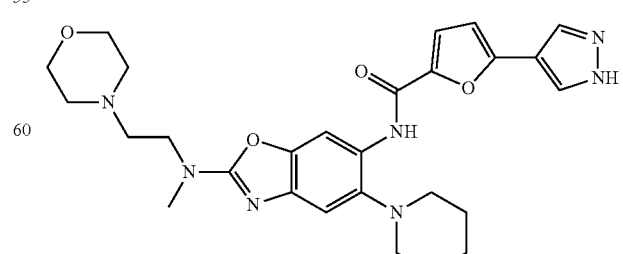

¹H NMR (300 MHz, DMSO-d₆) δ 13.26 (s, 1H), 9.78 (s, 1H), 8.32 (s, 1H), 8.17 (s, 1H), 7.90 (s, 1H), 7.26 (d, J=3.6 Hz, 1H), 7.23 (s, 1H), 6.77 (d, J=3.6 Hz, 1H), 3.59 (t, J=6.4 Hz, 2H), 3.53-3.45 (m, 4H), 3.12 (s, 3H), 2.84-2.76 (m, 4H), 2.54 (t, J=6.4 Hz, 2H), 2.45-2.38 (m, 4H), 1.82-1.71 (m, 4H), 1.63-1.54 (m, 2H).

LCMS (m/z): 520.7 (MH⁺).

I-54: N-(2-(methyl(2-morpholinoethyl)amino)-5-(piperidin-1-yl)benzo[d]oxazol-6-yl)-2-(1H-pyrazol-4-yl)thiazole-4-carboxamide

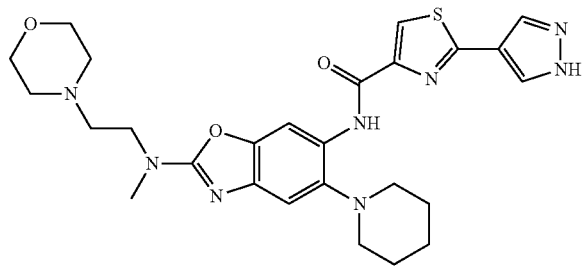 [SMILES: CN(CCN1CCOCC1)c1nc2cc(N3CCCCC3)c(NC(=O)c3csc(-c4cn[nH]c4)n3)cc2o1]

¹H NMR (300 MHz, DMSO-d₆) δ 13.42 (s, 1H), 10.66 (s, 1H), 8.44 (s, 1H), 8.41 (s, 1H), 8.28 (s, 1H), 8.01 (s, 1H), 7.21 (s, 1H), 3.59 (t, J=6.4 Hz, 2H), 3.54-3.45 (m, 4H), 3.12 (s, 3H), 2.85-2.76 (m, 4H), 2.54 (t, J=6.4 Hz, 2H), 2.45-2.39 (m, 4H), 1.86-1.77 (m, 4H), 1.66-1.55 (m, 2H).

LCMS (m/z): 537.8 (MH⁺).

Example 9

LPS Induced IL23p19 in THP-1 Cells (with IFNγ Primed) Assay

Materials and Equipment

THP-1 Cells (ATCC, Cat # TIB-202), Dimethyl Sulfoxide (DMSO) (Sigma-Aldrich, Cat # D2650), RPMI 1640 (Cellgro, Cat #10-040-CM), Fetal Bovine Serum (Sigma, Cat # F4135), Albumin From Bovine Serum (BSA) (Sigma-Aldrich, Cat # A7906), LPS (Serotype K-235, Sigma, Product Number L 2143), IFNγ (Peprotech, Cat #300-02)
Capture antibody: Human IL-23p19 ELISA (e-Bioscience, Cat. #14-7238-85),
Detection antibody: Primary Mouse Biotinylated anti-human IL-12(p40/p70) (e-Bioscience, Cat. #13-7129-85), Secondary HRP-conjugated Streptavidin (R&D Systems, Cat # DY998), 1×PBST Washing Buffer (PBS-Tween tablet) (VWR International, Cat #80058-558), ELISA Blocking Buffer (PBS with 1% BSA), ELISA Dilution Buffer (PBS with 1% BSA), 384 Well Flat-Bottom, MaxiSorp Black Immuno Plates (Thermo Scientific, Cat #12-565-346), 384 Well Flat-Bottom, White Tissue Culture Plates (Thermo Scientific, Cat #12-565-343), Super Signal ELISA Pico Chemiluminescent Substrate (Thermo Scientific, Cat #37070), Cell Titer Glo reagent (Promega, Cat # G7573), Positive control, IKK2VI inhibitor (Calbiochem, Cat #401483), AquaMax 4000 plate washer (Molecular Devices), Luminometer, Wallac Victor2 1420 Multilabel Counter.

Method

THP-1 Cells Stimulation:

On day 1, 50K/well THP-1 cells were seeded and primed with IFNγ (50 ng/mL) in 384-well plates for about 18 hours in RPMI media with 10% FBS. On day 2, the compound was serially diluted in DMSO from 5 mM in 3-fold dilutions, and then diluted 1:125 in RPMI media with 10% FBS. 50 μL/well 2× compound was added to 50 μL/well THP-1 cells (with IFNγ primed) in duplicate in 384 well tissue culture plates. The cells were pre-incubated with compound for 1 hour at 37° C., 5% CO₂ before addition of 10 μL/well 11×LPS to give a final concentration of 1 ug/mL LPS. Day 3, after stimulation for 18 hours at 37° C., 5% CO₂, the assay plate was centrifuged and 70 μL/well supernatant was harvested. IL-23p19 protein in 70 μL/well of supernatant was measured by sandwich ELISA, and 25 μl/well Cell Titer Glo reagent was added to the remaining cells to measure compound toxicity.

Human IL-23p19 Sandwich ELISA:

Maxisorp immuno ELISA plates were pre-coated with 25 μL/well of anti-IL-23p19 capture antibody (2.5 ug/mL) in PBS overnight at room temperature. After washing with 1×PBST, the plates were blocked using 100 μL/well of 1% BSA in PBS for 2 hours at room temperature. The plates were washed three times with 1×PBST and 70 μL/well supernatant were added. The plates were incubated at room temperature for 2 hours with shaking and washed three times with 1×PBST. 25 μL/well of biotin labeled anti-IL-12(p40/p70) detection antibody (100 ng/mL) in PBS with 1% BSA was added and the plates were incubated at room temperature for 2 hours with shaking. After washing three times with 1×PBST, 25 μL/well of streptavidin-HRP (1:200) in PBS with 1% BSA was added and the plates were incubated at room temperature for 20 minutes with shaking. The plates were washed three times with 1×PBST and 25 μL/well of Super Signal ELISA Pico Chemiluminescent Substrate were added. The plates were read with a luminometer, and the chemiluminescence values were entered into Athena (Rigel) for curve fitting, EC₅₀ calculation, and database storage. The results are shown in Table 1.

Example 10

Compound Screening Using DC Cells

Materials
Human PBMC cells (All Cells, Cat No. PB002)
RPMI growth media containing 10% FBS
IFNγ (Peprotech, Cat No. 300-02)
GMCSF (Peprotech, Cat No. 300-03) and IL4 (Peprotech Cat No. 200-04)
White clear bottom 96 well plates (Fisher, Cat No. 07-200-587, Corning #3903)
LPS (Make 2.5 mg/ml Stock in PBS) from Sigma Aldrich (Cat No. L2018-5MG)
Cell Titer Glo reagent (Promega, Cat No. G7573)
Positive controls, IKK2VI inhibitor (Calbiochem, Cat No. 401483)

Protocol

I. Differentiation of PBMC's to DC cells:

Human PBMC cells (400 million) obtained from the vendor were transferred into a T-175 flask containing 15 ml RPMI media (10% FBS) and incubate for 2 hours at 37° C. After 2 hours, the media including floating cells was aspirated out carefully and 12 ml of fresh RPMI media (10% FBS) containing GMCSF (100 ng/ml) and IL4 (20 ng/ml) was added, and the flask was kept in a 37° C. incubator for 7 days.

After 3 days, fresh GMCSF (100 ng/ml) and IL4 (20 ng/ml) were added to the flask and the incubation continued. After 7 days, the fully differentiated cells were harvested by spinning down (1200 rpm/5 min) and aspirating the media. The cells were suspended in fresh RPMI media (10% FBS) containing 50 ng/ml IFNγ (1000 U/ml) and then plated (50K/well in 100 µl) onto a white clear bottom 96 well plate and left in a 37° C. incubator for 24 hours.

II. Addition of Compounds:

After 24 hours incubation, 100 µl of RPMI media was added containing 2× concentrated test compound per well to the above cell-culture media (final concentration becomes 1×) and the plates were pre-incubated for 1 hour at 37° C. before stimulating with LPS.

After 1 hour compound pre-incubation, 10 µl per well of 20× concentrated LPS solution in RPMI media was added to give a final concentration of 1 µg/ml. The mixture was shaken and incubated the plates at 37° C. for an additional 18 hours.

155 µl of the supernatant was harvested from each well carefully (without the tip touching the bottom of the well) and to the remaining 50 µl/well of the cell culture plate was added 50 µl of Cell Titer Glo reagent. The mixture was incubated for 1-2 minutes on a shaker and the plate was read for luminescence intensity to determine the compound cytotoxicity. The cell culture supernatant collected above was used to carry out IL23 ELISA (65 µl—Supernatant) and IL10 ELISA (90 µl—Supernatant) as described below.

Example 11

Human IL-23 (p19/p40) ELISA Protocol (e-Biosciences)

Materials:
96-well high binding opaque white plates (from Pierce, Cat No. 15042);
1×PBS; 1×TBST washing buffer;
Blocking Solution: 0.5% Casein in PBS (from BDH, Cat No. 440203H);
Dilution Solution: 1% BSA in PBS (10% BSA from Fisher, Cat No. 37525);
Capture antibody: Rat anti-human IL-23 (p19) (e-Biosciences, Cat. No. 14-7238-85);
Detection antibody: Primary Mouse Biotinylated anti-human IL-12 (p40/p70) (e-biosciences, Cat No. 13-7129-85);
Secondary HRP-conjugated Streptavidin (R&D Systems, Cat No. DY998);
rHuman-IL-23 (e-biosciences, Cat No. 34-8239) (Suggested starting concentration=5 ng/ml in RPMI cell culture media);
Cell Culture Supernatant (65 µl from THP-1 cells primed with IFNγ (50 ng/ml-1000 U/ml) and stimulated with 0.01% SAC);
SuperSignal ELISA Pico Chemiluminescent substrate [Pierce, Cat No. 37069].
Coating Plates:
To 10.5 ml PBS add 50 µl of anti-IL23 (p19) was added capture antibody (2.5 µg/ml). The mixture was mixed well and 100 µl of the coating solution was added to each well of the 96 well white plates from Pierce. The wells were covered and incubated overnight at 4° C.
Blocking the Plates:
The anti-IL23 (p19)-antibody-coated plates were washed 2× using TBST (use plate washer) and blocked using 200 µl of 0.5% Casein for 1.5-2 hours at room temperature with shaking.
Addition of Supernatant and Detection:
The plates were washed 2× using TBST and the supernatant was transferred (65 µl/well) to the above pre-blocked/ IL23(p19)-antibody-coated 96 well plate, and incubated at room temperature for 1.5 hours with shaking.

The plates were washed 4× using TBST (plate washer) and 100 µl/well detection antibody solution prepared from 2 µl of biotin labeled anti-IL-12 (p40/p70) antibody in 11 ml 1% BSA/PBS solution (I-5000 dilution) was added. The plates were incubated for 1 hour with shaking at Room temperature.

Again, the plates were washed 4× with TBST and 100 µl of HRP labeled Streptavidin (R&D Systems) solution (10 µl/10 ml 1% BSA solution) was added, and the plates were incubated at room temperature for another 45 minutes with shaking.

After 45 minutes, the plates were washed with TBST 4× and 100 ul/well Super Signal ELISA Pico Chemiluminescent Substrate from Pierce (3.5 ml A+3.5 ml B+3.5 ml MQ water) was added. The plates were shaken for 1-2 minutes then read on a plate reader. The results are shown in Table 1.

TABLE 1

EC$_{50}$ results from the assays described in Examples 9 and 11

| Compound | IL23-p19 ELISA, Dendritic, LPS, 10 pt EC$_{50}$ (µM) | IL23-p19 ELISA, THP1-IFNy, LPS, 10 pt EC$_{50}$ (µM) |
|---|---|---|
| I-1 | 4.728 | 0.8979 |
| I-2 | 9999 | 9999 |
| I-3 | 0.0391 | 0.0314 |
| I-4 | 12.13 | 0.9006 |
| I-5 | 0.2571 | 0.4316 |
| I-6 | 13.99 | 40.53 |
| I-7 | 0.0136 | 0.026 |
| I-8 | 9999 | 0.6142 |
| I-9 | 0.8967 | 52.09 |
| I-10 | 2.987 | 4.631 |
| I-11 | 9999 | 228.5 |
| I-12 | 0.02 | 0.0539 |
| I-13 | 9999 | 2.934 |
| I-14 | 17.91 | 10.22 |
| I-15 | 1.688 | 73.05 |
| I-16 | 0.0322 | 0.0258 |
| I-17 | 1.021 | 1.228 |
| I-18 | 0.889 | 7.511 |
| I-19 | 0.6743 | 0.9384 |
| I-20 | 0.018 | 0.0224 |
| I-21 | 1.706 | 2.176 |
| I-22 | 3.183 | 0.6772 |
| I-23 | 0.1568 | 0.0757 |
| I-24 | 5.774 | 1.08 |
| I-25 | 0.1215 | 0.0482 |
| I-26 | 9999 | 1.183 |
| I-27 | 0.7471 | 0.5275 |
| I-28 | 9999 | 9999 |
| I-29 | 0.1057 | 0.3022 |
| I-30 | 9999 | 43.48 |
| I-31 | 0.4438 | 0.1441 |
| I-32 | 24.1 | 1.781 |
| I-33 | 9999 | 4454 |
| I-34 | 9999 | 8.325 |
| I-35 | 0.6658 | 0.3212 |
| I-36 | 9999 | 5.237 |
| I-37 | 9999 | 23.09 |
| I-38 | 0.0141 | 0.0316 |
| I-39 | 8.074 | 0.3549 |
| I-40 | 0.041 | 0.025 |
| I-41 | 2.584 | 0.1474 |
| I-42 | 0.0848 | 0.0606 |
| I-43 | 2.624 | 0.3436 |
| I-44 | 0.1008 | 0.0887 |
| I-45 | 0.4023 | 0.3422 |
| I-46 | 0.0375 | 0.0587 |
| I-47 | 0.058 | 0.0213 |

TABLE 1-continued

EC$_{50}$ results from the assays described in Examples 9 and 11

| Compound | IL23-p19 ELISA, Dendritic, LPS, 10 pt EC$_{50}$ (µM) | IL23-p19 ELISA, THP1-IFNy, LPS, 10 pt EC$_{50}$ (µM) |
|---|---|---|
| I-48 | 0.1231 | 0.0585 |
| I-49 | 0.0481 | 0.0504 |
| I-50 | 0.0757 | 0.1326 |
| I-51 | 0.0411 | 0.0742 |
| I-52 | 0.0371 | 0.02 |
| I-53 | 0.1213 | 0.1797 |
| I-54 | 0.0603 | 0.1057 |
| I-55 | 0.0303 | 0.024 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating a disease or condition for which an IRAK4 modulator or inhibitor is indicated, comprising administering to a subject a compound having a formula

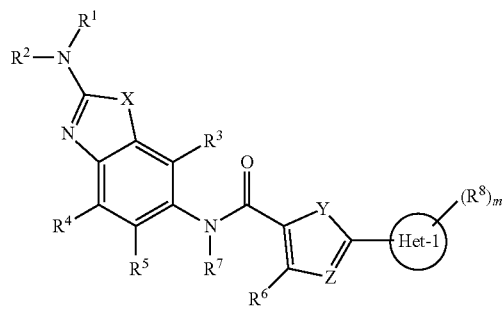

or a pharmaceutically acceptable salt thereof, wherein:
X is O or S;
Y is O or S;
Z is N or CR$^9$;
Het-1 is heterocyclyl;
R$^1$ and R$^2$ independently are H, aliphatic, heteroaliphatic, heterocyclyl, aryl, araliphatic, or together with the nitrogen to which they are attached, form a heterocyclic ring;
R$^3$, R$^4$, R$^5$, R$^6$ and R$^9$ independently are H, aliphatic, halo, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl or haloalkyl;
R$^7$ is H, aliphatic, heteroaliphatic, heterocyclyl, aryl or araliphatic;
each R$^8$ independently is aliphatic, halo, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl or haloalkyl; and
m is from 0 to the number of possible substituents on Het-1.

2. The method of claim 1, wherein Het-1 is heteroaryl.

3. The method of claim 1, wherein Het-1 is selected from furan, thiophene, pyrazole, pyrrole, imidazole, oxazole, thiazole, isoxazole, isothiazole, 1,2,3-triazole, 1,2,4-triazole, 1,3,4-triazole, 1,2,3-oxadiazole, 1,2,4-oxadiazole, 1,3,4-oxadiazole, 1,2,5-oxadiazole, 1,2,3-thiadiazole, 1,2,4-thiadiazole, 1,3,4-thiadiazole, 1,2,5-thiadiazole, tetrazole, pyrimidine, pyridine, 1,2,3-triazine, 1,2,4-triazine, 1,3,5-triazine, pyrazine, pyridazine, quinoline, isoquinoline, indole, isoindole, benzofuran, benzothiophene, benzoimidazole, benzopyrazole, benzotriazole, pyrrolo[2,3-b]pyridine, pyrrolo[3,2-b]pyridine, pyrrolo[2,3-c]pyridine, pyrrolo[3,2-c]pyridine, pyrrolo[3,4-b]pyridine or pyrrolo[3,4-c]pyridine.

4. The method of claim 1, wherein

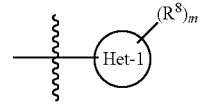

is selected from

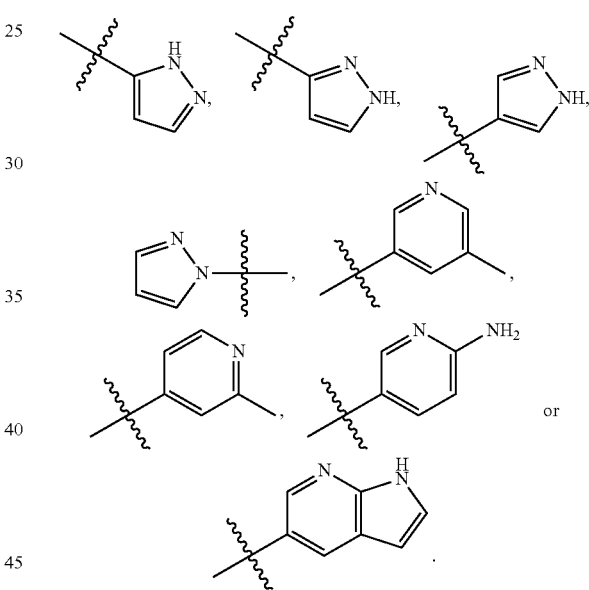

5. The method of claim 1, wherein at least one R$^8$ is —NH$_2$, —CH$_3$, —CF$_3$, —CF$_2$H or —CH$_2$CF$_3$.

6. The method of claim 1, wherein the compound has a formula selected from

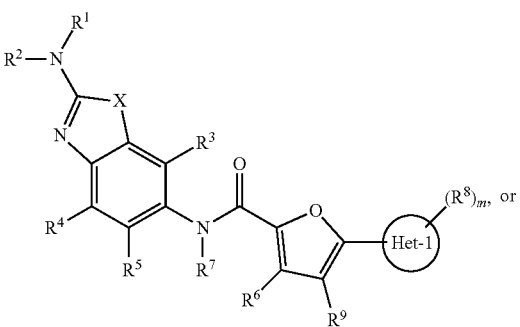

-continued

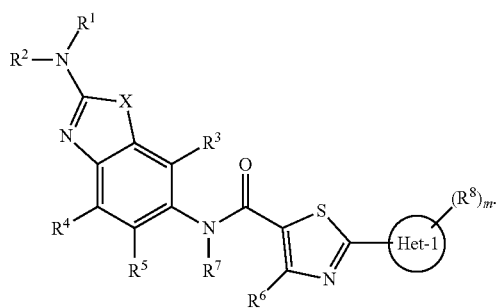

7. The method of claim 1, wherein the compound has formula selected from

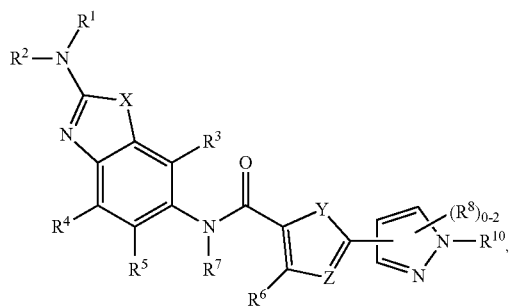

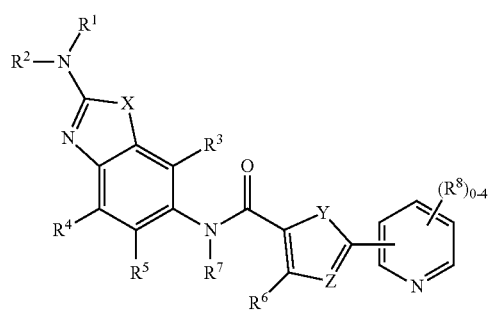

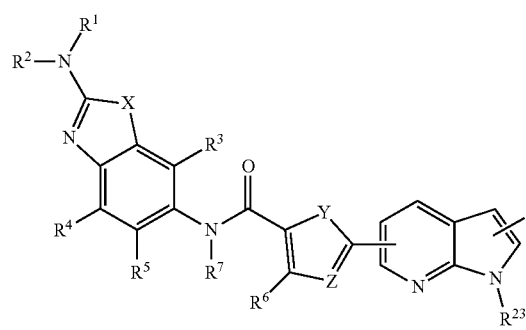

and

R$^{10}$ and R$^{23}$ are selected from H, aliphatic, heteroaliphatic, —O-aliphatic, heterocyclyl, aryl, araliphatic, —O-heterocyclyl, hydroxyl, cyano, carboxyl, carboxyl ester, acyl, amide, amino, sulfonyl, sulfonamide, or haloalkyl.

8. The method of claim 1, wherein the compound has a formula selected from

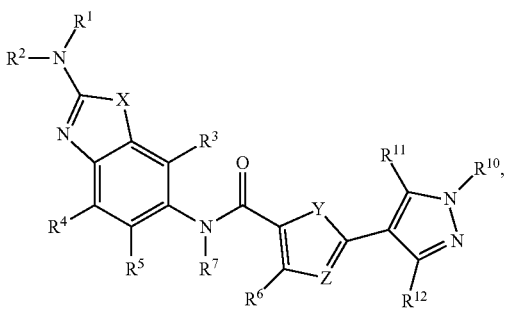

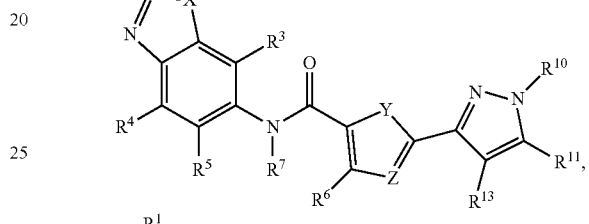

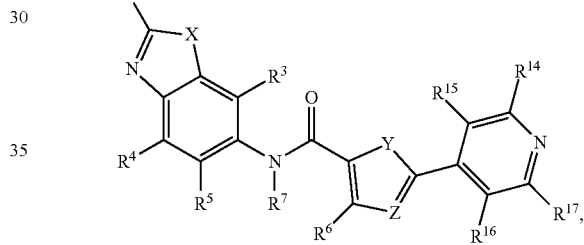

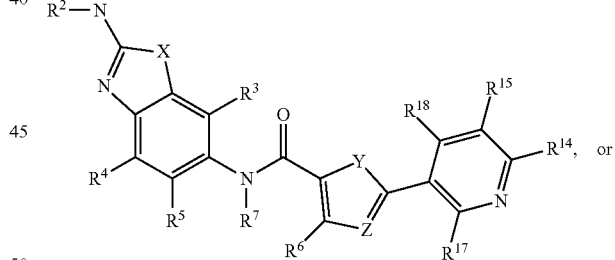

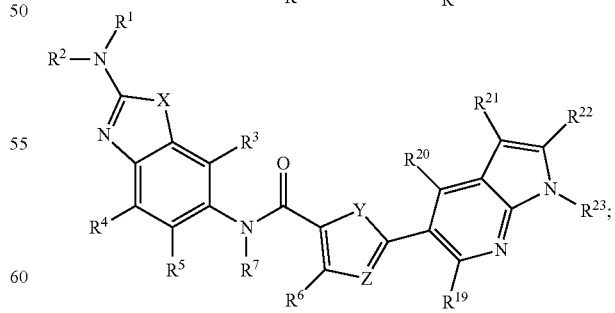

R$^{10}$ and R$^{23}$ independently are H, aliphatic, aryl or heterocyclyl; and

R$^{11}$, R$^{12}$, R$^{13}$, R$^{14}$, R$^{15}$, R$^{16}$, R$^{17}$, R$^{18}$, R$^{19}$, R$^{20}$, R$^{21}$ and R$^{22}$ independently are H, aliphatic, halogen, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl, or haloalkyl.
9. The method of claim 8, wherein the compound has a formula selected from
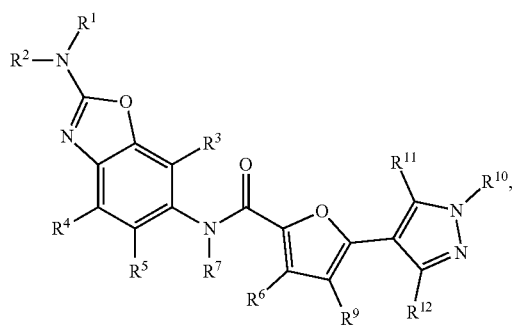
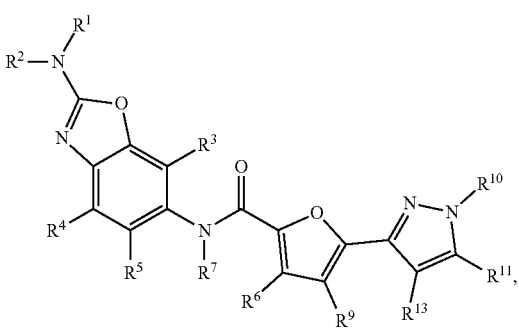
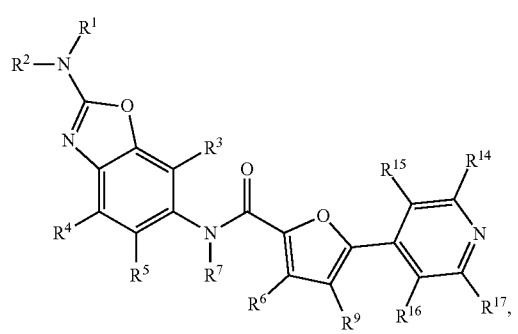
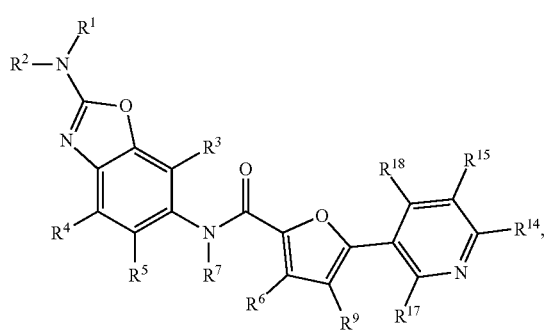
-continued
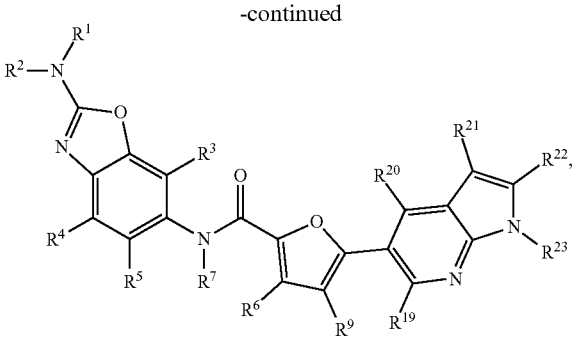
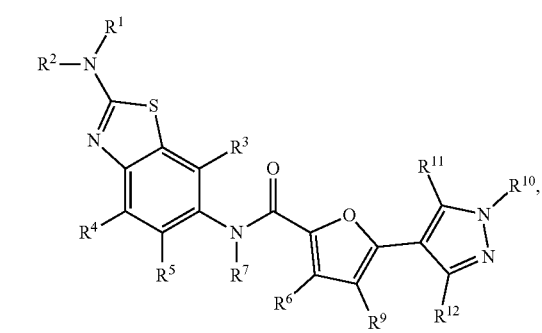
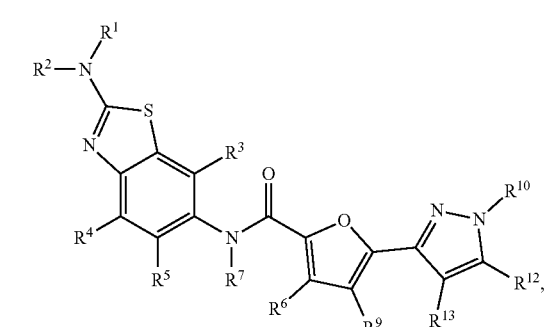
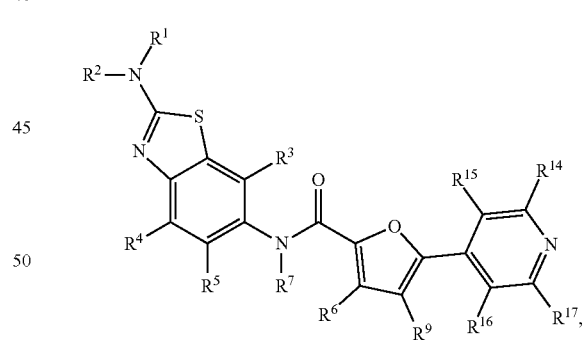
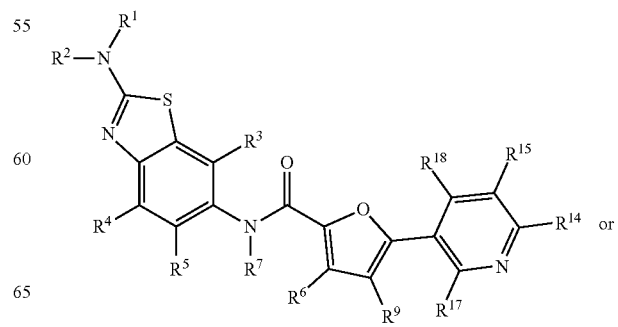
or

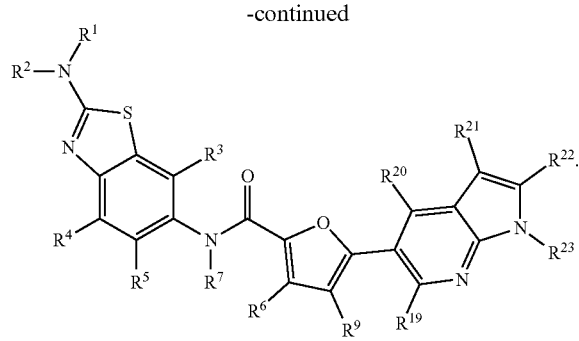
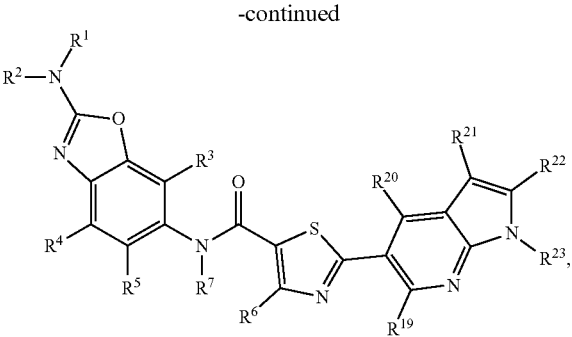
10. The method of claim 8, wherein the compound has a formula selected from
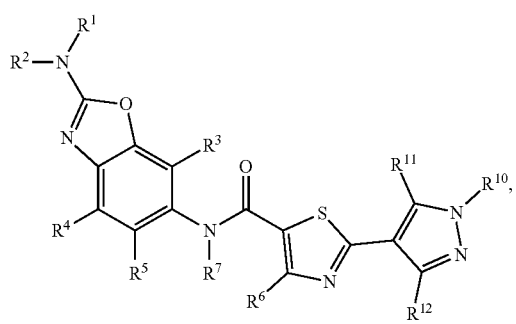
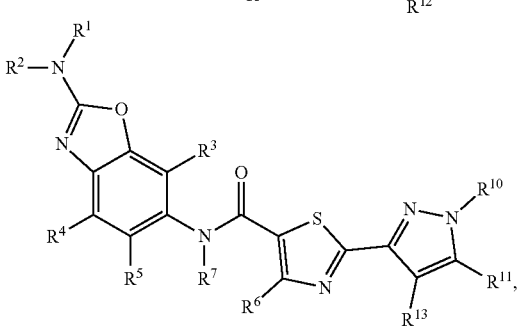
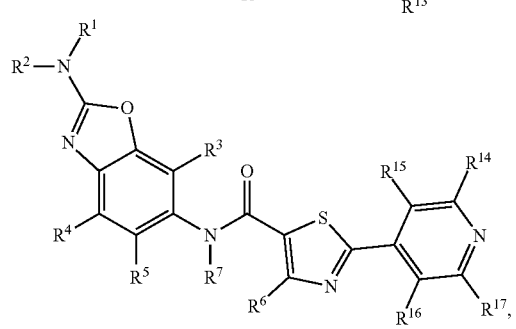
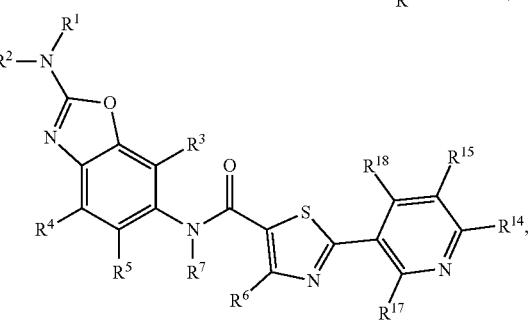
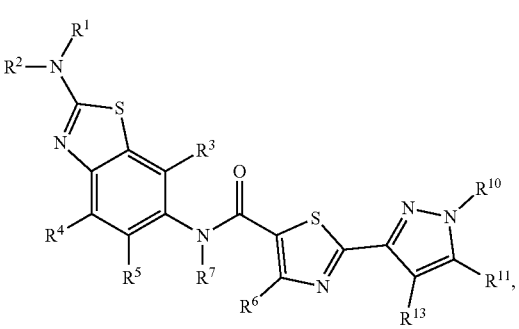
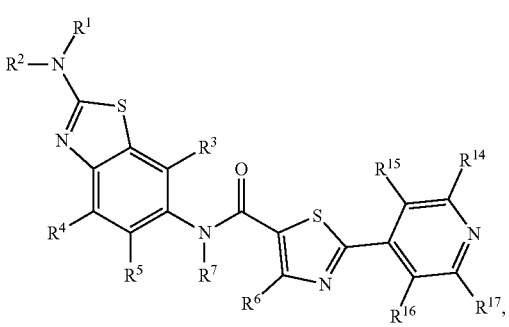
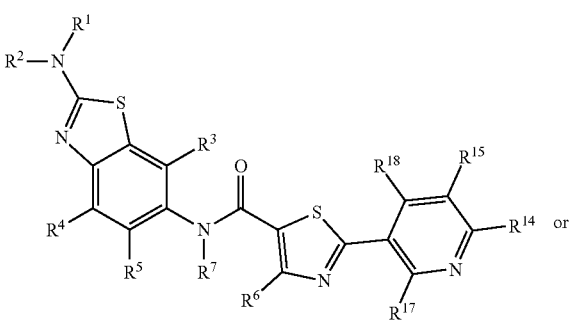

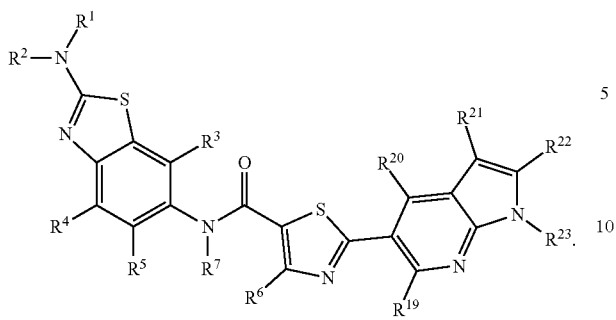

11. The method of claim 1, wherein $R^5$ is amino, aryl or heteroaryl.

12. The method of claim 1, wherein $R^5$ is selected from

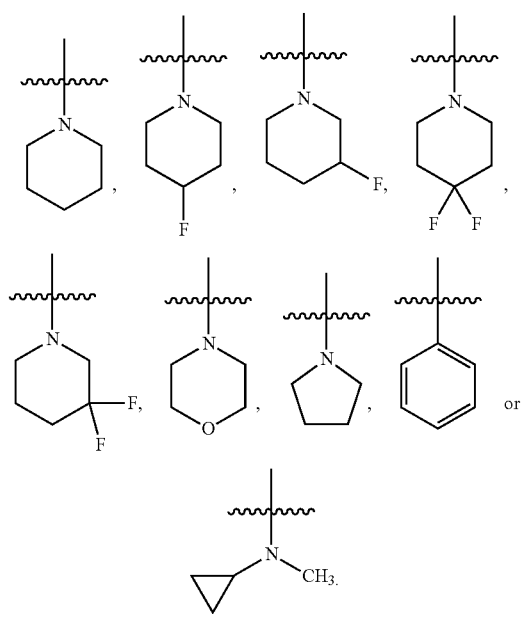

13. The method of claim 1, wherein $R^1$ is H or alkyl, and $R^2$ is aliphatic or heteroaliphatic.

14. The method of claim 1, wherein $R^1$—N—$R^2$ moiety is selected from

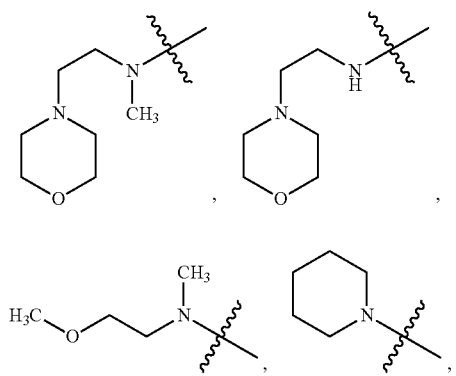

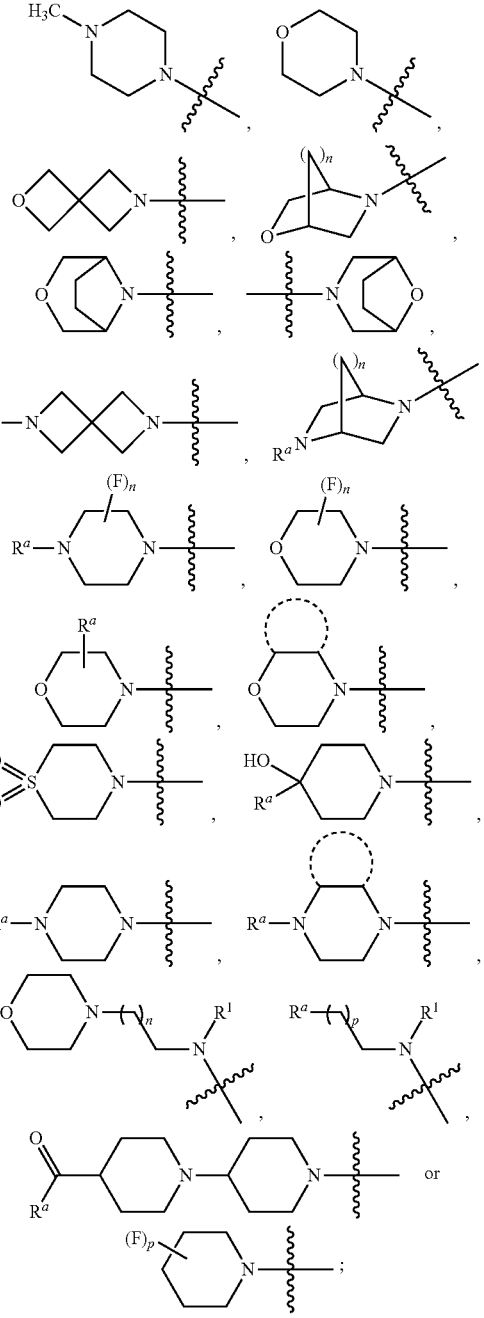

$R^a$ is aliphatic, haloalkyl or acyl;
n is 1 or 2; and
p is 0, 1 or 2.

15. The method of claim 1, wherein the compound is selected from

I-1: 5-(6-aminopyridin-3-yl)-N-(2-morpholino-5-(piperidin-1-yl)benzo[d]oxazol-6-yl)furan-2-carboxamide;

I-2: N-(2-morpholino-5-(piperidin-1-yl)benzo[d]oxazol-6-yl)-5-(1H-pyrrolo[2,3-b]pyridin-5-yl)furan-2-carboxamide;

I-3: N-(2-morpholino-5-(piperidin-1-yl)benzo[d]oxazol-6-yl)-5-(1H-pyrazol-4-yl)furan-2-carboxamide;

I-4: N-(2-morpholino-5-(piperidin-1-yl)benzo[d]oxazol-6-yl)-5-(1H-pyrazol-3-yl)furan-2-carboxamide;

I-5: 5-(6-aminopyridin-3-yl)-N-(2-morpholino-5-(piperidin-1-yl)benzo[d]thiazol-6-yl)furan-2-carboxamide;

I-6: N-(2-morpholino-5-(piperidin-1-yl)benzo[d]thiazol-6-yl)-5-(1H-pyrrolo[2,3-b]pyridin-5-yl)furan-2-carboxamide;

I-7: N-(2-morpholino-5-(piperidin-1-yl)benzo[d]thiazol-6-yl)-5-(1H-pyrazol-4-yl)furan-2-carboxamide;

I-8: N-(2-morpholino-5-(piperidin-1-yl)benzo[d]thiazol-6-yl)-5-(1H-pyrazol-3-yl)furan-2-carboxamide;

I-9: 5-(2-methylpyridin-4-yl)-N-(2-morpholino-5-(piperidin-1-yl)benzo[d]thiazol-6-yl)furan-2-carboxamide;

I-10: 5-(2-methylpyridin-4-yl)-N-(2-morpholino-5-(piperidin-1-yl)benzo[d]oxazol-6-yl)furan-2-carboxamide;

I-11: 2-(6-aminopyridin-3-yl)-N-(2-morpholino-5-(piperidin-1-yl)benzo[d]oxazol-6-yl)thiazole-4-carb oxamide;

I-12: N-(2-morpholino-5-(piperidin-1-yl)benzo[d]oxazol-6-yl)-2-(1H-pyrazol-4-yl)thiazole-4-carb oxamide;

I-13: N-(2-morpholino-5-(piperidin-1-yl)benzo[d]oxazol-6-yl)-2-(1H-pyrazol-3-yl)thiazole-4-carb oxamide;

I-14: 2-(2-methylpyridin-4-yl)-N-(2-morpholino-5-(piperidin-1-yl)benzo[d]oxazol-6-yl)thiazole-4-carboxamide;

I-15: 5-(6-aminopyridin-3-yl)-N-(2-(4-methylpiperazin-1-yl)-5-(piperidin-1-yl)benzo[d]oxazol-6-yl)furan-2-carboxamide;

I-16: N-(2-(4-methylpiperazin-1-yl)-5-(piperidin-1-yl)benzo[d]oxazol-6-yl)-5-(1H-pyrazol-4-yl)furan-2-carboxamide;

I-17: N-(2-(4-methylpiperazin-1-yl)-5-(piperidin-1-yl)benzo[d]oxazol-6-yl)-5-(1H-pyrazol-3-yl)furan-2-carboxamide;

I-18: N-(2-(4-methylpiperazin-1-yl)-5-(piperidin-1-yl)benzo[d]oxazol-6-yl)-5-(2-methylpyridin-4-yl)furan-2-carboxamide;

I-19: 2-(6-aminopyridin-3-yl)-N-(2-(4-methylpiperazin-1-yl)-5-(piperidin-1-yl)benzo[d]oxazol-6-yl)thiazole-4-carb oxamide;

I-20: N-(2-(4-methylpiperazin-1-yl)-5-(piperidin-1-yl)benzo[d]oxazol-6-yl)-2-(1H-pyrazol-4-yl)thiazole-4-carboxamide;

I-21: N-(2-(4-methylpiperazin-1-yl)-5-(piperidin-1-yl)benzo[d]oxazol-6-yl)-2-(1H-pyrazol-3-yl)thiazole-4-carboxamide;

I-22: N-(2-(4-methylpiperazin-1-yl)-5-(piperidin-1-yl)benzo[d]oxazol-6-yl)-2-(2-methylpyridin-4-yl)thiazole-4-carboxamide;

I-23: N-(5-(4-fluoropiperidin-1-yl)-2-morpholinobenzo[d]oxazol-6-yl)-5-(1H-pyrazol-4-yl)furan-2-carboxamide;

I-24: N-(5-(4-fluoropiperidin-1-yl)-2-morpholinobenzo[d]oxazol-6-yl)-5-(2-methylpyridin-4-yl)furan-2-carboxamide;

I-25: N-(5-(4-fluoropiperidin-1-yl)-2-morpholinobenzo[d]oxazol-6-yl)-2-(1H-pyrazol-4-yl)thiazole-4-carboxamide;

I-26: N-(5-(4-fluoropiperidin-1-yl)-2-morpholinobenzo[d]oxazol-6-yl)-2-(2-methylpyridin-4-yl)thiazole-4-carboxamide;

I-27: N-(5-(4,4-difluoropiperidin-1-yl)-2-morpholinobenzo[d]oxazol-6-yl)-5-(1H-pyrazol-4-yl)furan-2-carboxamide;

I-28: N-(5-(4,4-difluoropiperidin-1-yl)-2-morpholinobenzo[d]oxazol-6-yl)-5-(2-methylpyridin-4-yl)furan-2-carboxamide;

I-29: N-(5-(4,4-difluoropiperidin-1-yl)-2-morpholinobenzo[d]oxazol-6-yl)-2-(1H-pyrazol-4-yl)thiazole-4-carboxamide;

I-30: N-(5-(4,4-difluoropiperidin-1-yl)-2-morpholinobenzo[d]oxazol-6-yl)-2-(2-methylpyridin-4-yl)thiazole-4-carboxamide;

I-31: N-(2,5-di(piperidin-1-yl)benzo[d]oxazol-6-yl)-5-(1H-pyrazol-4-yl)furan-2-carboxamide;

I-32: N-(2,5-di(piperidin-1-yl)benzo[d]oxazol-6-yl)-5-(1H-pyrazol-3-yl)furan-2-carboxamide;

I-33: N-(2,5-di(piperidin-1-yl)benzo[d]oxazol-6-yl)-5-(2-methylpyridin-4-yl)furan-2-carboxamide;

I-34: 2-(6-aminopyridin-3-yl)-N-(2,5-di(piperidin-1-yl)benzo[d]oxazol-6-yl)thiazole-4-carboxamide;

I-35: N-(2,5-di(piperidin-1-yl)benzo[d]oxazol-6-yl)-2-(1H-pyrazol-4-yl)thiazole-4-carboxamide;

I-36: N-(2,5-di(piperidin-1-yl)benzo[d]oxazol-6-yl)-2-(1H-pyrazol-3-yl)thiazole-4-carboxamide;

I-37: N-(2,5-di(piperidin-1-yl)benzo[d]oxazol-6-yl)-2-(2-methylpyridin-4-yl)thiazole-4-carboxamide;

I-38: N-(5-(3-fluoropiperidin-1-yl)-2-morpholinobenzo[d]oxazol-6-yl)-5-(1H-pyrazol-4-yl)furan-2-carboxamide;

I-39: N-(5-(3-fluoropiperidin-1-yl)-2-morpholinobenzo[d]oxazol-6-yl)-5-(2-methylpyridin-4-yl)furan-2-carboxamide;

I-40: N-(5-(3-fluoropiperidin-1-yl)-2-morpholinobenzo[d]oxazol-6-yl)-2-(1H-pyrazol-4-yl)thiazole-4-carboxamide;

I-41: N-(5-(3-fluoropiperidin-1-yl)-2-morpholinobenzo[d]oxazol-6-yl)-2-(2-methylpyridin-4-yl)thiazole-4-carboxamide;

I-42: N-(5-(3,3-difluoropiperidin-1-yl)-2-morpholinobenzo[d]oxazol-6-yl)-5-(1H-pyrazol-4-yl)furan-2-carboxamide;

I-43: N-(5-(3,3-difluoropiperidin-1-yl)-2-morpholinobenzo[d]oxazol-6-yl)-5-(2-methylpyridin-4-yl)furan-2-carboxamide;

I-44: N-(5-(3,3-difluoropiperidin-1-yl)-2-morpholinobenzo[d]oxazol-6-yl)-2-(1H-pyrazol-4-yl)thiazole-4-carboxamide;

I-45: N-(5-(3,3-difluoropiperidin-1-yl)-2-morpholinobenzo[d]oxazol-6-yl)-2-(2-methylpyridin-4-yl)thiazole-4-carboxamide;

I-46: N-(2-morpholino-5-(pyrrolidin-1-yl)benzo[d]oxazol-6-yl)-5-(1H-pyrazol-4-yl)furan-2-carboxamide;

I-47: N-(2-morpholino-5-(pyrrolidin-1-yl)benzo[d]oxazol-6-yl)-2-(1H-pyrazol-4-yl)thiazole-4-carboxamide;

I-48: N-(2,5-dimorpholinobenzo[d]oxazol-6-yl)-5-(1H-pyrazol-4-yl)furan-2-carboxamide;

I-49: N-(2,5-dimorpholinobenzo[d]oxazol-6-yl)-2-(1H-pyrazol-4-yl)thiazole-4-carboxamide;

I-50: N-(2-((2-methoxyethyl)(methyl)amino)-5-(piperidin-1-yl)benzo[d]oxazol-6-yl)-5-(1H-pyrazol-4-yl)furan-2-carboxamide;

I-51: N-(2-((2-methoxyethyl)(methyl)amino)-5-(piperidin-1-yl)benzo[d]oxazol-6-yl)-2-(1H-pyrazol-4-yl)thiazole-4-carboxamide;

I-52: N-(2-((2-morpholinoethyl)amino)-5-(piperidin-1-yl)benzo[d]oxazol-6-yl)-2-(1H-pyrazol-4-yl)thiazole-4-carboxamide;

I-53: N-(2-(methyl(2-morpholinoethyl)amino)-5-(piperidin-1-yl)benzo[d]oxazol-6-yl)-5-(1H-pyrazol-4-yl)furan-2-carboxamide;

I-54: N-(2-(methyl(2-morpholinoethyl)amino)-5-(piperidin-1-yl)benzo[d]oxazol-6-yl)-2-(1H-pyrazol-4-yl)thiazole-4-carboxamide;

I-55: N-(2-((2-morpholinoethyl)amino)-5-(piperidin-1-yl)benzo[d]oxazol-6-yl)-5-(1H-pyrazol-4-yl)furan-2-carboxamide;

or a pharmaceutically acceptable salt thereof.

16. The method of claim 1, further comprising administering an additional therapeutic agent.

17. The method of claim 16, wherein the additional therapeutic agent is an immunooncological agent.

18. A method, comprising contacting an IRAK4 protein with a compound having a formula

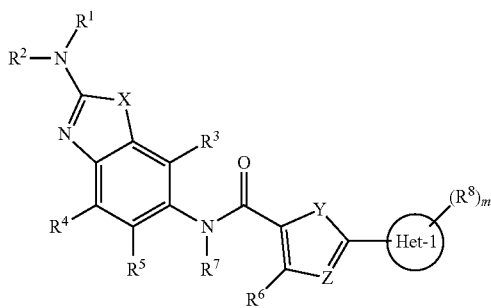

or a pharmaceutically acceptable salt, solvate, hydrate, or N-oxide thereof, wherein:

X is O or S;

Y is O or S;

Z is N or $CR^9$;

Het-1 is heterocyclyl;

$R^1$ and $R^2$ independently are H, aliphatic, heteroaliphatic, heterocyclyl, aryl, araliphatic, or together with the nitrogen to which they are attached, form a heterocyclic ring;

$R^3$, $R^4$, $R^5$, $R^6$ and $R^9$ independently are H, aliphatic, halo, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl or haloalkyl;

$R^7$ is H, aliphatic, heteroaliphatic, heterocyclyl, aryl or araliphatic;

each $R^8$ independently is aliphatic, halo, heteroaliphatic, —O-aliphatic, heterocyclyl, aryl, araliphatic, —O-heterocyclyl, hydroxyl, nitro, cyano, carboxyl, carboxyl ester, acyl, amide, amino, sulfonyl, sulfonamide, sulfanyl, sulfinyl or haloalkyl; and m is from 0 to the number of possible substituents on Het-1.

19. The method of claim 1, wherein the disease or condition is an auto-immune disease, inflammatory disorder, or immune regulatory disorder.

20. The method of claim 1, wherein the disease or condition comprises transplant or tissue rejection, a graft-versus-host disease, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis *nodosa*, myocardosis, scleroderma, Wegener's granuloma, Sjögren's syndrome, adiposis, eosinophilic fasciitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, non-alcoholic steatohepatitis (NASH), hepatic failure, fulminant hepatic failure, late-onset hepatic failure, "acute-on-chronic" liver failure, augmentation of chemotherapeutic effect, cytomegalovirus infection, HCMV infection, AIDS, senile dementia, Parkinson's disease, trauma, chronic bacterial infection, or a combination thereof.

21. The method of claim 1, wherein the disease or condition is an inflammatory skin disease, psoriasis, palmoplantar psoriasis, primary biliary cirrhosis, sclerosing cholangitis, or systemic juvenile idiopathic arthritis.

* * * * *